(12) United States Patent
Nelson et al.

(10) Patent No.: US 8,287,541 B2
(45) Date of Patent: *Oct. 16, 2012

(54) FRACTURE FIXATION DEVICE, TOOLS AND METHODS

(75) Inventors: Charles L. Nelson, Santa Rosa, CA (US); Heber Saravia, Santa Rosa, CA (US); Stephen R. McDaniel, San Rafael, CA (US); Trung Ho Pham, Santa Rosa, CA (US); Kai U. Mazur, Santa Rosa, CA (US); Stephen B. Gunther, Cloverdale, CA (US); Nathan Brown, Santa Rosa, CA (US)

(73) Assignee: Sonoma Orthopedic Products, Inc., Santa Rosa, CA (US)

( * ) Notice: Subject to any disclaimer, the term of this patent is extended or adjusted under 35 U.S.C. 154(b) by 562 days.

This patent is subject to a terminal disclaimer.

(21) Appl. No.: 12/482,406

(22) Filed: Jun. 10, 2009

(65) Prior Publication Data

US 2010/0023010 A1 Jan. 28, 2010

Related U.S. Application Data

(63) Continuation-in-part of application No. 11/383,269, filed on May 15, 2006, now Pat. No. 7,846,162, and application No. 12/482,406, which is a continuation-in-part of application No. 11/383,800, filed on May 17, 2006, now abandoned, said application No. 12/482,406 is a continuation-in-part of application No. 11/944,366, filed on Nov. 21, 2007, now Pat. No. 7,909,825.

(60) Provisional application No. 60/682,652, filed on May 18, 2005, provisional application No. 60/867,011, filed on Nov. 22, 2006, provisional application No. 60/866,976, filed on Nov. 22, 2006, provisional application No. 60/949,071, filed on Jul. 11, 2007, provisional application No. 61/060,440, filed on Jun. 10, 2008, provisional application No. 61/060,445, filed on Jun. 10, 2008, provisional application No. 61/060,450, filed on Jun. 10, 2008, provisional application No. 61/100,635, filed on Sep. 26, 2008, provisional application No. 61/100,652, filed on Sep. 26, 2008, provisional application No. 61/122,563, filed on Dec. 15, 2008, provisional application No. 61/138,920, filed on Dec. 18, 2008, provisional application No. 61/117,901, filed on Nov. 25, 2008.

(51) Int. Cl.
*A61B 17/58* (2006.01)

(52) U.S. Cl. ............................................. 606/63; 606/62

(58) Field of Classification Search ............... 606/62–68; 138/119; 600/139–152; 411/21
See application file for complete search history.

(56) References Cited

U.S. PATENT DOCUMENTS

| | | |
|---|---|---|
| 958,127 A | 5/1910 | Hufrud |
| 1,169,635 A | 1/1916 | Grimes |
| 1,790,841 A | 2/1931 | Rosen |
| 2,502,267 A | 3/1950 | McPherson |
| 2,685,877 A | 8/1954 | Dobelle |
| 2,998,007 A | 8/1961 | Herzog |
| 3,118,444 A | 1/1964 | Serrato, Jr. |
| 3,626,935 A | 12/1971 | Pollock et al. |
| 3,710,789 A | 1/1973 | Ersek |
| 3,759,257 A | 9/1973 | Fischer et al. |
| 3,760,802 A | 9/1973 | Fischer et al. |
| 3,779,239 A | 12/1973 | Fischer et al. |
| 3,791,380 A | 2/1974 | Dawidowski |
| 3,846,846 A | 11/1974 | Fischer |
| 3,955,565 A | 5/1976 | Johnson, Jr. |
| 3,978,528 A | 9/1976 | Crep |
| 3,986,504 A | 10/1976 | Avila |
| 4,007,528 A | 2/1977 | Shea et al. |
| 4,011,602 A | 3/1977 | Rybicki et al. |
| 4,016,874 A | 4/1977 | Maffei et al. |
| 4,065,816 A | 1/1978 | Sawyer |
| 4,091,806 A | 5/1978 | Aginsky |
| 4,146,022 A | 3/1979 | Johnson et al. |
| 4,164,794 A | 8/1979 | Spector et al. |
| 4,190,044 A | 2/1980 | Wood |
| D255,048 S | 5/1980 | Miller |
| 4,204,531 A | 5/1980 | Aginsky |

| | | | | | | |
|---|---|---|---|---|---|---|
| 4,227,518 A | 10/1980 | Aginsky | | 5,034,013 A | 7/1991 | Kyle et al. |
| 4,236,512 A | 12/1980 | Aginsky | | 5,035,697 A | 7/1991 | Frigg |
| 4,237,875 A | 12/1980 | Termanini | | 5,037,423 A | 8/1991 | Kenna |
| 4,246,662 A | 1/1981 | Pastrick | | 5,041,114 A | 8/1991 | Chapman et al. |
| 4,262,665 A | 4/1981 | Roalstad et al. | | 5,041,115 A | 8/1991 | Frigg et al. |
| 4,275,717 A | 6/1981 | Bolesky | | 5,053,035 A | 10/1991 | McLaren |
| 4,293,962 A | 10/1981 | Fuson | | 5,057,103 A | 10/1991 | Davis |
| 4,294,251 A | 10/1981 | Greenwald et al. | | 5,062,854 A | 11/1991 | Noble et al. |
| 4,312,336 A | 1/1982 | Danieletto et al. | | 5,066,296 A | 11/1991 | Chapman et al. |
| 4,338,926 A | 7/1982 | Kummer et al. | | 5,084,050 A | 1/1992 | Draenert |
| 4,351,069 A | 9/1982 | Ballintyn et al. | | 5,092,892 A | 3/1992 | Ashby |
| 4,352,212 A | 10/1982 | Greene et al. | | 5,098,433 A | 3/1992 | Freedland |
| 4,353,358 A * | 10/1982 | Emerson ............. 600/139 | | 5,102,413 A | 4/1992 | Poddar |
| 4,379,451 A | 4/1983 | Getscher | | 5,108,404 A | 4/1992 | Scholten et al. |
| 4,409,974 A | 10/1983 | Freedland | | 5,112,333 A | 5/1992 | Fixel |
| 4,453,539 A | 6/1984 | Raftopoulos et al. | | 5,116,335 A | 5/1992 | Hannon et al. |
| 4,457,301 A | 7/1984 | Walker | | 5,116,380 A | 5/1992 | Hewka et al. |
| 4,462,394 A | 7/1984 | Jacobs | | 5,122,141 A | 6/1992 | Simpson et al. |
| 4,467,794 A | 8/1984 | Maffei et al. | | 5,122,146 A | 6/1992 | Chapman et al. |
| RE31,809 E | 1/1985 | Danieletto et al. | | 5,124,106 A | 6/1992 | Morr et al. |
| 4,492,226 A | 1/1985 | Belykh et al. | | 5,147,408 A | 9/1992 | Noble et al. |
| 4,503,847 A | 3/1985 | Mouradian | | 5,152,766 A | 10/1992 | Kirkley |
| 4,519,100 A | 5/1985 | Wills et al. | | 5,163,963 A | 11/1992 | Hewka et al. |
| 4,520,511 A | 6/1985 | Gianezio et al. | | 5,171,324 A | 12/1992 | Campana et al. |
| 4,522,200 A | 6/1985 | Stednitz | | 5,176,681 A | 1/1993 | Lawes et al. |
| 4,552,136 A | 11/1985 | Kenna | | 5,178,621 A | 1/1993 | Cook et al. |
| 4,589,883 A | 5/1986 | Kenna | | 5,190,544 A | 3/1993 | Chapman et al. |
| 4,590,930 A | 5/1986 | Kurth et al. | | 5,190,546 A | 3/1993 | Jervis |
| 4,604,997 A | 8/1986 | De Bastiani et al. | | 5,192,281 A | 3/1993 | de la Caffiniere |
| 4,621,627 A | 11/1986 | DeBastiani et al. | | 5,197,966 A | 3/1993 | Sommerkamp |
| 4,622,959 A | 11/1986 | Marcus | | 5,197,990 A | 3/1993 | Lawes et al. |
| 4,628,920 A | 12/1986 | Mathys, Jr. et al. | | 5,201,735 A | 4/1993 | Chapman et al. |
| 4,632,101 A | 12/1986 | Freedland | | 5,201,767 A | 4/1993 | Caldarise et al. |
| 4,643,177 A | 2/1987 | Sheppard et al. | | 5,263,955 A | 11/1993 | Baumgart et al. |
| 4,651,724 A | 3/1987 | Berentey et al. | | 5,268,000 A | 12/1993 | Ottieri et al. |
| 4,653,487 A | 3/1987 | Maale | | 5,281,224 A | 1/1994 | Faccioli et al. |
| 4,667,663 A | 5/1987 | Miyata | | 5,292,322 A | 3/1994 | Faccioli et al. |
| D290,399 S | 6/1987 | Kitchens | | 5,295,991 A | 3/1994 | Frigg |
| 4,681,590 A | 7/1987 | Tansey | | 5,303,718 A | 4/1994 | Krajicek |
| 4,697,585 A | 10/1987 | Williams | | 5,314,489 A | 5/1994 | Hoffman et al. |
| 4,705,027 A | 11/1987 | Klaue | | 5,320,622 A | 6/1994 | Faccioli et al. |
| 4,705,032 A | 11/1987 | Keller | | 5,320,623 A | 6/1994 | Pennig |
| 4,721,103 A | 1/1988 | Freedland | | 5,326,376 A | 7/1994 | Warner et al. |
| 4,753,657 A | 6/1988 | Lee et al. | | 5,334,184 A | 8/1994 | Bimman |
| 4,776,330 A | 10/1988 | Chapman et al. | | 5,342,360 A | 8/1994 | Faccioli et al. |
| 4,781,181 A | 11/1988 | Tanguy | | 5,342,362 A | 8/1994 | Kenyon et al. |
| 4,805,595 A * | 2/1989 | Kanbara ............. 600/140 | | 5,346,496 A | 9/1994 | Pennig |
| 4,805,607 A | 2/1989 | Engelhardt et al. | | 5,350,379 A | 9/1994 | Spievack |
| 4,813,963 A | 3/1989 | Hori et al. | | 5,352,227 A | 10/1994 | O'Hara |
| 4,817,591 A | 4/1989 | Klaue et al. | | 5,358,534 A | 10/1994 | Dudasik et al. |
| 4,827,919 A | 5/1989 | Barbarito et al. | | 5,364,398 A | 11/1994 | Chapman et al. |
| 4,828,277 A | 5/1989 | De Bastiani et al. | | 5,368,594 A | 11/1994 | Martin et al. |
| 4,854,312 A | 8/1989 | Raftopoulos et al. | | 5,376,090 A | 12/1994 | Pennig |
| 4,858,602 A | 8/1989 | Seidel et al. | | 5,380,328 A | 1/1995 | Morgan |
| 4,862,883 A | 9/1989 | Freeland | | 5,383,932 A | 1/1995 | Wilson et al. |
| 4,871,369 A | 10/1989 | Muller | | 5,387,243 A | 2/1995 | Devanathan |
| 4,875,475 A | 10/1989 | Comte et al. | | 5,397,328 A | 3/1995 | Behrens et al. |
| 4,896,662 A | 1/1990 | Noble | | 5,403,321 A | 4/1995 | DiMarco |
| 4,904,048 A * | 2/1990 | Sogawa et al. ............. 385/118 | | 5,411,503 A | 5/1995 | Hollstien et al. |
| 4,921,499 A | 5/1990 | Hoffman et al. | | 5,415,660 A | 5/1995 | Campbell et al. |
| 4,927,424 A | 5/1990 | McConnell et al. | | 5,417,695 A | 5/1995 | Axelson, Jr. |
| 4,932,969 A | 6/1990 | Frey et al. | | RE34,985 E | 6/1995 | Pennig |
| 4,943,291 A | 7/1990 | Tanguy | | 5,433,718 A | 7/1995 | Brinker |
| 4,946,179 A | 8/1990 | De Bastiani et al. | | 5,433,720 A | 7/1995 | Faccioli et al. |
| 4,959,066 A | 9/1990 | Dunn et al. | | 5,441,500 A | 8/1995 | Seidel et al. |
| 4,969,889 A | 11/1990 | Greig | | 5,443,477 A | 8/1995 | Marin et al. |
| 4,976,258 A | 12/1990 | Richter et al. | | 5,445,642 A | 8/1995 | McNulty et al. |
| 4,978,349 A | 12/1990 | Frigg | | 5,454,813 A | 10/1995 | Lawes |
| 4,978,358 A | 12/1990 | Bobyn | | 5,454,816 A | 10/1995 | Ashby |
| 4,988,349 A | 1/1991 | Pennig | | 5,458,599 A | 10/1995 | Adobbati |
| 5,002,547 A | 3/1991 | Poggie et al. | | 5,458,651 A | 10/1995 | Lawes |
| 5,002,580 A | 3/1991 | Noble et al. | | 5,458,653 A | 10/1995 | Davidson |
| 5,006,120 A | 4/1991 | Carter et al. | | 5,472,444 A | 12/1995 | Huebner et al. |
| 5,013,314 A | 5/1991 | Firica et al. | | 5,478,341 A | 12/1995 | Cook et al. |
| 5,019,077 A | 5/1991 | De Bastiani et al. | | 5,480,400 A | 1/1996 | Berger |
| 5,026,374 A | 6/1991 | Dezza et al. | | 5,484,438 A | 1/1996 | Pennig |
| 5,027,799 A | 7/1991 | Laico et al. | | 5,484,446 A | 1/1996 | Burke et al. |
| 5,030,222 A | 7/1991 | Calandruccio et al. | | 5,505,734 A | 4/1996 | Caniggia et al. |
| 5,034,012 A | 7/1991 | Frigg | | 5,514,137 A | 5/1996 | Coutts |

| Patent No. | Date | Inventor(s) |
|---|---|---|
| 5,516,335 A | 5/1996 | Kummer et al. |
| 5,520,695 A | 5/1996 | Luckman |
| 5,531,748 A | 7/1996 | de la Caffiniere |
| 5,534,004 A | 7/1996 | Santangelo |
| 5,545,162 A | 8/1996 | Huebner |
| 5,549,610 A | 8/1996 | Russell et al. |
| 5,549,706 A | 8/1996 | McCarthy |
| 5,554,192 A | 9/1996 | Crowninshield |
| 5,556,433 A | 9/1996 | Gabriel et al. |
| 5,562,673 A | 10/1996 | Koblish et al. |
| 5,562,674 A | 10/1996 | Stalcup et al. |
| 5,562,675 A | 10/1996 | McNulty et al. |
| 5,571,189 A | 11/1996 | Kuslich |
| 5,571,204 A | 11/1996 | Nies |
| 5,573,536 A | 11/1996 | Grosse et al. |
| 5,578,035 A | 11/1996 | Lin |
| 5,586,985 A | 12/1996 | Putnam et al. |
| 5,591,169 A | 1/1997 | Benoist |
| 5,591,196 A | 1/1997 | Marin et al. |
| 5,593,451 A | 1/1997 | Averill et al. |
| 5,593,452 A | 1/1997 | Higham et al. |
| 5,605,713 A | 2/1997 | Boltong |
| 5,607,431 A | 3/1997 | Dudasik et al. |
| 5,613,970 A | 3/1997 | Houston et al. |
| 5,618,286 A | 4/1997 | Brinker |
| 5,618,300 A | 4/1997 | Marin et al. |
| 5,620,449 A | 4/1997 | Faccioli et al. |
| 5,624,440 A | 4/1997 | Huebner et al. |
| 5,643,258 A | 7/1997 | Robioneck et al. |
| 5,645,545 A | 7/1997 | Bryant |
| 5,645,599 A | 7/1997 | Samani |
| 5,658,283 A | 8/1997 | Huebner |
| 5,658,287 A | 8/1997 | Hofmann et al. |
| 5,658,292 A | 8/1997 | Axelson, Jr. |
| 5,658,293 A | 8/1997 | Vanlaningham |
| 5,658,351 A | 8/1997 | Dudasik et al. |
| 5,662,648 A | 9/1997 | Faccioli et al. |
| 5,662,649 A | 9/1997 | Huebner |
| 5,662,712 A | 9/1997 | Pathak et al. |
| 5,665,090 A | 9/1997 | Rockwood et al. |
| 5,665,091 A | 9/1997 | Noble et al. |
| 5,681,316 A | 10/1997 | DeOrio et al. |
| 5,681,318 A | 10/1997 | Pennig et al. |
| 5,683,389 A | 11/1997 | Orsak |
| 5,683,460 A | 11/1997 | Persoons |
| 5,688,271 A | 11/1997 | Faccioli et al. |
| 5,688,279 A | 11/1997 | McNulty et al. |
| 5,690,634 A | 11/1997 | Muller et al. |
| 5,693,047 A | 12/1997 | Meyers et al. |
| 5,693,048 A | 12/1997 | Stalcup et al. |
| 5,695,729 A | 12/1997 | Chow et al. |
| 5,697,930 A | 12/1997 | Itoman et al. |
| 5,702,215 A | 12/1997 | Li |
| 5,702,481 A | 12/1997 | Lin |
| 5,702,487 A | 12/1997 | Averill et al. |
| 5,707,370 A | 1/1998 | Berki et al. |
| 5,718,704 A | 2/1998 | Medoff |
| 5,728,096 A | 3/1998 | Faccioli et al. |
| 5,741,256 A | 4/1998 | Bresina |
| 5,741,266 A | 4/1998 | Moran et al. |
| 5,749,872 A | 5/1998 | Kyle et al. |
| 5,749,880 A | 5/1998 | Banas et al. |
| 5,759,184 A | 6/1998 | Santangelo |
| 5,766,178 A | 6/1998 | Michielli et al. |
| 5,766,179 A | 6/1998 | Faccioli et al. |
| 5,766,180 A | 6/1998 | Winquist |
| 5,772,662 A | 6/1998 | Chapman et al. |
| 5,776,194 A | 7/1998 | Mikol et al. |
| 5,776,204 A | 7/1998 | Noble et al. |
| 5,779,703 A | 7/1998 | Benoist |
| 5,779,705 A | 7/1998 | Matthews |
| 5,782,921 A | 7/1998 | Colleran et al. |
| 5,785,057 A | 7/1998 | Fischer |
| 5,807,241 A | 9/1998 | Heimberger |
| 5,810,750 A | 9/1998 | Buser |
| 5,810,820 A | 9/1998 | Santori et al. |
| 5,810,830 A | 9/1998 | Noble et al. |
| 5,814,047 A | 9/1998 | Emilio et al. |
| 5,814,681 A | 9/1998 | Hino et al. |
| 5,816,812 A | 10/1998 | Kownacki et al. |
| 5,827,282 A | 10/1998 | Pennig |
| 5,829,081 A | 11/1998 | Pearce |
| 5,836,949 A | 11/1998 | Campbell, Jr. et al. |
| 5,849,004 A | 12/1998 | Bramlet |
| 5,849,014 A | 12/1998 | Mastrorio et al. |
| 5,849,035 A | 12/1998 | Pathak et al. |
| 5,855,581 A | 1/1999 | Koblish et al. |
| 5,863,295 A | 1/1999 | Averill et al. |
| 5,879,352 A | 3/1999 | Filoso et al. |
| 5,881,878 A | 3/1999 | Faccioli et al. |
| 5,882,351 A | 3/1999 | Fox |
| 5,893,850 A | 4/1999 | Cachia |
| 5,895,390 A | 4/1999 | Moran et al. |
| 5,897,560 A | 4/1999 | Johnson |
| 5,902,302 A | 5/1999 | Berki et al. |
| 5,908,422 A | 6/1999 | Bresina |
| 5,908,423 A | 6/1999 | Kashuba et al. |
| 5,912,410 A | 6/1999 | Cordell |
| 5,913,867 A | 6/1999 | Dion |
| 5,919,194 A | 7/1999 | Anderson |
| 5,925,048 A | 7/1999 | Ahmad et al. |
| 5,928,235 A | 7/1999 | Friedl |
| 5,928,240 A | 7/1999 | Johnson |
| 5,928,259 A | 7/1999 | Tovey |
| 5,931,830 A | 8/1999 | Jacobsen et al. |
| 5,931,839 A | 8/1999 | Medoff |
| 5,948,000 A | 9/1999 | Larsen et al. |
| 5,948,001 A | 9/1999 | Larsen |
| 5,951,556 A | 9/1999 | Faccioli et al. |
| 5,951,557 A | 9/1999 | Luter |
| 5,954,722 A | 9/1999 | Bono |
| 5,954,728 A | 9/1999 | Heller et al. |
| 5,964,770 A | 10/1999 | Flomenblit et al. |
| 5,968,047 A | 10/1999 | Reed |
| 5,976,134 A | 11/1999 | Huebner |
| 5,976,147 A | 11/1999 | LaSalle et al. |
| 5,976,188 A | 11/1999 | Dextradeur et al. |
| 5,989,260 A | 11/1999 | Yao |
| 5,989,261 A | 11/1999 | Walker et al. |
| 5,993,459 A | 11/1999 | Larsen et al. |
| 6,004,348 A | 12/1999 | Banas et al. |
| 6,010,505 A | 1/2000 | Asche et al. |
| 6,010,506 A | 1/2000 | Gosney et al. |
| 6,013,081 A | 1/2000 | Burkinshaw et al. |
| 6,015,413 A | 1/2000 | Faccioli et al. |
| 6,017,350 A | 1/2000 | Long |
| 6,019,761 A | 2/2000 | Gustilo |
| 6,019,762 A | 2/2000 | Cole |
| 6,024,745 A | 2/2000 | Faccioli et al. |
| 6,027,506 A | 2/2000 | Faccioli et al. |
| 6,027,534 A | 2/2000 | Wack et al. |
| 6,033,407 A | 3/2000 | Behrens |
| 6,039,742 A | 3/2000 | Krettek et al. |
| 6,045,556 A | 4/2000 | Cohen |
| 6,053,922 A | 4/2000 | Krause et al. |
| 6,056,756 A | 5/2000 | Eng et al. |
| 6,077,264 A | 6/2000 | Chemello |
| 6,080,159 A | 6/2000 | Vichard |
| 6,093,209 A | 7/2000 | Sanders |
| 6,096,040 A | 8/2000 | Esser |
| 6,102,911 A | 8/2000 | Faccioli et al. |
| 6,106,528 A | 8/2000 | Durham et al. |
| 6,120,504 A | 9/2000 | Brumback et al. |
| 6,120,509 A | 9/2000 | Wheeler |
| 6,123,113 A * | 9/2000 | Pontbriand et al. ............ 138/121 |
| 6,126,661 A | 10/2000 | Faccioli et al. |
| 6,126,691 A | 10/2000 | Kasra et al. |
| 6,127,597 A | 10/2000 | Beyar et al. |
| 6,129,756 A | 10/2000 | Kugler et al. |
| 6,129,762 A | 10/2000 | Li |
| 6,139,583 A | 10/2000 | Johnson |
| 6,143,012 A | 11/2000 | Gausepohl |
| 6,143,033 A | 11/2000 | Paul et al. |
| 6,162,223 A | 12/2000 | Orsak et al. |
| 6,162,226 A | 12/2000 | DeCarlo et al. |
| 6,168,632 B1 | 1/2001 | Moser et al. |
| 6,171,309 B1 | 1/2001 | Huebner |
| 6,176,871 B1 | 1/2001 | Pathak et al. |

| | | |
|---|---|---|
| 6,179,839 B1 | 1/2001 | Weiss et al. |
| 6,179,842 B1 | 1/2001 | Spotorno et al. |
| 6,197,029 B1 | 3/2001 | Fujimori et al. |
| 6,197,031 B1 | 3/2001 | Barrette et al. |
| 6,200,321 B1 | 3/2001 | Orbay et al. |
| 6,206,880 B1 | 3/2001 | Karladani |
| 6,221,036 B1 | 4/2001 | Lucas |
| 6,221,074 B1 | 4/2001 | Cole et al. |
| 6,224,600 B1 | 5/2001 | Protogirou |
| 6,224,609 B1 | 5/2001 | Ressemann et al. |
| 6,228,123 B1 | 5/2001 | Dezzani |
| 6,231,576 B1 | 5/2001 | Frigg et al. |
| 6,235,029 B1 | 5/2001 | Faccioli et al. |
| 6,261,289 B1 | 7/2001 | Levy |
| 6,270,499 B1 | 8/2001 | Leu et al. |
| 6,273,876 B1 | 8/2001 | Klima et al. |
| 6,273,892 B1 | 8/2001 | Orbay et al. |
| 6,280,474 B1 | 8/2001 | Cassidy et al. |
| 6,283,969 B1 | 9/2001 | Grusin et al. |
| 6,287,310 B1 | 9/2001 | Fox |
| 6,290,725 B1 | 9/2001 | Weiss et al. |
| 6,296,603 B1 | 10/2001 | Turnlund et al. |
| 6,296,645 B1 | 10/2001 | Hover et al. |
| 6,299,642 B1 | 10/2001 | Chan |
| 6,319,253 B1 | 11/2001 | Ackeret et al. |
| 6,332,886 B1 | 12/2001 | Green et al. |
| 6,336,929 B1 | 1/2002 | Justin |
| 6,348,053 B1 | 2/2002 | Cachia |
| 6,355,042 B2 | 3/2002 | Winquist et al. |
| 6,355,069 B1 | 3/2002 | DeCarlo et al. |
| 6,358,250 B1 | 3/2002 | Orbay |
| 6,358,283 B1 | 3/2002 | Hogfors et al. |
| 6,364,824 B1 | 4/2002 | Fitzsimmons |
| 6,364,882 B1 | 4/2002 | Orbay |
| 6,379,359 B1 | 4/2002 | Dahners |
| 6,379,360 B1 | 4/2002 | Ackeret et al. |
| 6,395,004 B1 | 5/2002 | Dye et al. |
| 6,402,753 B1 | 6/2002 | Cole et al. |
| 6,406,477 B1 | 6/2002 | Fujiwara |
| 6,416,516 B1 | 7/2002 | Stauch et al. |
| 6,423,096 B1 | 7/2002 | Musset et al. |
| 6,425,923 B1 | 7/2002 | Stalcup et al. |
| 6,436,148 B1 | 8/2002 | DeCarlo et al. |
| 6,440,135 B2 | 8/2002 | Orbay et al. |
| 6,443,954 B1 | 9/2002 | Bramlet et al. |
| 6,443,992 B2 | 9/2002 | Lubinus |
| 6,447,513 B1 | 9/2002 | Griggs |
| 6,447,514 B1 | 9/2002 | Stalcup et al. |
| 6,447,515 B1 | 9/2002 | Meldrum |
| 6,447,518 B1 | 9/2002 | Krause et al. |
| 6,461,358 B1 | 10/2002 | Faccioli |
| 6,461,360 B1 | 10/2002 | Adam |
| 6,468,278 B1 | 10/2002 | Muckter |
| 6,488,684 B2 | 12/2002 | Bramlet et al. |
| 6,491,694 B1 | 12/2002 | Orsak |
| 6,500,209 B1 | 12/2002 | Kolb |
| 6,508,819 B1 | 1/2003 | Orbay |
| 6,508,820 B2 | 1/2003 | Bales |
| 6,511,481 B2 | 1/2003 | von Hoffmann et al. |
| 6,520,994 B2 | 2/2003 | Nogarin |
| 6,524,313 B1 | 2/2003 | Fassier et al. |
| 6,527,775 B1 | 3/2003 | Warburton |
| 6,530,925 B2 | 3/2003 | Boudard et al. |
| 6,533,788 B1 | 3/2003 | Orbay |
| 6,537,275 B2 | 3/2003 | Venturini et al. |
| 6,540,752 B1 | 4/2003 | Hicken et al. |
| 6,551,321 B1 | 4/2003 | Burkinshaw et al. |
| 6,554,833 B2 | 4/2003 | Levy et al. |
| 6,554,862 B2 | 4/2003 | Hays et al. |
| 6,558,388 B1 | 5/2003 | Bartsch et al. |
| 6,562,042 B2 | 5/2003 | Nelson |
| 6,565,573 B1 | 5/2003 | Ferrante et al. |
| 6,572,620 B1 | 6/2003 | Schon et al. |
| 6,575,973 B1 | 6/2003 | Shekalim |
| 6,575,986 B2 | 6/2003 | Overaker |
| 6,575,994 B1 | 6/2003 | Marin et al. |
| 6,582,453 B1 | 6/2003 | Tran et al. |
| 6,607,531 B2 | 8/2003 | Frigg |
| 6,613,052 B1 | 9/2003 | Kinnett |
| 6,616,742 B2 | 9/2003 | Lin et al. |
| 6,620,197 B2 | 9/2003 | Maroney et al. |
| 6,623,487 B1 | 9/2003 | Goshert |
| 6,629,976 B1 | 10/2003 | Gnos et al. |
| 6,632,224 B2 | 10/2003 | Cachia et al. |
| 6,641,596 B1 | 11/2003 | Lizardi |
| 6,648,889 B2 | 11/2003 | Bramlet et al. |
| 6,648,890 B2 | 11/2003 | Culbert et al. |
| 6,652,529 B2 | 11/2003 | Swanson |
| 6,652,591 B2 | 11/2003 | Serbousek et al. |
| 6,656,189 B1 | 12/2003 | Wilson et al. |
| 6,682,568 B2 | 1/2004 | Despres, III et al. |
| 6,685,679 B2 | 2/2004 | Merdan |
| 6,685,706 B2 | 2/2004 | Padget et al. |
| 6,688,822 B2 | 2/2004 | Ritter et al. |
| 6,695,844 B2 | 2/2004 | Bramlet et al. |
| 6,699,251 B1 | 3/2004 | Venturini |
| 6,699,253 B2 | 3/2004 | McDowell et al. |
| 6,706,046 B2 | 3/2004 | Orbay et al. |
| 6,706,072 B2 | 3/2004 | Dwyer et al. |
| 6,709,436 B1 | 3/2004 | Hover et al. |
| 6,712,820 B2 | 3/2004 | Orbay |
| 6,722,368 B1 | 4/2004 | Shaikh |
| 6,723,129 B2 | 4/2004 | Dwyer et al. |
| 6,730,087 B1 | 5/2004 | Butsch |
| 6,730,090 B2 | 5/2004 | Orbay et al. |
| 6,736,818 B2 | 5/2004 | Perren et al. |
| 6,749,611 B2 | 6/2004 | Venturini et al. |
| 6,755,831 B2 | 6/2004 | Putnam et al. |
| 6,755,862 B2 | 6/2004 | Keynan |
| 6,755,866 B2 | 6/2004 | Southworth |
| 6,767,350 B1 | 7/2004 | Lob |
| 6,767,351 B2 | 7/2004 | Orbay et al. |
| 6,780,185 B2 | 8/2004 | Frei et al. |
| 6,783,529 B2 | 8/2004 | Hover et al. |
| 6,783,530 B1 | 8/2004 | Levy |
| 6,783,533 B2 | 8/2004 | Green et al. |
| 6,786,908 B2 | 9/2004 | Hover et al. |
| 6,793,655 B2 | 9/2004 | Orsak |
| 6,793,659 B2 | 9/2004 | Putnam |
| 6,808,527 B2 | 10/2004 | Lower et al. |
| 6,821,299 B2 | 11/2004 | Kirking et al. |
| 6,827,739 B2 | 12/2004 | Griner et al. |
| 6,827,741 B2 | 12/2004 | Reeder |
| 6,840,939 B2 | 1/2005 | Venturini et al. |
| 6,855,146 B2 | 2/2005 | Frigg et al. |
| 6,855,167 B2 | 2/2005 | Shimp et al. |
| 6,863,692 B2 | 3/2005 | Meulink |
| 6,866,455 B2 | 3/2005 | Hasler |
| 6,866,665 B2 | 3/2005 | Orbay |
| 6,887,243 B2 | 5/2005 | Culbert |
| 6,887,271 B2 | 5/2005 | Justin et al. |
| 6,890,333 B2 | 5/2005 | von Hoffmann et al. |
| 6,893,444 B2 | 5/2005 | Orbay |
| 6,908,465 B2 | 6/2005 | von Hoffmann et al. |
| 6,921,397 B2 | 7/2005 | Corcoran et al. |
| 6,926,720 B2 | 8/2005 | Castaneda |
| 6,926,741 B2 | 8/2005 | Kolb |
| 6,929,692 B2 | 8/2005 | Tas |
| 6,942,666 B2 | 9/2005 | Overaker et al. |
| 6,942,668 B2 | 9/2005 | Padget et al. |
| 6,949,100 B1 | 9/2005 | Venturini |
| 6,949,124 B2 | 9/2005 | Serbousek et al. |
| 6,951,561 B2 | 10/2005 | Warren et al. |
| 6,974,482 B2 | 12/2005 | Zhu |
| 6,986,771 B2 | 1/2006 | Paul et al. |
| 7,001,388 B2 | 2/2006 | Orbay et al. |
| D518,174 S | 3/2006 | Venturini et al. |
| 7,008,425 B2 | 3/2006 | Phillips |
| 7,008,428 B2 | 3/2006 | Cachia et al. |
| 7,008,451 B2 | 3/2006 | Justin et al. |
| 7,011,664 B2 | 3/2006 | Haney et al. |
| 7,012,106 B2 | 3/2006 | Yuan et al. |
| 7,029,476 B2 | 4/2006 | Hansson |
| 7,029,478 B2 | 4/2006 | Hollstien et al. |
| 7,033,363 B2 | 4/2006 | Powell |
| 7,033,365 B2 | 4/2006 | Powell et al. |
| 7,041,104 B1 | 5/2006 | Cole et al. |
| 7,044,978 B2 | 5/2006 | Howie et al. |

| | | |
|---|---|---|
| 7,052,498 B2 | 5/2006 | Levy et al. |
| 7,056,322 B2 | 6/2006 | Davison et al. |
| 7,060,075 B2 | 6/2006 | Govari et al. |
| 7,070,601 B2 | 7/2006 | Culbert et al. |
| 7,070,616 B2 | 7/2006 | Majercak et al. |
| 7,074,224 B2 | 7/2006 | Daniels et al. |
| 7,083,624 B2 | 8/2006 | Irving |
| 7,090,676 B2 | 8/2006 | Huebner et al. |
| 7,097,648 B1 | 8/2006 | Globerman et al. |
| 7,097,664 B2 | 8/2006 | Despres, III et al. |
| RE39,301 E | 9/2006 | Bertin |
| 7,101,376 B2 | 9/2006 | Semet |
| 7,118,574 B2 | 10/2006 | Patel et al. |
| 7,122,056 B2 | 10/2006 | Dwyer et al. |
| 7,137,987 B2 | 11/2006 | Patterson et al. |
| 7,141,052 B2 | 11/2006 | Manderson |
| 7,141,067 B2 | 11/2006 | Jones et al. |
| 7,144,399 B2 | 12/2006 | Hayes et al. |
| 7,147,639 B2 | 12/2006 | Berki et al. |
| 7,147,640 B2 | 12/2006 | Huebner et al. |
| 7,153,309 B2 | 12/2006 | Huebner et al. |
| 7,156,852 B2 | 1/2007 | Dye et al. |
| 7,160,302 B2 | 1/2007 | Warburton |
| 7,160,333 B2 | 1/2007 | Plouhar et al. |
| 7,163,563 B2 | 1/2007 | Schwartz et al. |
| 7,175,625 B2 | 2/2007 | Culbert |
| 7,175,631 B2 | 2/2007 | Wilson et al. |
| 7,179,260 B2 | 2/2007 | Gerlach et al. |
| 7,188,687 B2 | 3/2007 | Rudd et al. |
| 7,189,237 B2 | 3/2007 | Huebner |
| 7,625,364 B2 * | 12/2009 | Corcoran et al. ............ 604/523 |
| 7,632,277 B2 | 12/2009 | Woll et al. |
| 7,846,162 B2 | 12/2010 | Nelson et al. |
| 7,909,825 B2 | 3/2011 | Saravia et al. |
| 7,914,533 B2 | 3/2011 | Nelson et al. |
| 7,942,875 B2 | 5/2011 | Nelson et al. |
| 2001/0034526 A1 | 10/2001 | Kuslich et al. |
| 2002/0161369 A1 | 10/2002 | Bramlet et al. |
| 2002/0188297 A1 | 12/2002 | Dakin et al. |
| 2003/0040752 A1 | 2/2003 | Kitchens |
| 2003/0045919 A1 | 3/2003 | Swoyer et al. |
| 2003/0236529 A1 | 12/2003 | Shluzas et al. |
| 2004/0133204 A1 | 7/2004 | Davies |
| 2004/0213825 A1 | 10/2004 | Levy |
| 2004/0214311 A1 | 10/2004 | Levy |
| 2004/0230193 A1 | 11/2004 | Cheung et al. |
| 2004/0236327 A1 | 11/2004 | Paul et al. |
| 2005/0015154 A1 | 1/2005 | Lindsey et al. |
| 2005/0027294 A1 | 2/2005 | Woll et al. |
| 2005/0027301 A1 | 2/2005 | Stihl |
| 2005/0047892 A1 | 3/2005 | Bremner |
| 2005/0080425 A1 | 4/2005 | Bhatnagar et al. |
| 2005/0159749 A1 | 7/2005 | Levy et al. |
| 2005/0165395 A1 | 7/2005 | Orbay et al. |
| 2005/0177158 A1 | 8/2005 | Doubler et al. |
| 2005/0216007 A1 | 9/2005 | Woll et al. |
| 2005/0228391 A1 | 10/2005 | Levy et al. |
| 2005/0261781 A1 | 11/2005 | Sennett et al. |
| 2005/0267481 A1 | 12/2005 | Carl et al. |
| 2006/0015101 A1 | 1/2006 | Warburton et al. |
| 2006/0015123 A1 | 1/2006 | Fencl et al. |
| 2006/0036248 A1 | 2/2006 | Ferrante |
| 2006/0064094 A1 | 3/2006 | Levy et al. |
| 2006/0084998 A1 | 4/2006 | Levy et al. |
| 2006/0200143 A1 | 9/2006 | Warburton |
| 2006/0200144 A1 | 9/2006 | Warburton |
| 2006/0229617 A1 | 10/2006 | Meller et al. |
| 2006/0247638 A1 | 11/2006 | Trieu et al. |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2007/0142916 A1 | 6/2007 | Olson et al. |
| 2007/0233105 A1 | 10/2007 | Nelson et al. |
| 2008/0132896 A1 | 6/2008 | Bowen et al. |
| 2008/0140078 A1 | 6/2008 | Nelson et al. |
| 2008/0149115 A1 | 6/2008 | Hauck et al. |
| 2008/0161805 A1 | 7/2008 | Saravia et al. |
| 2008/0221620 A1 | 9/2008 | Krause |
| 2008/0255560 A1 | 10/2008 | Myers et al. |
| 2008/0262495 A1 | 10/2008 | Coati et al. |
| 2008/0287951 A1 * | 11/2008 | Stoneburner et al. ........... 606/63 |
| 2009/0018542 A1 | 1/2009 | Saravia et al. |
| 2009/0228007 A1 | 9/2009 | Justin et al. |
| 2009/0228008 A1 | 9/2009 | Justin et al. |
| 2010/0094347 A1 | 4/2010 | Nelson et al. |
| 2011/0087227 A1 | 4/2011 | Mazur et al. |
| 2011/0144645 A1 | 6/2011 | Saravia et al. |
| 2011/0282346 A1 | 11/2011 | Pham et al. |

FOREIGN PATENT DOCUMENTS

| | | |
|---|---|---|
| CA | 2561552 A1 | 11/2005 |
| EP | 1582163 A1 | 11/2003 |
| EP | 1815813 A2 | 8/2007 |
| WO | WO 97/18769 A1 | 5/1997 |
| WO | WO 98/27876 A1 | 7/1998 |
| WO | WO 98/56301 A1 | 12/1998 |
| WO | WO 99/20195 A1 | 4/1999 |
| WO | WO 00/28906 A1 | 5/2000 |
| WO | WO 01/28443 A1 | 4/2001 |
| WO | WO 02/00270 A1 | 1/2002 |
| WO | WO 02/00275 A1 | 1/2002 |
| WO | WO 02/02158 A1 | 1/2002 |
| WO | WO 2005/112804 A1 | 12/2005 |
| WO | WO 2006/053210 A1 | 5/2006 |
| WO | WO 2006/124764 A1 | 11/2006 |

OTHER PUBLICATIONS

Nelson et al.; U.S. Appl. No. 12/482,388 entitled "Fracture fixation device, tools and methods," filed Jun. 10, 2009. Nelson et al.; U.S. Appl. No. 12/482,395 entitled "Fracture fixation device, tools and methods," filed Jun. 10, 2009.
The Titanium Flexible Humeral Nail System (Quick reference for surgical technique), Synthes, 1999.
The Titanium Flexible Humeral Nail System (Technique Guide), Synthes, 1999.
Andermahr et al., "Anatomy of the clavicle and the intramedullary nailing of midclavicular fractures," Clinical Anatomy; vol. 20; pp. 48-56; 2007.
US 6,030,385, 02/2000, Faccioli et al. (withdrawn)

* cited by examiner

*Primary Examiner* — Jan Christopher Merene
(74) *Attorney, Agent, or Firm* — Knobbe Martens Olson & Bear, LLP

(57) ABSTRACT

A bone fixation device is provided with an elongate body having a longitudinal axis and having a first state in which at least a portion of the body is flexible and a second state in which the body is generally rigid, an actuatable gripper disposed at a distal location on the elongated body, a hub located on a proximal end of the elongated body, and an actuator operably connected to the gripper to deploy the gripper from a retracted configuration to an expanded configuration. Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone. Various configurations are disclosed for allowing a device body to change shape as it moves from a flexible state to a rigid state.

29 Claims, 35 Drawing Sheets

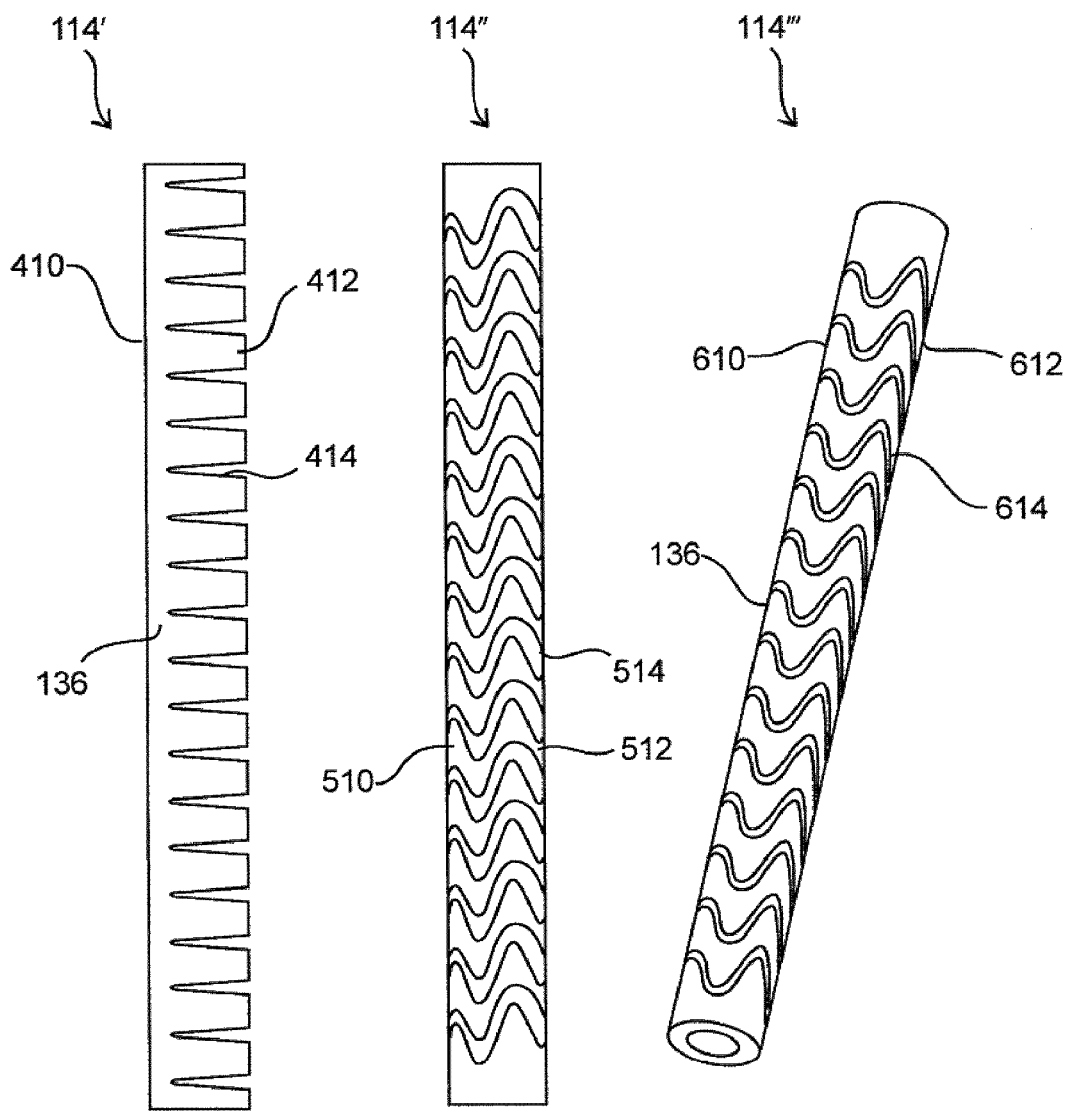

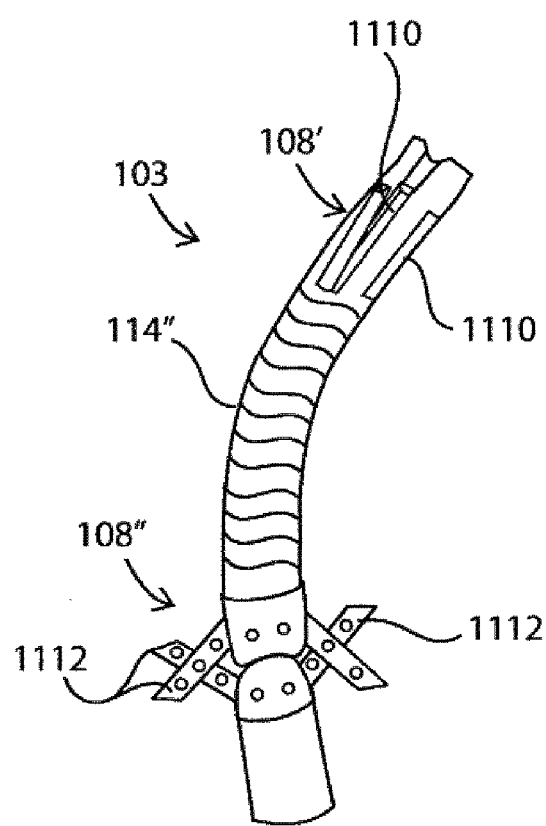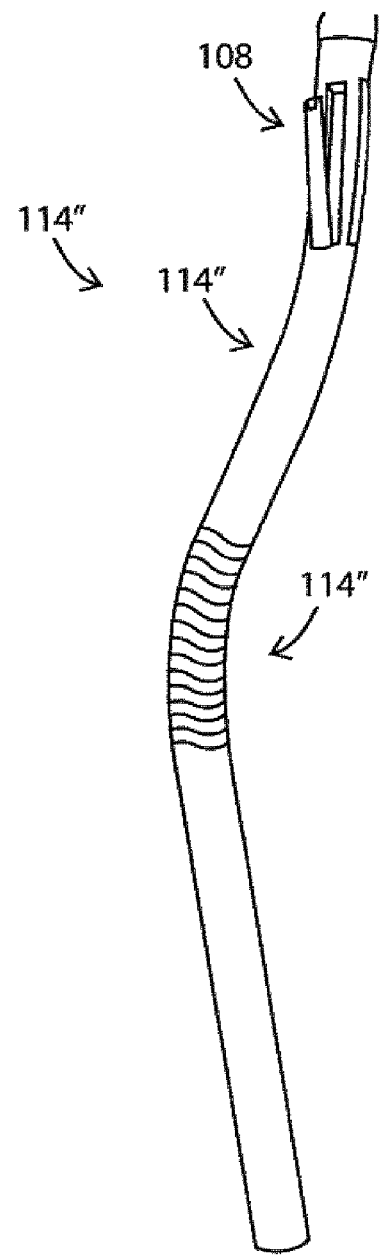
FIG. 11
FIG. 12

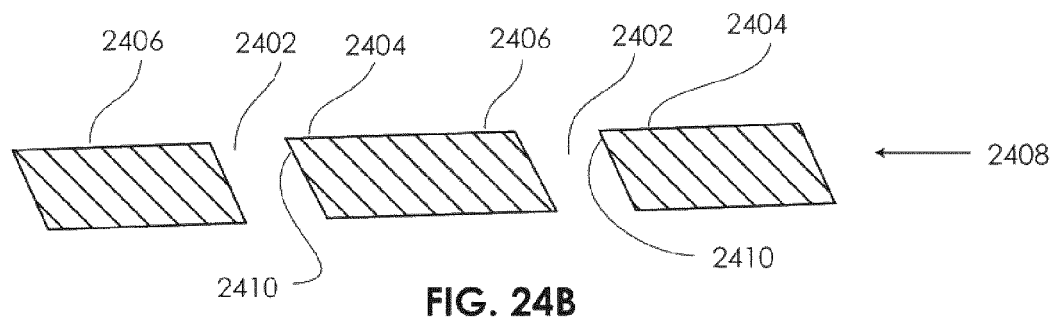
FIG. 24B
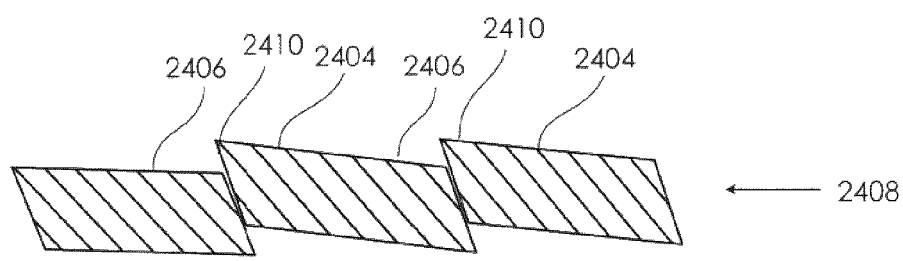
FIG. 24C
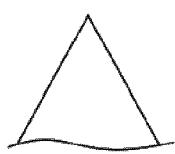 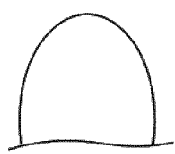 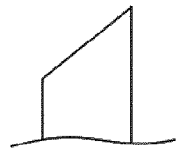 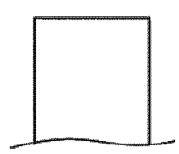 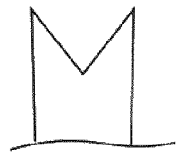
FIG. 24D    FIG. 24E    FIG. 24F    FIG. 24G    FIG. 24H

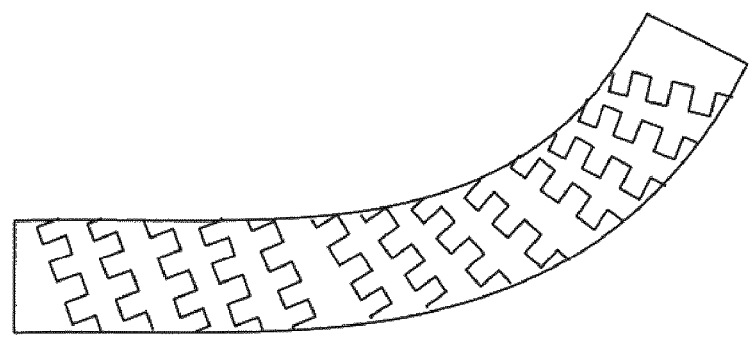
FIG. 26B
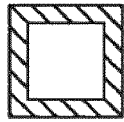
FIG. 26C
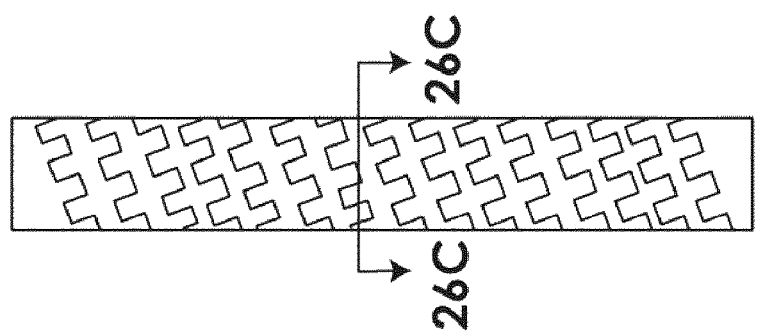
FIG. 26A
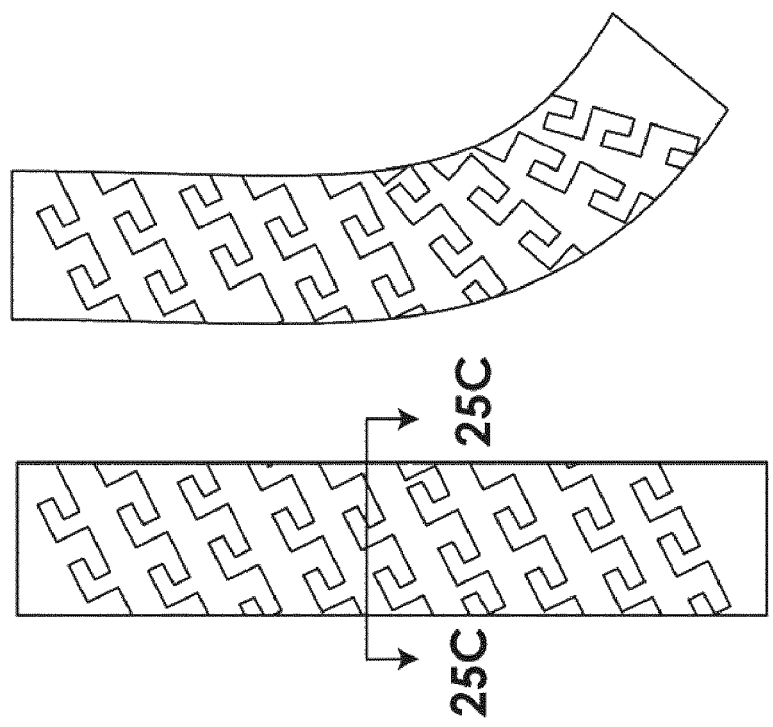
FIG. 25B
FIG. 25C
FIG. 25A

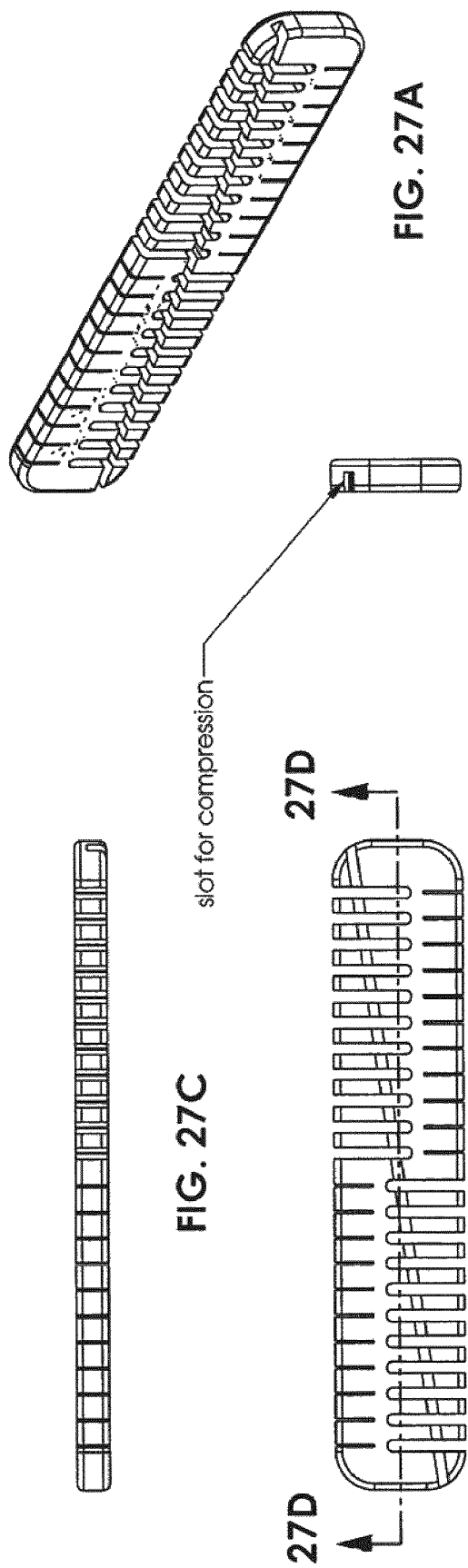

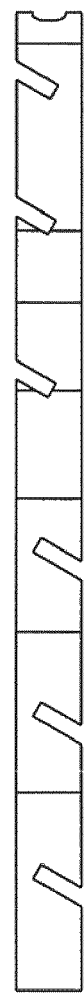
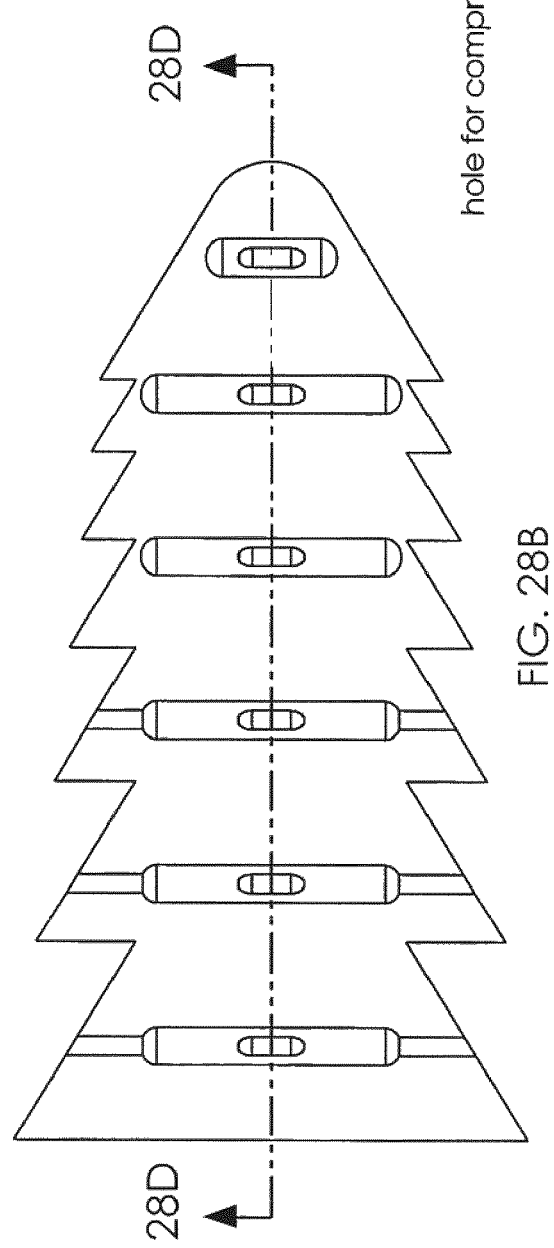
FIG. 28C
FIG. 28B
FIG. 28D
FIG. 28E
hole for compression

FRACTURE FIXATION DEVICE, TOOLS AND METHODS

CROSS-REFERENCE TO RELATED APPLICATIONS

This application is a Continuation-in-Part of U.S. application Ser. No. 11/383,269, titled "MINIMALLY INVASIVE ACTUABLE BONE FIXATION DEVICES", filed May 15, 2006 now U.S. Pat. No. 7,846,162 which claims priority to U.S. Provisional Application No. 60/682,652, titled "METHOD AND SYSTEM FOR PROVIDING REINFORCEMENT OF BONES", filed May 18, 2005. This application is also a Continuation-in-part of U.S. application Ser. No. 11/383,800 filed May 17, 2006 now abandoned titled "DEPLOYABLE INTRAMEDULLARY STENT SYSTEM FOR REINFORCEMENT OF BONE" which claims priority to U.S. Provisional Application No. 60/682,652, titled "METHOD AND SYSTEM FOR PROVIDING REINFORCEMENT OF BONES", filed May 18, 2005. This application is also a Continuation-in-Part of U.S. application Ser. No. 11/944,366, titled "FRACTURE FIXATION DEVICE, TOOLS AND METHODS", filed Nov. 21, 2007 now U.S. Pat. No. 7,909,825 which claims priority to U.S. provisional applications: No. 60/867,011, titled "BONE REPAIR IMPLANT WITH CENTRAL RATCHETING GUIDEWIRE", filed Nov. 22, 2006; No. 60/866,976, titled "SURGICAL TOOLS FOR USE IN DEPLOYING BONE REPAIR DEVICES," filed Nov. 22, 2006; and No. 60/949,071, titled "FRACTURE FIXATION DEVICE, TOOLS AND METHODS", filed Jul. 11, 2007.

This application claims priority of U.S. Provisional Application No. 61/060,440, titled "FRACTURE FIXATION DEVICE, TOOLS AND METHODS" filed Jun. 10, 2008; U.S. Provisional Application No. 61/060,445, titled "FRACTURE FIXATION DEVICE, TOOLS AND METHODS" filed Jun. 10, 2008; U.S. Provisional Application No. 61/060,450, titled "FRACTURE FIXATION DEVICE, TOOLS AND METHODS" filed Jun. 10, 2008; U.S. Provisional Application No. 61/100,635, titled "FRACTURE FIXATION DEVICE, TOOLS AND METHODS" filed Sep. 26, 2008; U.S. Provisional Application No. 61/100,652, titled "FRACTURE FIXATION DEVICE, TOOLS AND METHODS" filed Sep. 26, 2008; U.S. Provisional Application No. 61/122,563, titled "BONE FIXATION DEVICE, TOOLS AND METHODS" filed Dec. 15, 2008; U.S. Provisional Application No. 61/138,920, titled "BONE FIXATION DEVICE, TOOLS AND METHODS" filed Dec. 18, 2008; and U.S. Provisional Application No. 61/117,901, titled "BONE FRACTURE FIXATION SCREWS, SYSTEMS AND METHODS OF USE" filed Nov. 25, 2008.

INCORPORATION BY REFERENCE

All publications and patent applications mentioned in this specification are herein incorporated by reference to the same extent as if each individual publication or patent application was specifically and individually indicated to be incorporated by reference

BACKGROUND OF THE INVENTION

The present invention relates to devices, tools and methods for providing reinforcement of bones. More specifically, the present invention relates to devices, tools and methods for providing reconstruction and reinforcement of bones, including diseased, osteoporotic and fractured bones. The number and diversity sports and work related fractures are being driven by several sociological factors. The diversity of high energy sports has increased and the participation in these sports has followed the general trend of affluence and the resultant amount of time for leisure. High energy sports include skiing, motorcycle riding, snow mobile riding, snowboarding, mountain biking, road biking, kayaking, and all terrain vehicle (ATV) riding. As the general affluence of the economically developed countries has increased the amount and age of people participating in these activities has increased. Lastly, the acceptance and ubiquitous application of passive restraint systems, airbags, in automobiles has created greater numbers of non-life threatening fractures. In the past, a person that might expire from a serious automobile accident, now survives with multiple traumas and resultant fractures.

Bone fractures are a common medical condition both in the young and old segments of the population. However, with an increasingly aging population, osteoporosis has become more of a significant medical concern in part due to the risk of osteoporotic fractures. Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass, leading to fractures in more than 300,000 people over the age of 65. In 1997 the estimated cost for osteoporosis related fractures was $13 billion. That figure increased to $17 billion in 2002 and is projected to increase to $210-240 billion by 2040. Currently it is expected that one in two women, and one in four men, over the age of 50 will suffer an osteoporosis-related fracture. Osteoporosis is the most important underlying cause of fracture in the elderly. Also, sports and work-related accidents account for a significant number of bone fractures seen in emergency rooms among all age groups.

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (IM) rod or nail is used to align and stabilize the fracture. In that instance, a metal rod is placed inside a canal of a bone and fixed in place, typically at both ends. See, for example, Fixion® IM(Nail), www.disc-o-tech.com. Placement of conventional IM rods are typically a "line of sight" and require access collinear with the center line of the IM canal. Invariably, this line of sight access violates, disrupts, and causes damage to important soft tissue structures such as ligaments, tendons, cartilage, facia, and epidermis This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, and or when the nail is not removed, a long term implant of the IM nail. The outer diameter of the IM nail must be selected for the minimum inside diameter of the space. Therefore, portions of the IM nail may not be in contact with the canal. Further, micromotion between the bone and the IM nail may cause pain or necrosis of the bone. In still other cases, infection can occur.

The IM nail may be removed after the fracture has healed. This requires a subsequent surgery with all of the complications and risks of a later intrusive procedure. In general, rigid IM rods or nails are difficult to insert, can damage the bone and require additional incisions for cross-screws to attach the rods or nails to the bone.

Some IM nails are inflatable. See, for example, Meta-Fix IM Nailing System, www.disc-o-tech.com. Such IM nails require inflating the rod with very high pressures, endangering the surrounding bone. Inflatable nails have many of the same drawbacks as the rigid IM nails described above.

External fixation is another technique employed to repair fractures. In this approach, a rod may traverse the fracture site outside of the epidermis. The rod is attached to the bone with trans-dermal screws. If external fixation is used, the patient will have multiple incisions, screws, and trans-dermal infection paths. Furthermore, the external fixation is cosmetically intrusive, bulky, and prone to painful inadvertent manipulation by environmental conditions such as, for example, bumping into objects and laying on the device.

Other concepts relating to bone repair are disclosed in, for example, U.S. Pat. Nos. 5,108,404 to Scholten for Surgical Protocol for Fixation of Bone Using Inflatable Device; 4,453, 539 to Raftopoulos et al. for Expandable Intramedullary Nail for the Fixation of Bone Fractures; 4,854,312 to Raftopolous for Expanding Nail; 4,932,969 to Frey et al. for Joint Endoprosthesis; 5,571,189 to Kuslich for Expandable Fabric Implant for Stabilizing the Spinal Motion Segment; 4,522, 200 to Stednitz for Adjustable Rod; 4,204,531 to Aginsky for Nail with Expanding Mechanism; 5,480,400 to Berger for Method and Device for Internal Fixation of Bone Fractures; 5,102,413 to Poddar for Inflatable Bone Fixation Device; 5,303,718 to Krajicek for Method and Device for the Osteosynthesis of Bones; 6,358,283 to Hogfors et al. for Implantable Device for Lengthening and Correcting Malpositions of Skeletal Bones; 6,127,597 to Beyar et al. for Systems for Percutaneous Bone and Spinal Stabilization, Fixation and Repair; 6,527,775 to Warburton for Interlocking Fixation Device for the Distal Radius; U.S. Patent Publication US2006/0084998 A1 to Levy et al. for Expandable Orthopedic Device; and PCT Publication WO 2005/112804 A1 to Myers Surgical Solutions, LLC et. al. for Fracture Fixation and Site Stabilization System. Other fracture fixation devices, and tools for deploying fracture fixation devices, have been described in: US Patent Appl. Publ. No. 2006/0254950; U.S. Ser. No. 60/867,011 (filed Nov. 22, 2006); U.S. Ser. No. 60/866,976 (filed Nov. 22, 2006); and U.S. Ser. No. 60/866, 920 (filed Nov. 22, 2006).

In view of the foregoing, it would be desirable to have a device, system and method for providing effective and minimally invasive bone reinforcement and fracture fixation to treat fractured or diseased bones, while improving the ease of insertion, eliminating cross-screw incisions and minimizing trauma.

SUMMARY OF THE INVENTION

Aspects of the invention relate to embodiments of a bone fixation device and to methods for using such a device for repairing a bone fracture. The bone fixation device may include an elongate body with a longitudinal axis and having a flexible state and a rigid state. The device further may include a plurality of grippers disposed at longitudinally-spaced locations along the elongated body, a rigid hub connected to the elongated body, and an actuator that is operably-connected to the grippers to deploy the grippers from a first shape to an expanded second shape. The elongate body and the rigid hub may or may not be collinear or parallel.

In one embodiment, a bone fixation device is provided with an elongate body having a longitudinal axis and having a first state in which at least a portion of the body is flexible and a second state in which the body is generally rigid, an actuatable gripper disposed at a distal location on the elongated body, a hub located on a proximal end of the elongated body, and an actuator operably connected to the gripper to deploy the gripper from a retracted configuration to an expanded configuration.

Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone.

According to aspects of the present disclosure, similar methods involve repairing a fracture of a metatarsal, metacarpal, sternum, tibia, rib, midshaft radius, ulna, olecranon (elbow), huberus, or distal fibula. Each of these bones have a distal and proximal segment, farthest and closest to the heart, respectively, and on opposite ends of a fracture. The method comprises creating an intramedullary channel, such that the channel traverses the fracture of the bone and comprises at least one segment that substantially follows a curved anatomical contour of the bone; and inserting a bone fixation device into the intramedullary channel and across the fracture of the bone, such that at least a portion of an elongate body of the fixation device in a flexible state is placed within the curved segment of the channel.

One embodiment of the present invention provides a low weight to volume mechanical support for fixation, reinforcement and reconstruction of bone or other regions of the musculo-skeletal system in both humans and animals. The method of delivery of the device is another aspect of the invention. The method of delivery of the device in accordance with the various embodiments of the invention reduces the trauma created during surgery, decreasing the risks associated with infection and thereby decreasing the recuperation time of the patient. The framework may in one embodiment include an expandable and contractible structure to permit re-placement and removal of the reinforcement structure or framework.

In accordance with the various embodiments of the present invention, the mechanical supporting framework or device may be made from a variety of materials such as metal, composite, plastic or amorphous materials, which include, but are not limited to, steel, stainless steel, cobalt chromium plated steel, titanium, nickel titanium alloy (nitinol), super-elastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials.

Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In still another embodiment of the invention, a method of repairing a bone fracture is disclosed that comprises: accessing a fracture along a length of a bone through a bony protuberance at an access point at an end of a bone; advancing a bone fixation device into a space through the access point at the end of the bone; bending a portion of the bone fixation device along its length to traverse the fracture; and locking the bone fixation device into place within the space of the bone. The method can also include the step of advancing an obturator through the bony protuberance and across the fracture prior to advancing the bone fixation device into the space. In yet another embodiment of the method, the step of anchoring the bone fixation device within the space can be included. In another embodiment of the invention, a method of repairing bone is disclosed whereby the area of the affected bone is remediated by advancing the device through an opening in the middle of the bone, below the metaphysis or at a point away from a joint or bony protuberance.

An aspect of the invention discloses a removable bone fixation device that uses a single port of insertion and has a single-end of remote actuation wherein a bone fixation device stabilizes bone after it has traversed the fracture. The bone fixation device is adapted to provide a single end in one area or location where the device initiates interaction with bone. The device can be deployed such that the device interacts with bone. Single portal insertion and single-end remote actuation enables the surgeon to insert and deploy the device, deactivate and remove the device, reduce bone fractures, displace or compress the bone, and lock the device in place. In addition, the single-end actuation enables the device to grip bone, compresses the rigidizable flexible body, permits axial, torsional and angular adjustments to its position during surgery, and releases the device from the bone during its removal procedure. A removable extractor can be provided in some embodiments of the device to enable the device to be placed and extracted by deployment and remote actuation from a single end. The device of the invention can be adapted and configured to provide at least one rigidizable flexible body or sleeve. Further the body can be configured to be flexible in all angles and directions. The flexibility provided is in selective planes and angles in the Cartesian, polar, or cylindrical coordinate systems. Further, in some embodiments, the body is configured to have a remote actuation at a single end. Additionally, the body can be configured to have apertures, windings, etc. The device may be configured to function with non-flexible bodies for use in bones that have a substantially straight segment or curved segments with a constant radius of curvature. Another aspect of the invention includes a bone fixation device in that has mechanical geometry that interacts with bone by a change in the size of at least one dimension of a Cartesian, polar, or spherical coordinate system. Further, in some embodiments, bioabsorbable materials can be used in conjunction with the devices, for example by providing specific subcomponents of the device configured from bioabsorbable materials. A sleeve can be provided in some embodiments where the sleeve is removable, has deployment, remote actuation, and a single end. Where a sleeve is employed, the sleeve can be adapted to provide a deployable interdigitation process or to provide an aperture along its length through which the deployable interdigitation process is adapted to engage bone. In some embodiments, the deployable interdigitation process is further adapted to engage bone when actuated by the sleeve. In some embodiments, the bone fixation device further comprises a cantilever adapted to retain the deployable bone fixation device within the space. The sleeve can further be adapted to be expanded and collapsed within the space by a user. One end of the device can be configured to provide a blunt obturator surface adapted to advance into the bone. A guiding tip may also be provided that facilitates guiding the device through the bone. The device may be hollow and accept a guide wire. The guiding tip may facilitate placement of the device thereby providing a means to remove bone in its path (a helical end, a cutting end, or ablative end). The guiding tip may allow capture, interaction, or insertion into or around a tube on its internal or external surface. Further, the deployable bone fixation device can be adapted to receive external stimulation to provide therapy to the bone. The device can further be adapted to provide an integral stimulator which provides therapy to the bone. In still other embodiments, the device can be adapted to receive deliver therapeutic stimulation to the bone.

The devices disclosed herein may be employed in various regions of the body, including: spinal, cranial, thoracic, lower extremities and upper extremities. Additionally, the devices are suitable for a variety of breaks including, metaphyseal, diaphyseal cortical bone, cancellous bone, and soft tissue such as ligament attachment and cartilage attachment . . . .

The fracture fixation devices of various embodiments of the invention are adapted to be inserted through an opening of a fractured bone, such as the radius (e.g., through a bony protuberance on a distal or proximal end or through the midshaft) into an intramedullary canal of the bone. The device can be inserted in one embodiment in a line of sight manner collinear or nearly collinear, or parallel to the central axis of the intramedullary canal. In another embodiment the device can be inserted at an angle, radius, or tangency to the axis of the intramedullary canal. In another embodiment, the device can be inserted in a manner irrespective of the central axis of the intramedullary canal. In some embodiments, the fixation device has two main components, one configured component for being disposed on the side of the fracture closest to the opening and one component configured for being disposed on the other side of the fracture from the opening so that the fixation device traverses the fracture.

The device components cooperate to align, fix and/or reduce the fracture so as to promote healing. The device may be removed from the bone after insertion (e.g., after the fracture has healed or for other reasons), or it may be left in the bone for an extended period of time or permanently.

In some embodiments, the fracture fixation device has one or more actuatable bone engaging mechanisms such as anchors or grippers on its proximal and/or distal ends. These bone engaging mechanisms may be used to hold the fixation device to the bone while the bone heals. In another embodiment, the fracture fixation device has a plurality of gripper or anchors along its length. In another embodiment, the fracture fixation device has grippers or anchoring devices that interdigitate into the bone at an angle greater than zero degrees and less than 180 degrees to secure the bone segments of the fracture. In another embodiment the fracture fixation device has grippers or anchoring features that when activated from a state that facilitates insertion to a state that captures, aligns, and fixes the fracture, deploy in a geometry so that the resultant fixed bone is analogous, nearly identical, or identical to the geometry of the bone prior to the fracture. In one embodiment of the device, the flexible body allows insertion through tortuous paths within bone or created within bone. Upon activation from the state of insertion to the state of fixation, this device deforms so as to grip the bone upon multiple surfaces of the now collapsed, rigid, flexible body. In this collapsed state the device may be deform in such a way to re-achieve anatomical alignment of the bone. The device as described above can be fabricated so that it can have any cross sectional shape.

In some embodiments, to aid in insertion of the device into the intramedullary canal, the main component of the fracture fixation device has a substantially flexible state. Thereby, the device, prior to activation, may not have a rigid section. Once in place, deployment of the device also causes the components to change from the flexible state to a rigid state to aid in proper fixation of the fracture. At least one of the components may be semi-flexible. Placement of the device may be aided by a detachable rigid member such as a guide or outrigger. Placement of the device may be aided by removable rigid member such as a tube or guide wire. At least one component may provide a bone screw attachment site for the fixation device. At least one of the components of the device may allow a screw or compressive member to be attached along its axis to provide linear compression of one side of the fractured bone towards the other (e.g. compression of the distal segment towards the proximal segment or visa versa). At least one of the components of the device may accept a screw at an acute angle, and angle less than 30 degrees from the axis of the device that would allow compression of one side of the fractured bone towards the other. At least one of the components of the device may accept an alternately removable eyelet to accommodate a compressive device so as to compress one side of the fractured bone towards the other side.

In some embodiments, to aid in insertion into the intramedullary canal, the main component of the fracture fixation device has a substantially flexible state. Thereby, the device, prior to activation, may not have a rigid section. Once in place, deployment of the device also causes the components to change from the flexible state to a rigid state to aid in proper fixation of the fracture. At least one of the components may be semi-flexible. Placement of the device may be aided by a detachable rigid member such as a guide or outrigger. Placement of the device may be aided by a removable rigid member such as a tube or guide wire. At least one component may provide a bone screw attachment site for the fixation device. At least one of the components of the device may allow a screw or compressive member to be attached along its axis to provide linear compression of one side of the fractured bone towards the other (e.g. compression of the distal segment towards the proximal segment or visa versa). At least one of the components of the device may accept a screw at an acute angle, and angle less than 30 degrees from the axis of the device that would allow compression of one side of the fractured bone towards the other. At least one of the components of the device may accept an alternately removable eyelet to accommodate a compressive device so as to compress one side of the fractured bone towards the other side.

Embodiments of the invention also provide deployment tools with a tool guide for precise alignment of one or more bone screws with the fracture fixation device. These embodiments also provide bone screw orientation flexibility so that the clinician can select an orientation for the bone screw(s) that will engage the fixation device as well as any desired bone fragments or other bone or tissue locations.

These and other features and advantages of the present invention will be understood upon consideration of the following detailed description of the invention and the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 is a side view of one embodiment of a shape-conforming flexible-to-rigid body portion.

FIG. 5A is a side view of another embodiment of a shape-conforming flexible-to-rigid body portion.

FIG. 5B is a perspective view of yet another embodiment of a shape-conforming flexible-to-rigid body portion.

FIG. 11 is a side view showing an alternative embodiment device in a deployed, shape-conforming state and having alternative anchors.

FIG. 12 is a side view showing another alternative embodiment device in a deployed, shape-conforming state.

FIGS. 24A-24H are views showing an overlapping flexible-to-rigid body portion, where FIG. 24A is a plan view, FIG. 24B is an enlarged cross-sectional side view of the body portion in an expanded, flexible state, FIG. 24C is an enlarged cross-sectional side view of the body portion in a compressed, rigid state, and FIGS. 24D-24H are enlarged plan views showing various tip configurations.

FIGS. 25A-25C are views showing an exemplary flexible-to-rigid body portion having an oval cross-section, where FIG. 25A is a side view showing the device in a flexible state, FIG. 25B is a side view showing the device in a rigid state, and FIG. 25C is a cross-section taken along line 25C-25C in FIG. 25A.

FIGS. 26A-26C are views showing an exemplary flexible-to-rigid body portion having a square cross-section, where FIG. 26A is a side view showing the device in a flexible state, FIG. 26B is a side view showing the device in a rigid state, and FIG. 26C is a cross-section taken along line 26C-26C in FIG. 26A.

FIGS. 27A-27E show an alternative embodiment of a bone fixation device.

FIGS. 28A-28E show an alternative embodiment of a bone fixation device.

DETAILED DESCRIPTION OF THE INVENTION

By way of background and to provide context for the invention, it may be useful to understand that bone is often described as a specialized connective tissue that serves three major functions anatomically. First, bone provides a mechanical function by providing structure and muscular attachment for movement. Second, bone provides a metabolic function by providing a reserve for calcium and phosphate. Finally, bone provides a protective function by enclosing bone marrow and vital organs. Bones can be categorized as long bones (e.g. radius, femur, tibia and humerus) and flat bones (e.g. skull, scapula and mandible). Each bone type has a different embryological template. Further each bone type contains cortical and trabecular bone in varying proportions. The devices of this invention can be adapted for use in any of the bones of the body as will be appreciated by those skilled in the art.

Cortical bone (compact) forms the shaft, or diaphysis, of long bones and the outer shell of flat bones. The cortical bone provides the main mechanical and protective function. The trabecular bone (cancellous) is found at the end of the long bones, or the epiphysis, and inside the cortex of flat bones. The trabecular bone consists of a network of interconnecting trabecular plates and rods and is the major site of bone remodeling and resorption for mineral homeostasis. During development, the zone of growth between the epiphysis and diaphysis is the metaphysis. Finally, woven bone, which lacks the organized structure of cortical or cancellous bone, is the first bone laid down during fracture repair. Once a bone is fractured, the bone segments are positioned in proximity to each other in a manner that enables woven bone to be laid down on the surface of the fracture. This description of anatomy and physiology is provided in order to facilitate an understanding of the invention. Persons of skill in the art will also appreciate that the scope and nature of the invention is not limited by the anatomy discussion provided. Further, it will be appreciated there can be variations in anatomical characteristics of an individual patient, as a result of a variety of factors, which are not described herein. Further, it will be appreciated there can be variations in anatomical characteristics between bones which are not described herein.

Figure 1:
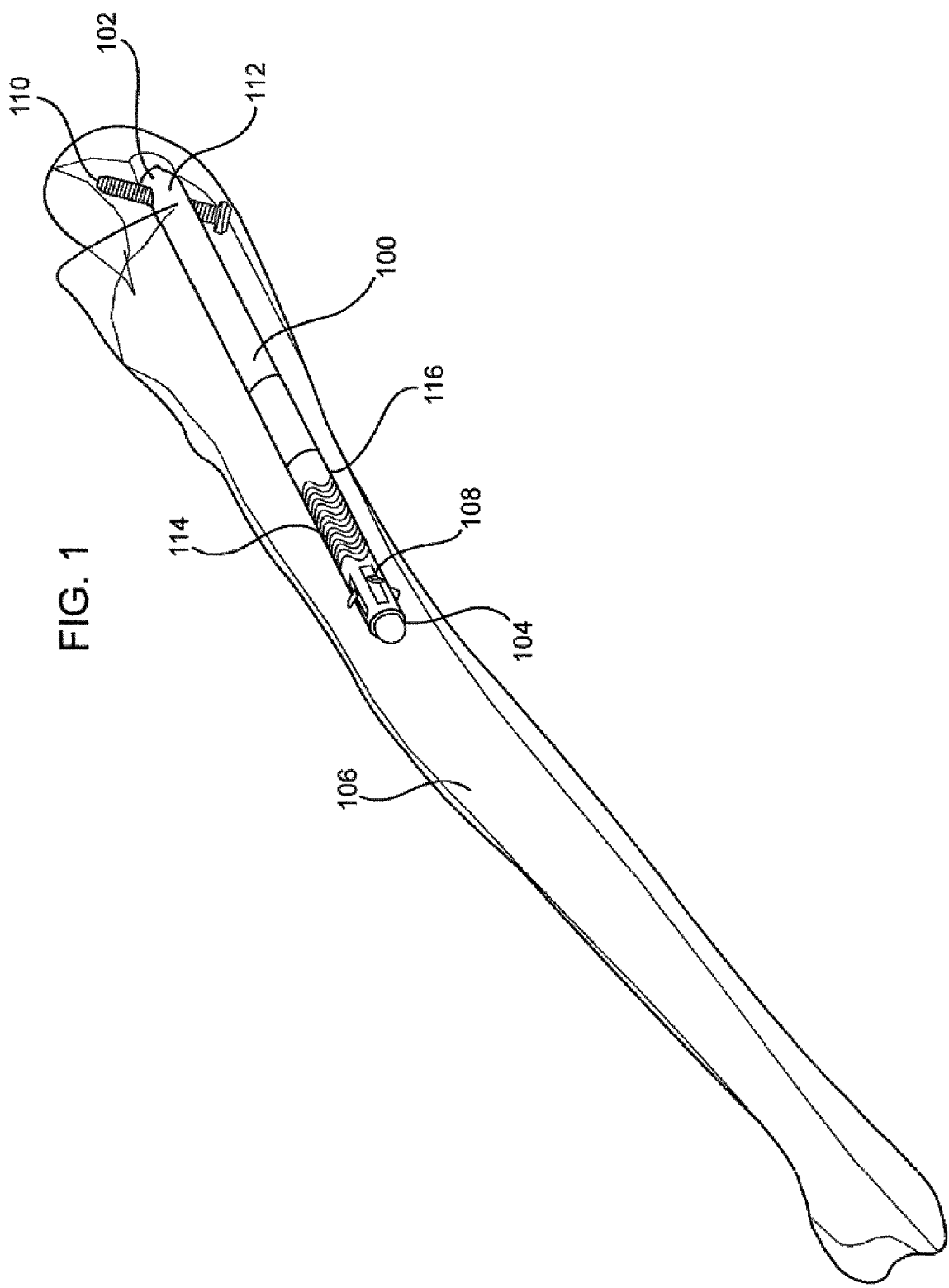
FIG. 1 is a perspective view of an embodiment of a bone fixation device implanted in a bone according to the invention.
Figure 2:
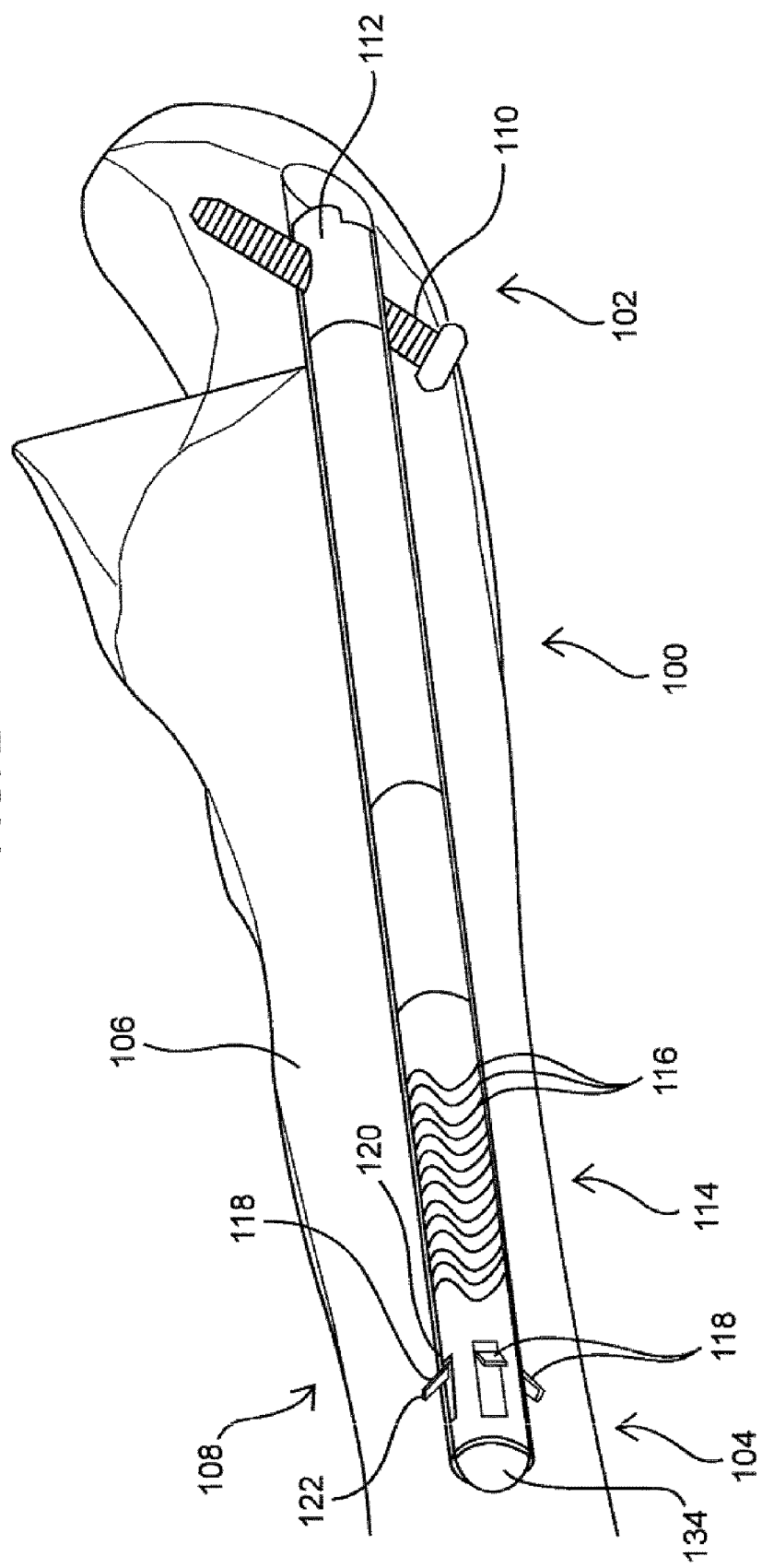
FIG. 2 is another perspective view of the implanted device of FIG. 1.

FIGS. 1 and 2 are perspective views of an embodiment of a bone fixation device 100 having a proximal end 102 (nearest the surgeon) and a distal end 104 (further from surgeon) and positioned within the bone space of a patient according to the invention. In this example, device 100 is shown implanted in the upper (or proximal) end of an ulna 106. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference.

When implanted within a patient, the device can be held in place with suitable fasteners such as wire, screws, nails, bolts, nuts and/or washers. The device 100 is used for fixation of fractures of the proximal or distal end of long bones such as intracapsular, intertrochanteric, intercervical, supracondular, or condular fractures of the femur; for fusion of a joint; or for surgical procedures that involve cutting a bone. The devices 100 may be implanted or attached through the skin so that a pulling force (traction may be applied to the skeletal system).

Figure 3:
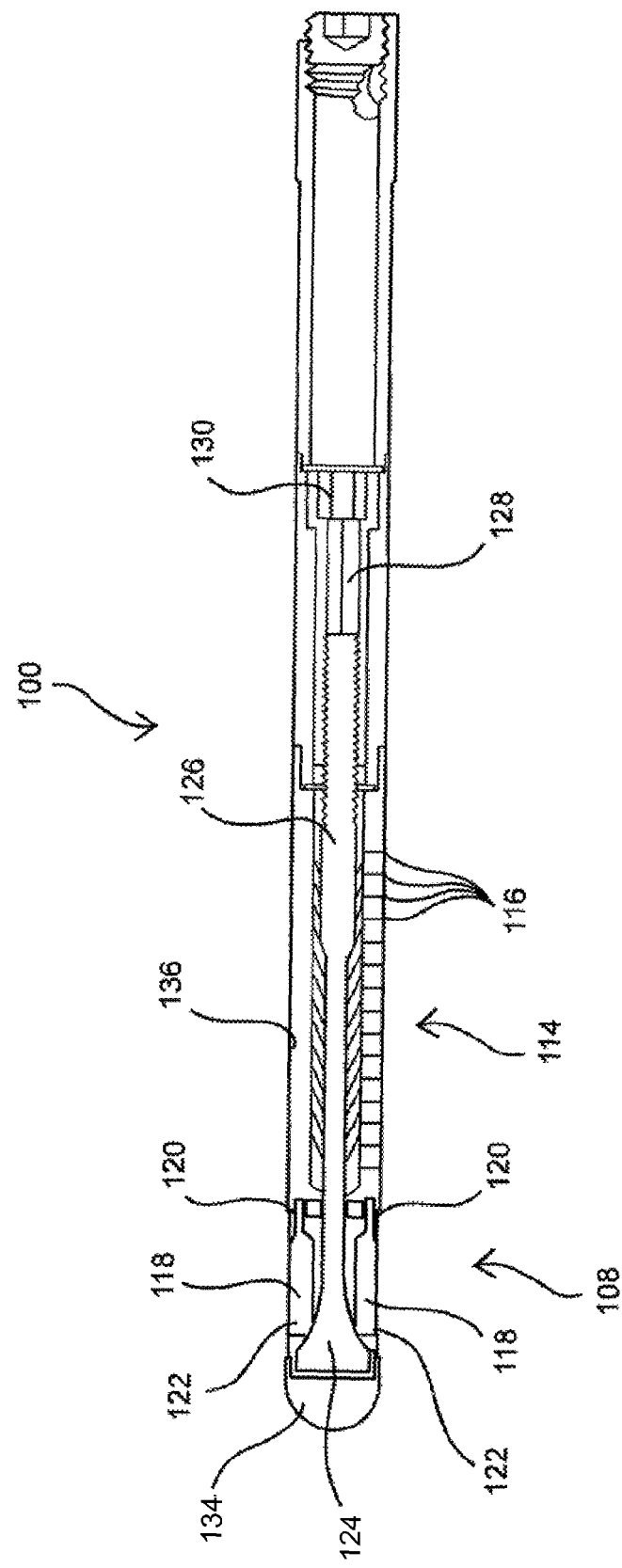
FIG. 3 is a longitudinal cross-section view of the bone fixation device of FIG. 1 in a non-deployed state.

In the embodiment shown in FIG. 1, the design of the metaphyseal fixation device 100 depicted is adapted to provide a bone engaging mechanism or gripper 108 adapted to engage target bone of a patient from the inside of the bone. As configured for this anatomical application, the device is designed to facilitate bone healing when placed in the intramedullary space within a post fractured bone. This device 100 has a gripper 108 positioned distally and shown deployed radially outward against the wall of the intramedullary cavity. On entry into the cavity, gripper 108 is flat and retracted (FIG. 3). Upon deployment, gripper 108 pivots radially outward and grips the diaphyseal bone from the inside of the bone. One or more screws 110 placed through apertures through the hub 112 lock the device 100 to the metaphyseal bone. Hence, the metaphysis and the diaphysis are joined. A flexible-to-rigid body portion 114 may also be provided, and in this embodiment is positioned between gripper 108 and hub 112. It may be provided with wavy spiral cuts 116, for example, for that purpose as will be described in more detail below.

FIG. 3 shows a longitudinal cross-section of device 100 in a non-deployed configuration. In this embodiment, gripper 108 includes two pairs of opposing bendable members 118. Two of the bendable members 118 are shown in FIG. 3, while the other two (not shown in FIG. 3) are located at the same axial location but offset by 90 degrees. Each bendable member 118 has a thinned portion 120 that permits bending as the opposite distal end 122 of member 118 is urged radially outward, such that member 118 pivots about thinned portion 120. When extended, distal ends 122 of bendable members 118 contact the inside of the bone to anchor the distal portion of device 100 to the bone. In alternative embodiments (not shown), the gripper may comprise 1, 2, 3, 4, 5, 6 or more bendable members similar to members 118 shown. Hence, the proximal end and or metaphysis and the distal end and or diaphysis are joined. The union between the proximal and distal ends may be achieved by the grippers, 108, alone or in concert with screws 110 placed through hub 112. Hub 112 may be either at the distal or proximal end of the bone, in this case the ulna. A hub 112 may be at both ends of the device, there by allowing screws to be placed in the distal and proximal ends. A flexible-to-rigid body portion 114 may also be provided, and in this embodiment is positioned between grippers 108 and 109. The flexible-to-rigid body portion may be placed proximal or distal to both sets of grippers, 108. In some embodiments, gripper 109 may be made of a nickel-titanium alloy.

During actuation, bendable members 118 of gripper 108 are urged radially outward by a ramped surface on actuator head 124. Actuator head 124 is formed on the distal end of actuator 126. The proximal end of actuator 126 is threaded to engage a threaded bore of drive member 128. The proximal end of drive member 128 is provided with a keyed socket 130 for receiving the tip of a rotary driver tool (not shown) through the proximal bore of device 100. As rotary driver tool turns drive member 128, actuator 126 is drawn in a proximal direction to outwardly actuate gripper members 118. In an alternative embodiment, actuator 126 may be made of a super elastic alloy that when released from its insertion state it returns to its unstressed state thereby driving grippers 108 and 109 outward, shortening the device thereby compressing 518 into a rigid state.

Gripper 108 and the actuator head 124 may be reversed in their geometrical layout of the device. The gripper 108 may be drawn by the actuator 126 over the actuator head 124, thereby deflecting the bendable members, 118, outward. Similarly, the bendable members, 118, may be made of a super elastic or elastic or spring alloy of metal whereby the bendable members are predisposed in their set state in the insertion configuration, that being their smallest diameter. When the actuator head, 124, engages the super elastic, elastic or spring alloy of steel bendable members 118, a continuous force is imparted upon actuator head 124 such that the bendable members 118 return to their insertion geometry after the actuator head 124 is removed. Typical super elastic, elastic, or spring alloys of metals include spring steels and NiTi or nitinol. Conversely, bendable members 118 may be made of super elastic, elastic, or spring alloys of metal and set in their maximum outside diameter, in their deployed state. Actuator 124 and the rectangular apertures in 518 would work cooperatively to expose the bendable members 118. Since the bendable members 118 would be set in their maximum outside dimension and constrained within 518, upon exposure of 118 to the rectangular apertures, the bendable members would be driven by the material properties into the bone.

A hemispherical tip cover 134 may be provided at the distal end of the device as shown to act as a blunt obturator. This arrangement facilitates penetration of bone by device 100 while keeping the tip of device 100 from digging into bone during insertion. The tip may have various geometrical configurations that adapt to enabling tools such as guide wires and guide tubes. The tip may be actively coupled to an electrical or mechanical source that removes or ablates bone to facilitate insertion.

As previously mentioned, device 100 may include one or more flexible-to-rigid body portions 114. This feature is flexible upon entry into bone and rigid upon application of compressive axial force provided by tensioning actuator 126. Various embodiments may be used, including dual helical springs whose inner and outer tubular components coil in opposite directions, a chain of ball bearings with flats or roughened surfaces, a chain of cylinders with flats, features, cones, spherical or pointed interdigitating surfaces, wavy-helical cut tubes, two helical cut tubes in opposite directions, linear wires with interdigitating coils, and bellows-like structures.

The design of the flexible-to-rigid tubular body portion 114 allows a single-piece design to maximize the transformation of the same body from a very flexible member that minimizes strength in bending to a rigid body that maximizes strength in bending and torque. The flexible member transforms to a rigid member when compressive forces are applied in the axial direction at each end, such as by an actuator. The body portion 114 is made, for example, by a near-helical cut 116 on a tubular member at an angle of incidence to the axis somewhere between 0 and 180 degrees from the longitudinal axis of the tubular body portion 114. The near-helical cut or wavy-helical cut may be formed by the superposition of a helical curve added to a cyclic curve that produces waves of frequencies equal or greater than zero per turn around the circumference and with cyclic amplitude greater than zero. The waves of one segment nest with those on either side of it, thus increasing the torque, bending strength and stiffness of the tubular body when subjective to compressive forces. The tapered surfaces formed by the incident angle allow each turn to overlap with the segment on either side of it, thus increasing the bending strength when the body is in compression. Additionally, the cuts can be altered in depth and distance between the cuts on the longitudinal axis along the length of body portion 114 to variably alter the flexible-to-rigid characteristics of the tubular body along its length.

The cuts 116 in body portion 114 allow an otherwise rigid member to increase its flexibility to a large degree during deployment. The tubular member can have constant or varying internal and external diameters. This design reduces the number of parts of the flexible-to-rigid body portion of the device and allows insertion and extraction of the device through a curved entry port in the bone while maximizing its rigidity once inserted. Application and removal of compressive forces provided by a parallel member such as wire(s), tension ribbons, a sheath, or actuator 126 as shown will transform the body from flexible to rigid and vice versa.

In operation, as actuator 126 is tightened, gripper members 118 are extended radially outwardly. Once the distal ends of gripper members 118 contact bone and stop moving outward, continued rotation of actuator 126 draws the proximal end 102 and the distal end 104 of device 100 closer together until cuts 116 are substantially closed. As this happens, body portion 114 changes from being flexible to rigid to better secure the bone fracture(s), as will be further described below. Rotating actuator 126 in the opposite direction causes body portion 114 to change from a rigid to a flexible state, such as for removing device 100 if needed in the initial procedure or during a subsequent procedure after the bone fracture(s) have partially or completely healed. Body portion 114 may be provided with a solid longitudinal portion 136 (shown in FIG. 3) such that cuts 116 are a series of individual cuts each traversing less than 360 degrees in circumference, rather than a single, continuous helical cut. This solid portion 136 can aid in removal of device 100 by keeping body portion 114 from undesirably extending like a spring. One or more internal tension members (not shown) may also be used to limit the extension of body portion 114 when it is in tension. In an alternative embodiment, actuator 126 may be made of a super elastic alloy that when released from its insertion state it returns to its unstressed state thereby driving grippers 108 and 109 outward, shortening the device thereby compressing 518 into a rigid state. To some one skilled in the art, the gripper 108 and the actuator head 124 can be reversed in their geometrical layout of the device. The gripper 108 could be drawn by the actuator 126 over the actuator head 124, thereby deflecting the bendable members, 118, outward. Similarly, the bendable members, 118, may be made of a super elastic or elastic or spring alloy of metal where by the bendable members are predisposed in their set state in the insertion configuration, that being their smallest diameter. When the actuator head, 124, engages the super elastic, elastic or spring alloy of steel bendable members, 118, a continuous force is imparted upon actuator head 124 such that the bendable members 118, return to their insertion geometry after the actuator head 124 is removed. Typical super elastic, elastic, or spring alloys of metals include spring steels and NiTi or nitinol. Conversely, bendable members 118 may be made of super elastic, elastic, or spring alloys of metal and set in their maximum outside diameter, in their deployed state. Actuator 124 and the rectangular apertures in 518 would work cooperatively to expose the bendable members 118. Since the bendable members 118 would be set in their maximum outside dimension and constrained within 518, upon exposure of 118 to the rectangular apertures, the bendable members would be driven by the material properties into the bone.

FIGS. 4, 5A and 5B show various exemplary embodiments of anatomy or shape conforming body portions constructed according to aspects of the present invention. These and other body portions may be used in bone fixation devices similar to those described above. These body portions may be used in place of body portion 114 previously described to allow the device to take on a shape that conforms to a particular anatomy when the body of the device is axially compressed when making the device substantially rigid.

Referring first to FIG. 4, flexible-to-rigid tubular body portion 114' includes a first side 410 which forms a solid spine and a second side 412 which has a series of straight, V-shaped cuts 414 in it. In this embodiment, the V-shaped cuts 414 extend a substantial portion of the way across the diameter of tubular body portion 114'. As body portion 114' is axially compressed in manner similar to body portion 114 previously described, the first side 410 retains its original length because it is solid. The second side 412, however, is foreshortened as V-shaped cuts 414 begin to close. With this difference in lengths between sides 410 and 412, body portion 114' takes on a curved shape, with first side 410 becoming convex and second side 412 becoming concave. The curved configuration of body portion 114' can be designed to match the curve of an intramedullary bone cavity where the body portion 114' is being implanted.

FIG. 5A shows another embodiment of a flexible-to-rigid tubular body portion 114". Body portion 114" has a first side 510, a second side 512, and a series of wavy slits 514. Slits 514 may be individual slits extending partially around the circumference of body portion 114", leaving a solid spine near first side 510, similar to first side 410 shown in FIG. 4. Alternatively, slits 514 may extend completely around the circumference of body portion 114', creating a series of solid wavy rings therebetween. In yet another alternative, slits 514 may extend completely around the circumference of body portion 114" in spiral fashion to create one continuous helical slit.

As can be seen in FIG. 5A, slits 514 have a varying width that increases as they extend from first side 510 to second side 512. With this configuration, second side 512 will foreshorten more than first side 510 as slits 514 close during axial compression. This results in body portion 114" taking on a curved shape, with first side 510 becoming convex and second side 512 becoming concave. The alternating curves of slits 514 provide increased torsional rigidity, particularly when body portion 114" is axially compressed.

FIG. 5B shows yet another embodiment of a flexible-to-rigid tubular body portion 114'''. Body portion 114''' has a first side 610, a second side 612, and a series of wavy slits 614. First side 610 forms a solid spine that does not axially compress. In this embodiment, slits 614 have a generally uniform width. During axial compression, body portion 114''' takes on a curved shape, with first side 610 becoming convex and second side 612 becoming concave.

Alternative designs (not shown), such as wave patterns of an interdigitating saw tooth or square wave, and the like, are also contemplated for increased torsional rigidity. As described above, these patterns may form discrete rings around body portion 114, or these patterns may be superimposed on a helical curve to form a continuous spiral pattern.

FIGS. 6A-6J show further exemplary embodiments of anatomy or shape conforming body portions constructed according to aspects of the present invention. Similar to the body portions described above, the body portions shown in FIGS. 6A-6J may be used in place of body portion 114 previously described to allow an implantable bone fixation device to take on a shape that conforms to a particular anatomy when the body of the device is axially compressed when making the device substantially rigid. The body portions shown in FIGS. 6A-6J have interlocking appendages or features that allow each body portion to transform from a generally flexible state to a generally rigid state when axial compression is applied. Like some of the body portions described above, these interlocking features also permit the transmission of torsional forces in both the flexible and rigid states of the device. Being able to transmit torsional forces without excessive rotational displacement from one end of the implantable device to the other can be advantageous in various situations, such as during insertion or removal of the device, or when a surgeon desires to rotate the device to properly align it during installation in a bone. Additionally, the interlocking features of the exemplary embodiments shown are designed to resist tensile forces. This allows the surgeon to pull on the proximal end of the device without the device uncoiling or extending excessively in length.

Figure 6A:
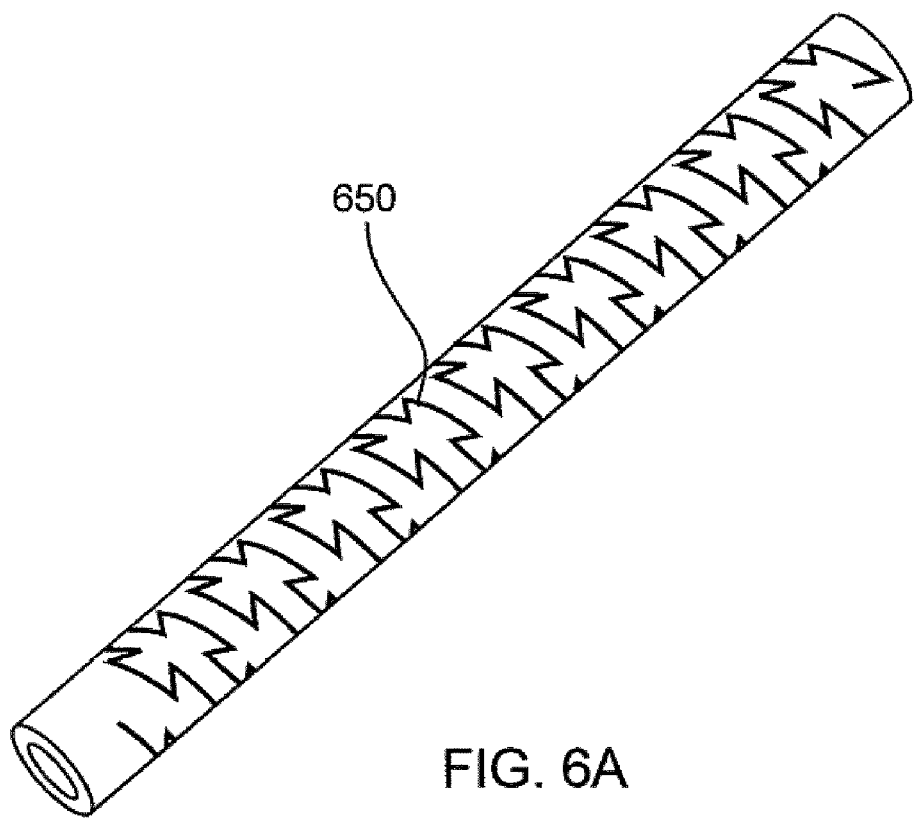
FIG. 6A is a perspective view showing another body portion embodiment having interlocking features.
Figure 6B:
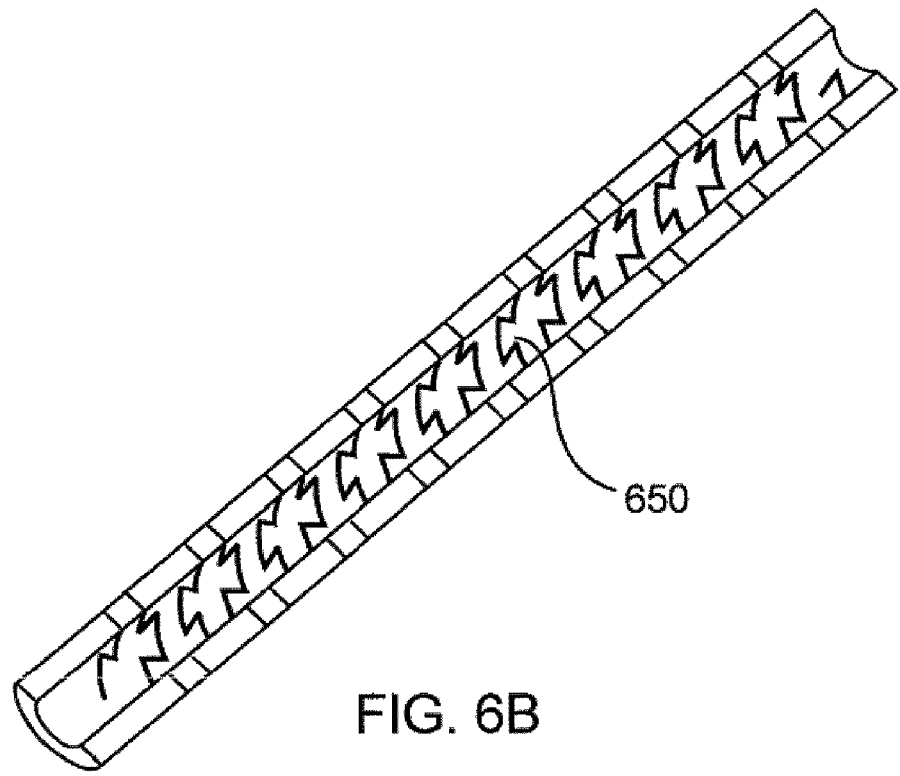
FIG. 6B is a longitudinal cross-sectional view of the body portion shown in FIG. 6A.
Figure 6C:
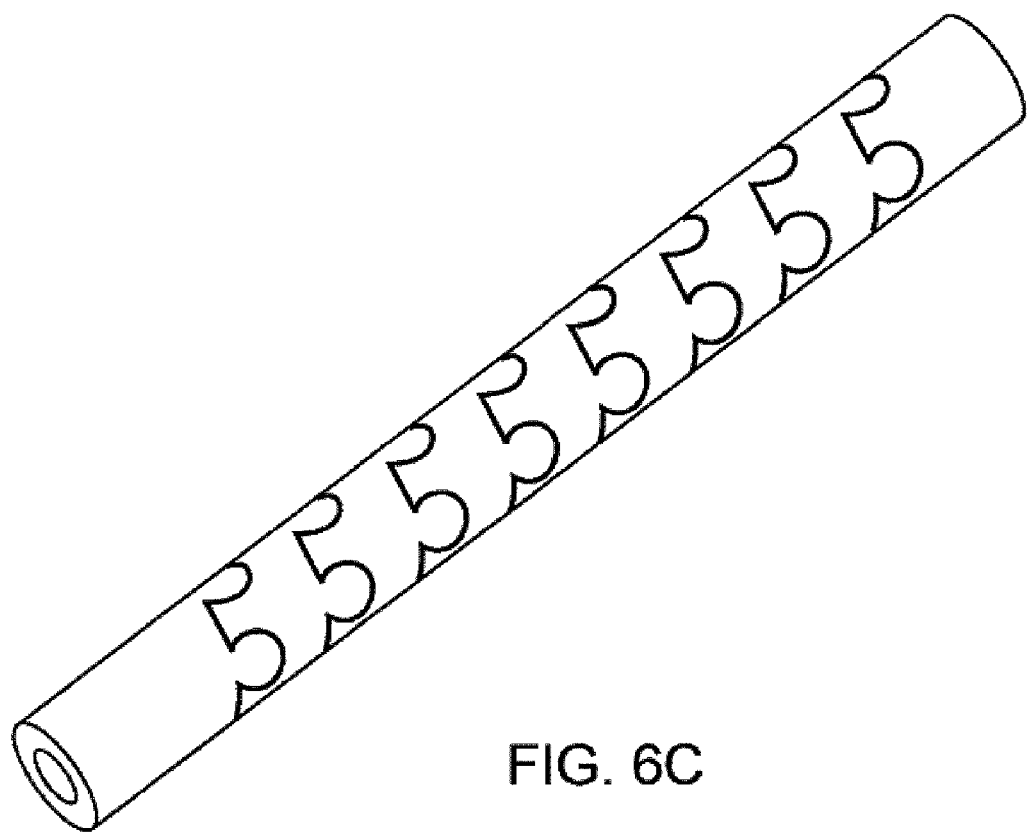
FIG. 6C is a perspective view showing another body portion embodiment having interlocking features.
Figure 6D:
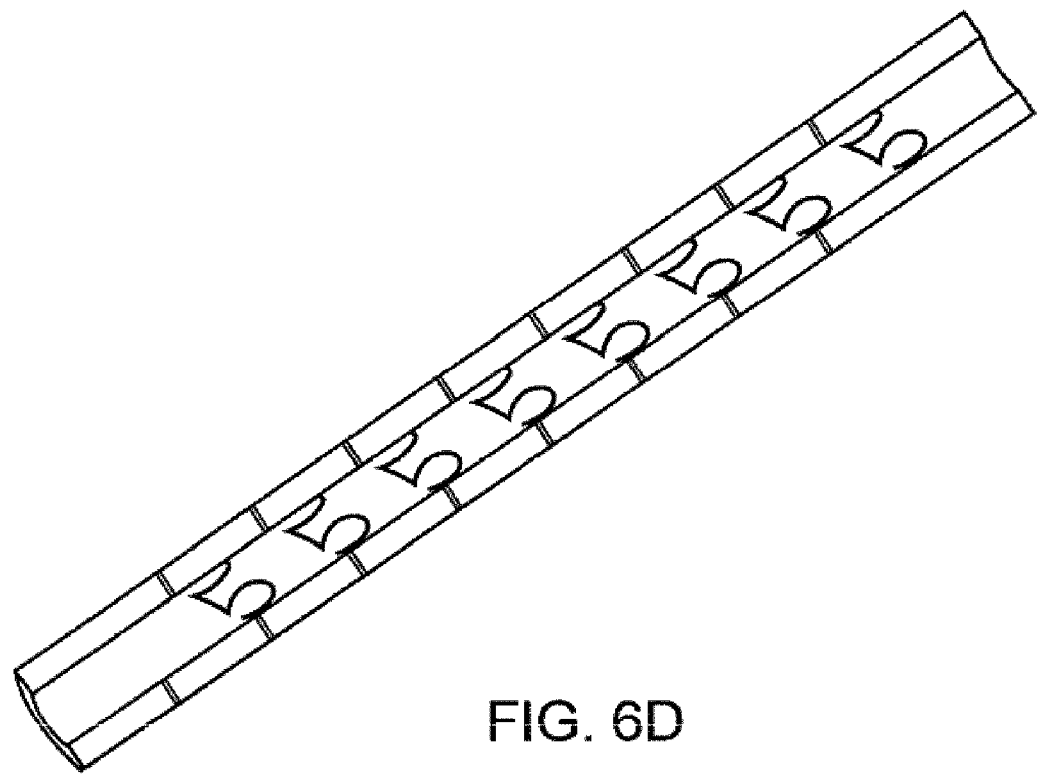
FIG. 6D is a longitudinal cross-sectional view of the body portion shown in FIG. 6C.
Figure 6E:
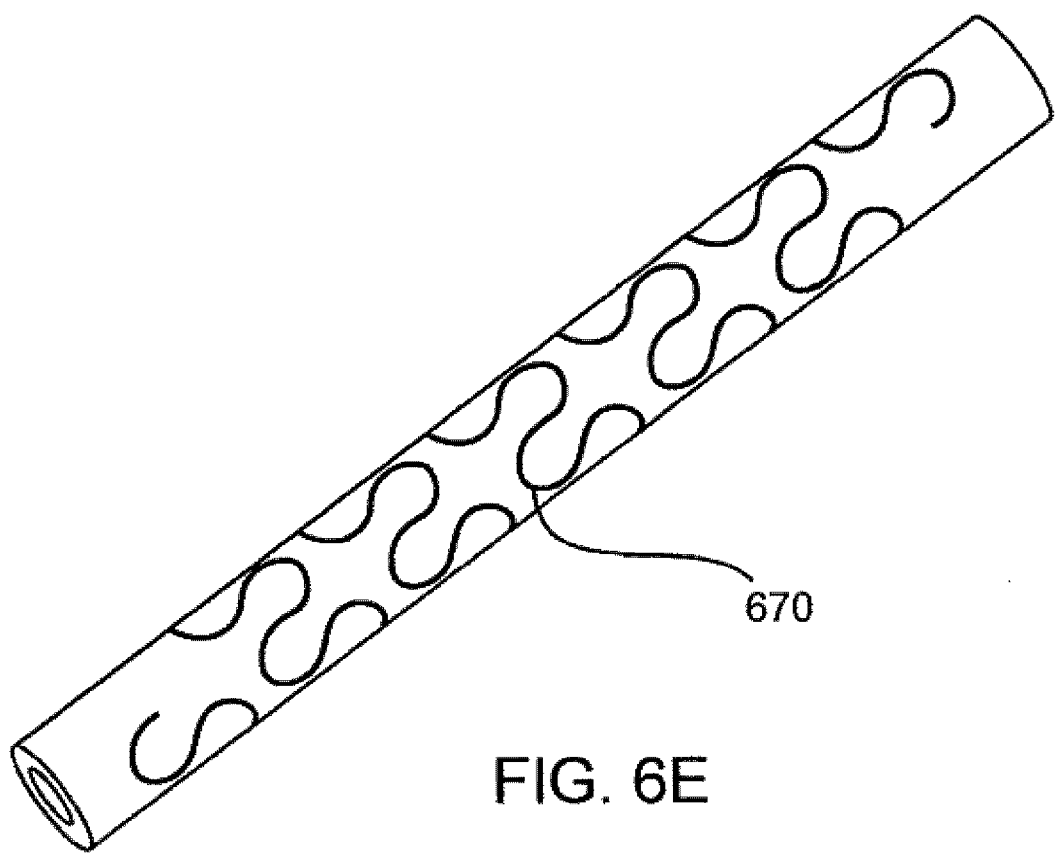
FIG. 6E is a perspective view showing another body portion embodiment having interlocking features.
Figure 6F:
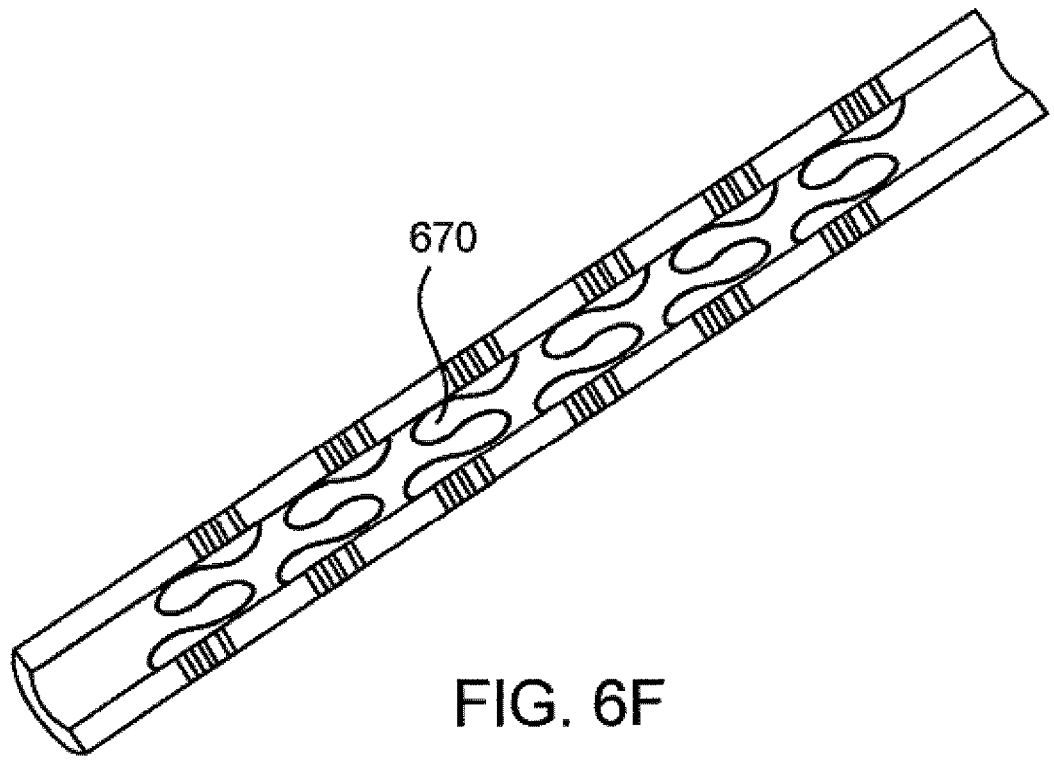
FIG. 6F is a longitudinal cross-sectional view of the body portion shown in FIG. 6E.
Figure 6G:
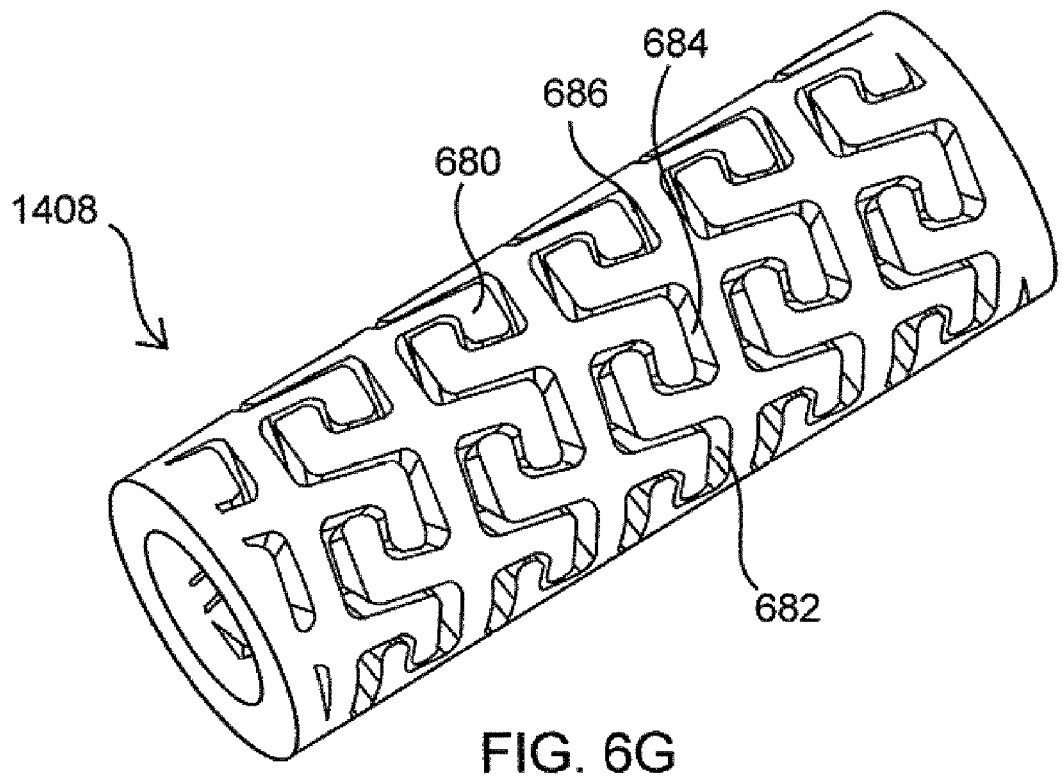
FIG. 6G is a perspective view showing another body portion embodiment having interlocking features.
Figure 6H:
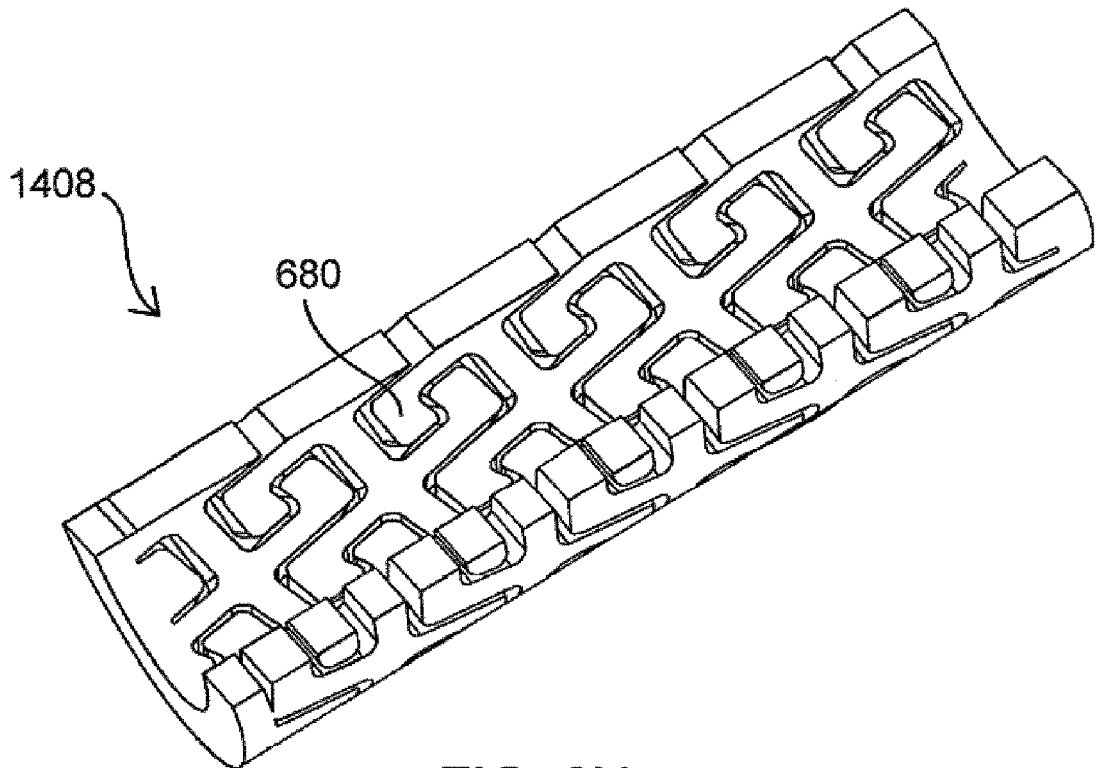
FIG. 6H is a longitudinal cross-sectional view of the body portion shown in FIG. 6G.
Figure 6I:
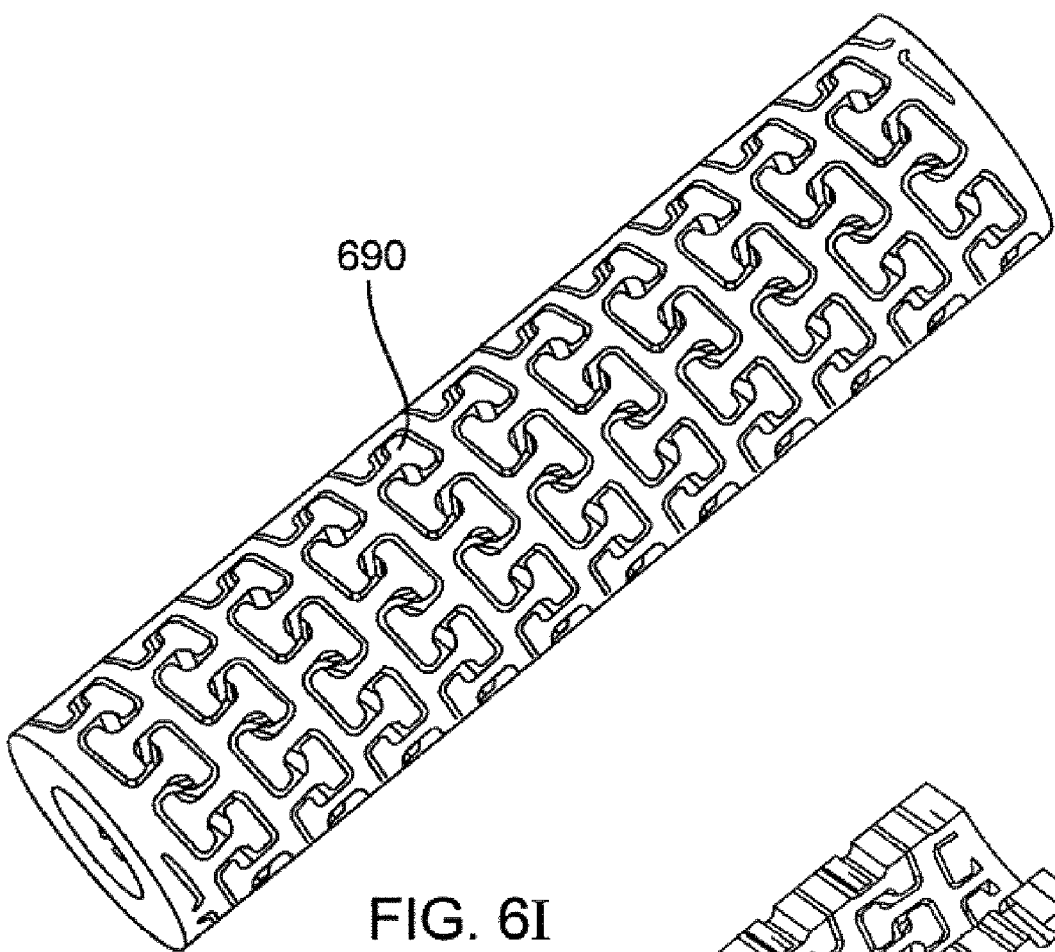
FIG. 6I is a perspective view showing another body portion embodiment having interlocking features.
Figure 6J:
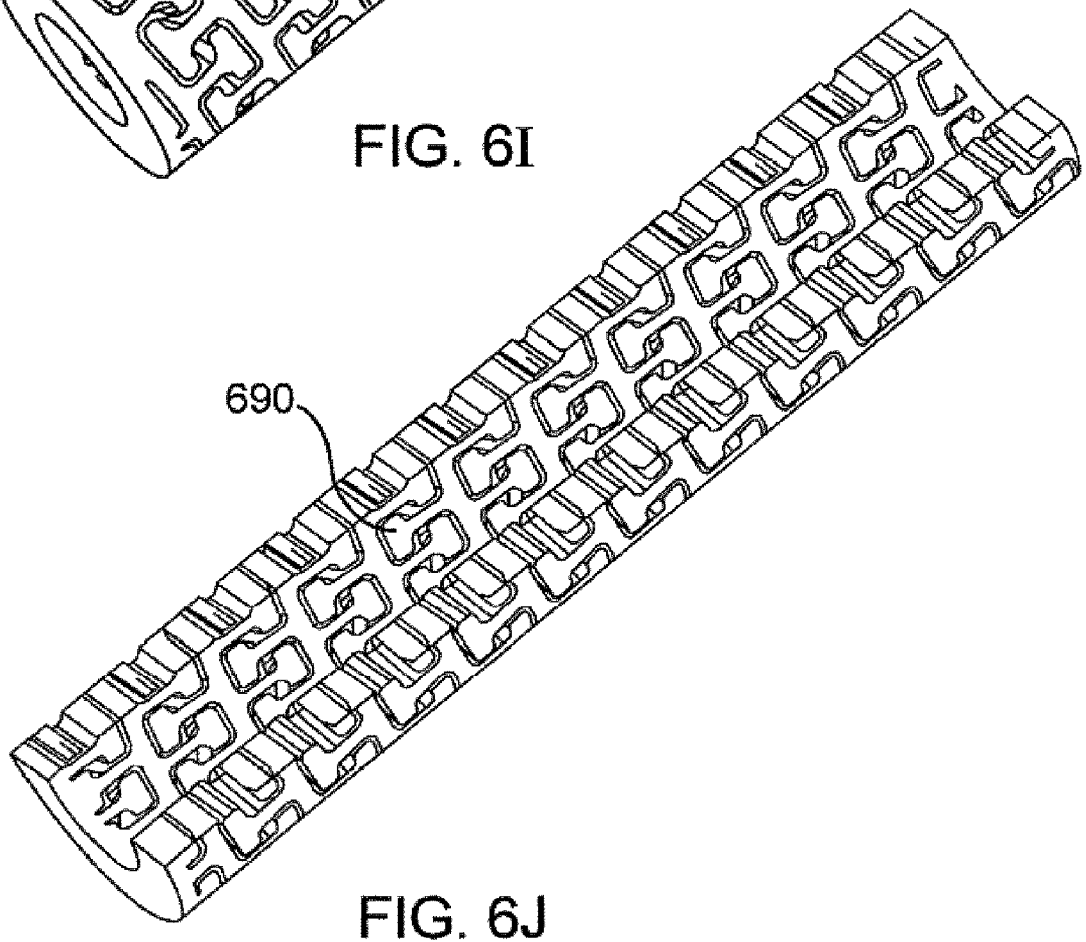
FIG. 6J is a longitudinal cross-sectional view of the body portion shown in FIG. 6I.

As seen in the flexible-to-rigid body portion shown in FIGS. 6A and 6B, the interlocking features can comprise an alternating trapezoid or dovetail pattern 650 superimposed on a helical curve. As shown in FIGS. 6C and 6D, the interlocking features can comprise an omega shape 660. FIGS. 6E and 6F show that the interlocking features can comprise bulbous pendicles 670. FIGS. 6G and 6H show that the interlocking features can comprise an L-shape 680. Note that the gap 682 between features in one column is wider than gap 684 in the adjacent column, which in turn is wider than gap 686 in the next column. This progressive widening of gaps from one side of the flexible to rigid body portion to the other causes the body portion to curve when compressed, as will be further described below. FIGS. 6I and 6J show an example of T-shaped interlocking features 690. In other embodiments, a pattern of interlocking features can be continuous or intermittent. The interlocking features may also vary in a radial direction across the tube wall, and/or in an axial direction rather than, or in addition to, varying across the circumference of the tube as shown in FIGS. 6A-6J.

The body portions shown in FIGS. 6A-6J need not be curved when axially compressed as described above. Rather, they may be designed so that they compress equally on all sides of the center axis such that they form a straight segment when either flexible or rigid. Alternatively, the body portions may be designed to be curved when flexible, and compress in a uniform fashion such that they maintain their curved shape when transformed to a generally rigid state.

FIGS. 6A-6J provide exemplary geometries for a variety of cut patterns. The cross sectional geometry is shown as tubular. As discussed in more detail below, the cross sectional area can be of any shape tubular geometry or solid geometry. The specific cut pattern and cross sectional shape are selected and designed to match the anatomical shape of the bone or to provide specific fixation or reconstructive surfaces particularly suited to remediate the problem with the bone. Different cross sectional geometries are needed for the flat bones found in the face and skull, the ribs, the tibial plateau, the metacarpals, the metatarsals, and the scaphoid bone of the hand. The cut pattern can be "programmed" to reconstruct the bone into its anatomical configuration or into a modified configuration based upon the desired result of the remediation therapy. For instance, a reconstructive procedure may be prescribed to remediate a malunion of a bone. In this example the device, rather than collapsing upon activation lengthens and becomes rigid.

Although shown in the various embodiments of the figures is a device with grippers, it is also envisioned that the flexible-to-rigid member would collapse or extend such that axially successive geometries would be upset and driven radially outward. In its flexible state the cut patterns would freely bend relative to each other. Upon activation to the rigid state, for example, a crest of a wave pattern would be urged outward, thereby increasing the effective diameter of the device. The crest of the wave could be forced into the intramedullary bone and create a fixation moiety. One could envision a long tube where the crests of the wave patterns would be drive outward there by creating a high surface area of gripping power over the entire length of the device. Other pattern besides wave patterns could be made to do this.

Figure 7A:
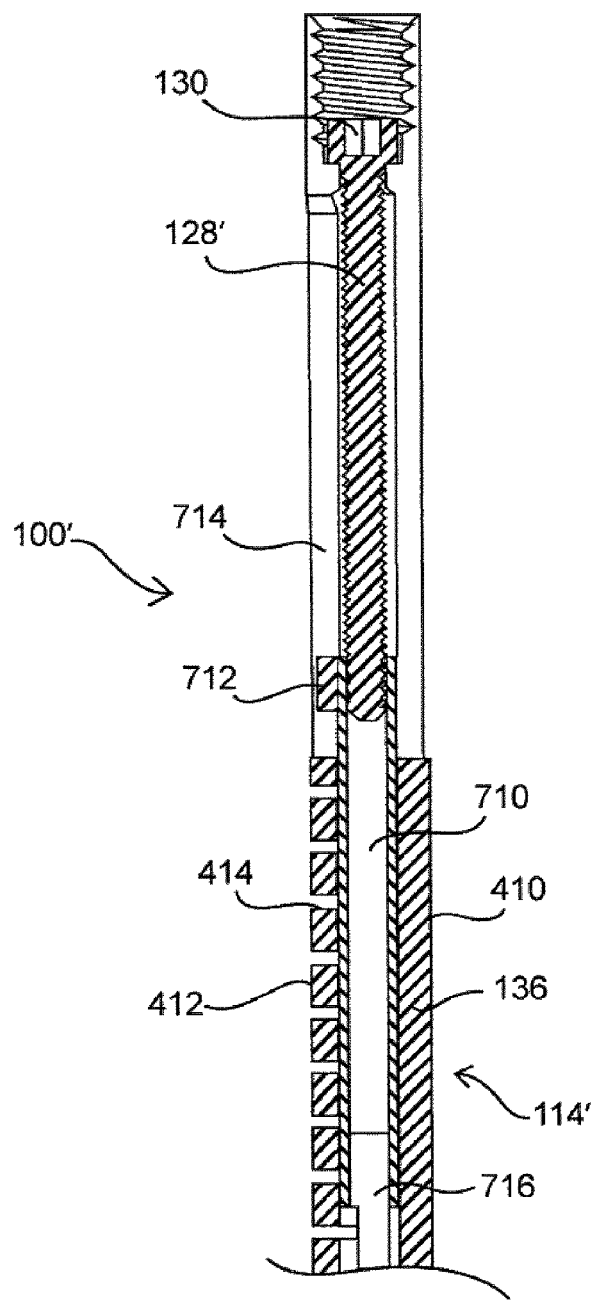
FIG. 7A is a cross-sectional view showing the proximal end of a device employing the body portion of FIG. 4, the device being shown in a flexible state.
Figure 7B:
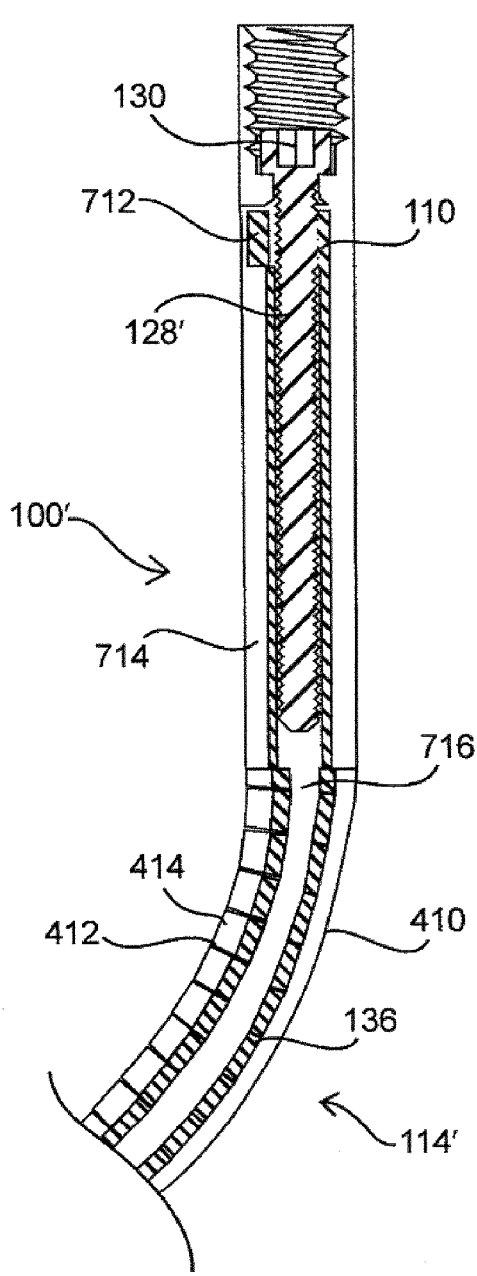
FIG. 7B is a cross-sectional view showing the proximal end of a device employing the body portion of FIG. 4, the device being shown in a shape-conforming state.

FIGS. 7A and 7B depict the proximal end of a device 100' which is similar to device 100 previously described but incorporating the flexible-to-rigid tubular body portion 114' of FIG. 4. FIG. 7A shows device 100' in a flexible, undeployed state, and FIG. 7B shows device 100' in a generally rigid, curved state. To change between states after device 100' is inserted in the intramedullary cavity of a bone, the tip of a rotary driver tool (not shown) is inserted in keyed socket 130 of drive member 128' and rotated. Drive member 128' is threadably engaged with shuttle 710. Shuttle 710 may be constructed in a flexible manner such that body portion 114' remains flexible when in the undeployed state of FIG. 7A. Shuttle 710 may include a tab 712 at its proximal end that travels in slot 714 in the tube wall to prevent shuttle 710 from rotating (as best seen in FIG. 8D). As drive member 128' is rotated by the driver tool, shuttle 710 is drawn towards the proximal end of device 100', as shown in FIG. 7A. The proximal end of a tension wire 716 in turn is rigidly attached to shuttle 710. The distal end of tension wire 716 (not shown) may be coupled to a distal gripper as previously described, or attached to the distal end of device 100'. When tension wire 716 is drawn proximally by shuttle 710, V-shaped gaps 414 on the second side 412 of body portion 114' are closed, causing body portion 114' to assume a curved shape as shown in FIG. 7B.

Figures 8A, 8B, 8C:
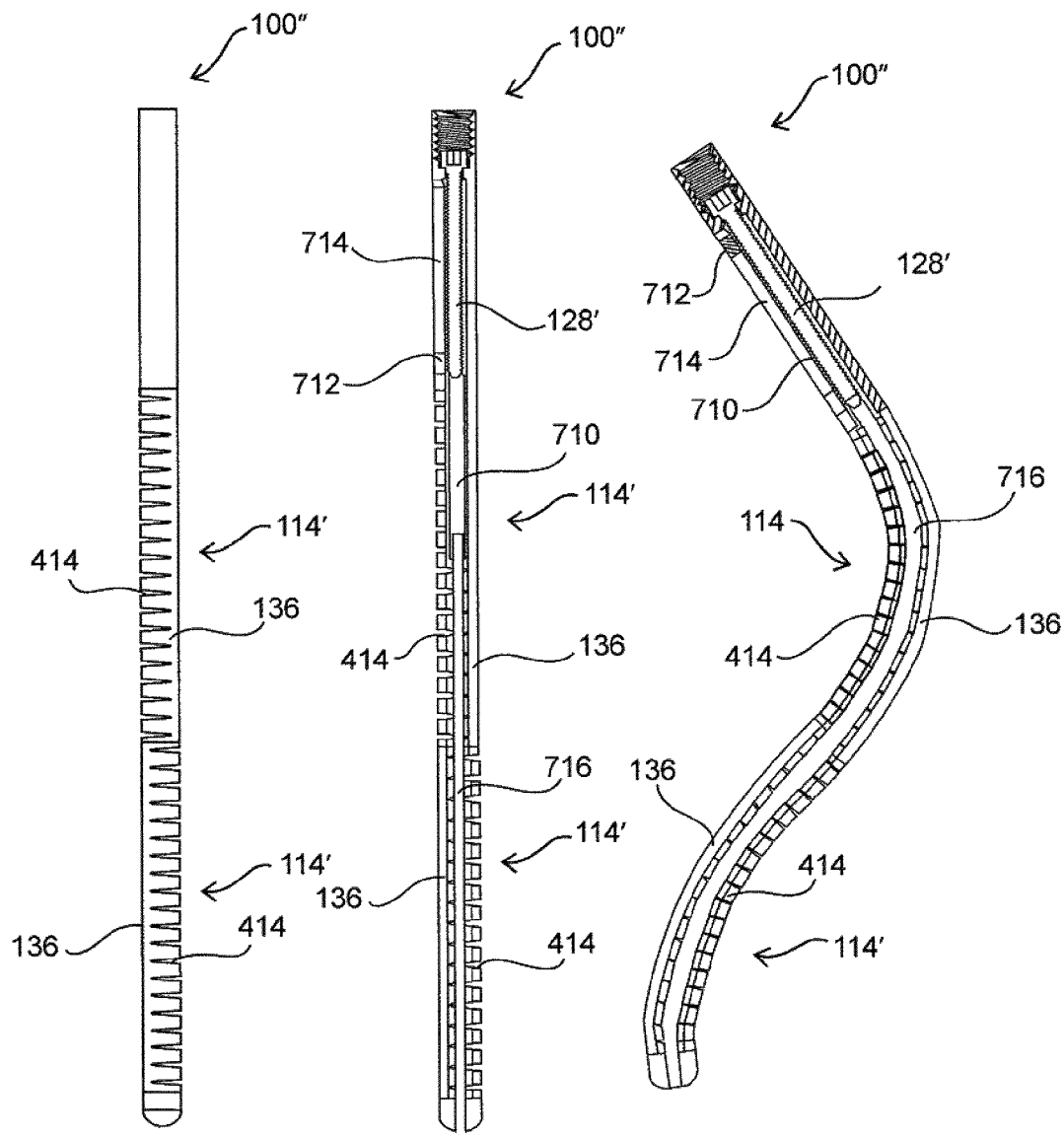
FIG. 8A is a side view showing a device employing two body portions of FIG. 4, the device being shown in a flexible state.
FIG. 8B is a cross-sectional view showing a device employing two body portions of FIG. 4, the device being shown in a flexible state.
FIG. 8C is a cross-sectional view showing a device employing two body portions of FIG. 4, the device being shown in a shape-conforming state.
Figure 8D:
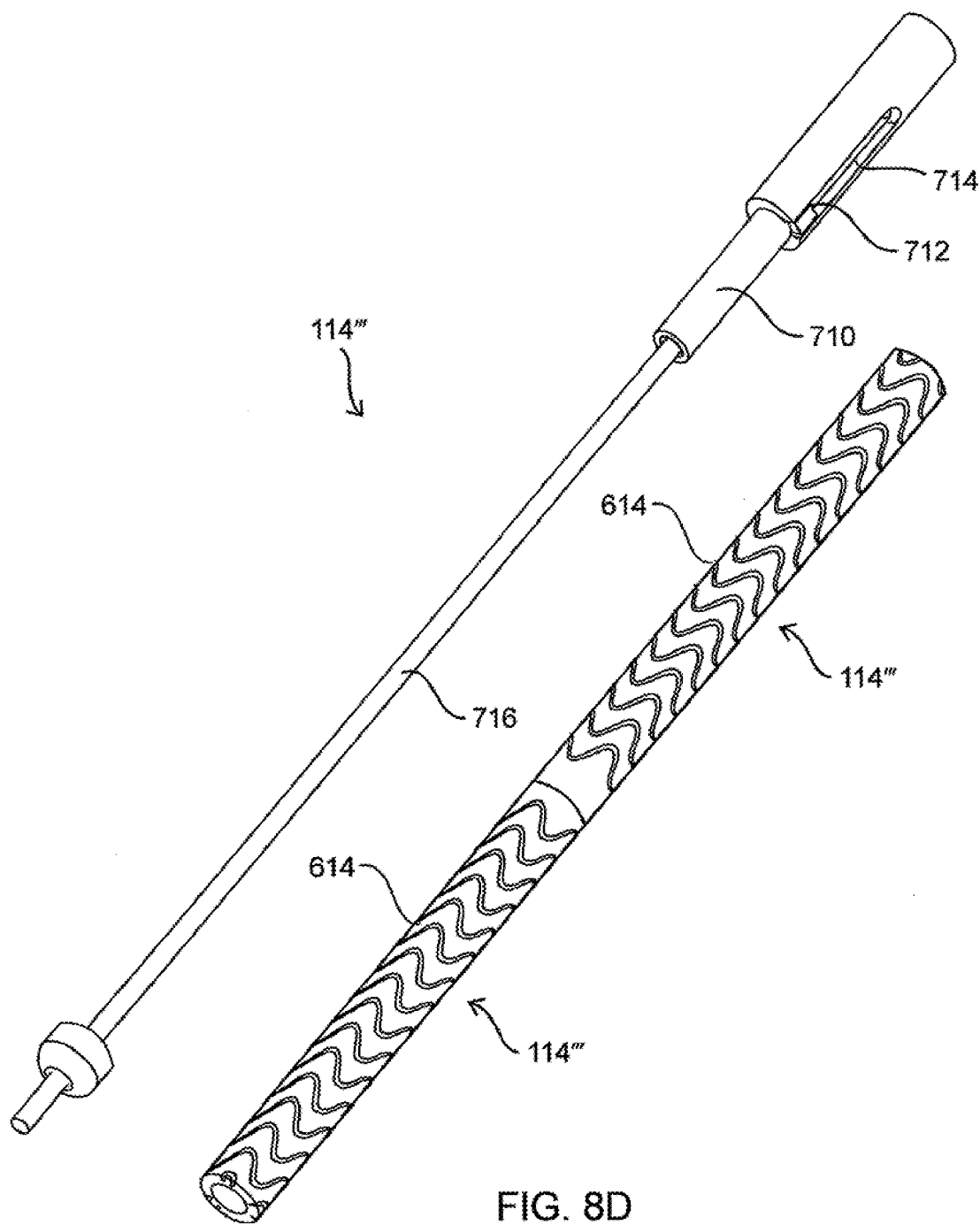
FIG. 8D is a partially exploded perspective view showing a device employing two body portions of FIG. 5B, the device being shown in a flexible state.

FIGS. 8A-8C show an alternative embodiment device 100" in various states. FIG. 8A shows device 100" in a non-tensioned state, FIG. 8B shows a cross-section of device 100" in the non-tensioned state, and FIG. 8C shows a cross-section of device 100" in a tensioned state.

Device 100" includes two flexible-to-rigid tubular body portions 114', 114' oriented in opposite directions. With this configuration, when shuttle 710 and tension wire 716 are drawn proximally by rotating drive member 128, device 100" assumes an S-shape, as shown in FIG. 8C. Thus, device 100" may be used to repair S-shaped bones such as the clavicle. In a similar manner, the axial width, axial pitch and/or radial orientation of V-shaped cuts 414 can be varied to produce compound, varying curves in three dimensions to match any desired anatomy. For obtaining smaller radii of curvature, V-shaped cuts 414 that are more blunt may be used. The flexible to rigid body portions need not be of identical cross section. For example a round tubular section could be paired with a hexagonal tubular section. This would allow one section to rotate freely within the space it is located where the hexagonal structure would provide a form of resistance or registration.

Figure 8E:
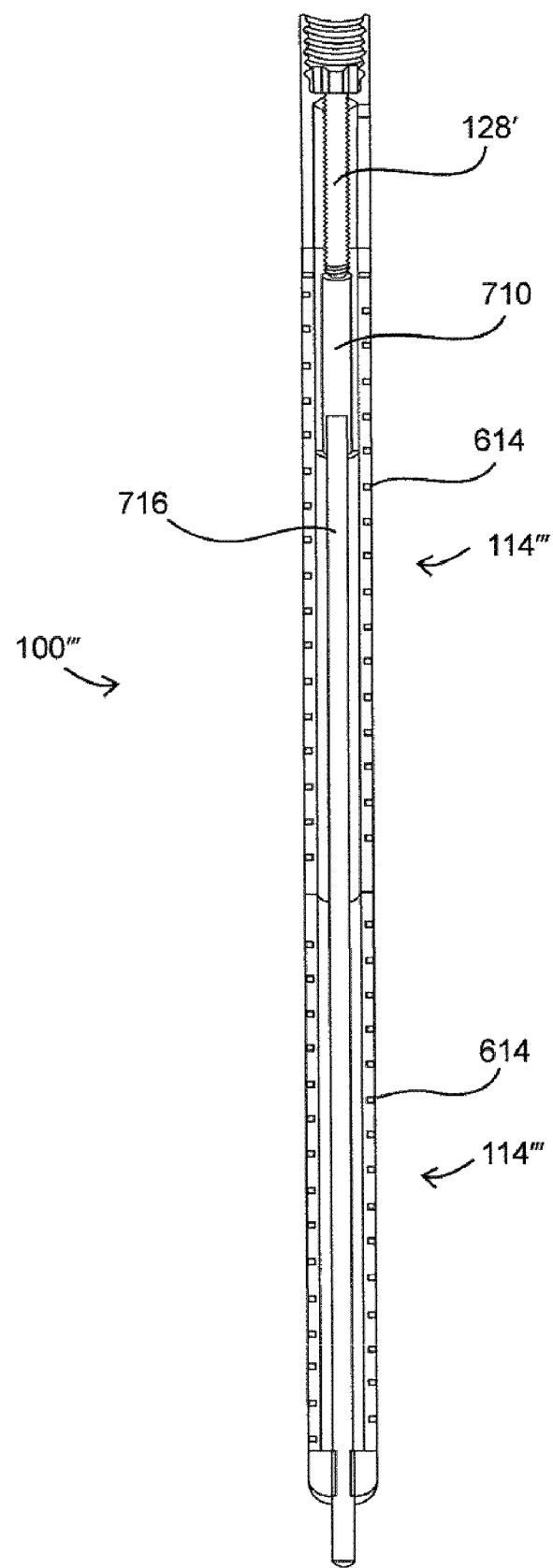
FIG. 8E is a cross-sectional view showing a device employing two body portions of FIG. 5B, the device being shown in a flexible state.

FIGS. 8D and 8E show an S-forming device 100'''similar to device 100" shown in FIGS. 8A-8C, but having wavy slits 614 instead of straight V-shaped cuts 414.

Figure 9:
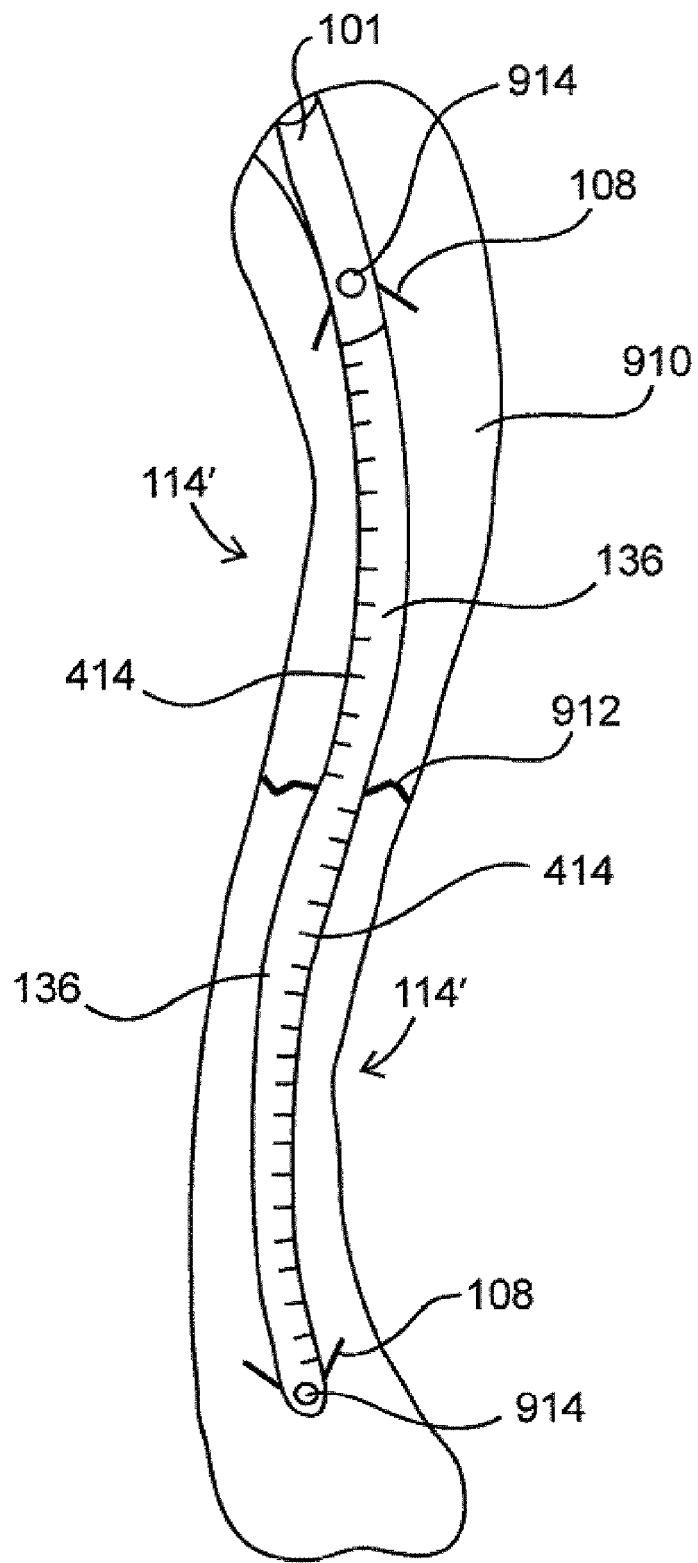
FIG. 9 is plan view depicting a device similar to that of FIGS. 8A-8C, the device being shown deployed in a clavicle.

FIG. 9 depicts an S-shaped device similar to device 100''' deployed in a clavicle bone 910 across a mid-shaft fracture 912. Device 101 may be configured with a gripper 108 and/or one or more screw holes 914 at its proximal end to secure device 101 to one half of clavicle 910. Similarly, device 101 may be configured with a gripper 108 and/or one or more screw holes 914 at its distal end to secure device 101 to the other half of clavicle 910. Body portions 114', 114' are configured such that they are flexible when being introduced into clavicle 910. When grippers 108, 108 are deployed and body portions 114', 114' become rigid as described above, device 101 assumes an S-shape that closely matches the contour of the intramedullary cavity within clavicle 910. Such a configuration allows device 101 to more rigidly support clavicle 910 for healing of fracture 912 while avoiding undue forces on clavicle 910.

Figure 10:
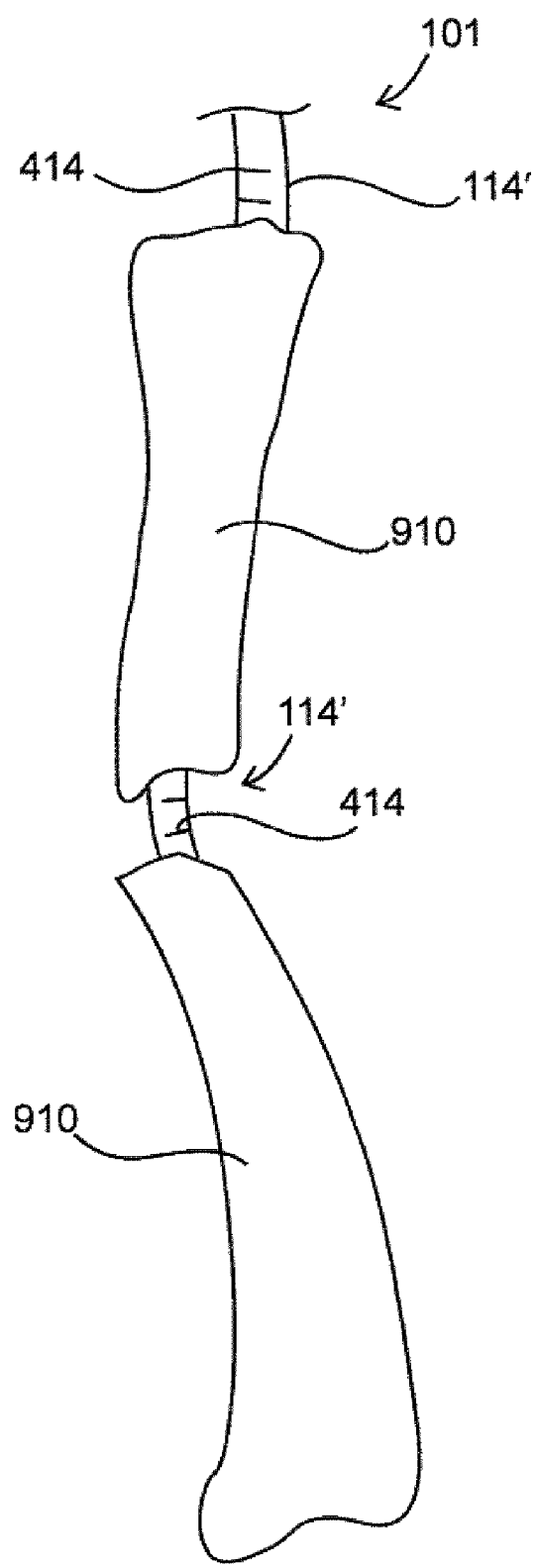
FIG. 10 is a perspective view showing a device similar to that of FIGS. 8A-8C, the device being introduced into the intramedullary space of a clavicle.

FIG. 10 shows device 101 described above and depicted in FIG. 9 as it is being introduced into a fractured clavicle 910.

FIG. 11 shows an alternative shape conforming device 103. Device 103 forms a simple curve when flexible-to-rigid body portion 114" (also shown in FIG. 5A) is in a rigid state. Device 103 includes a gripper 108' at its distal end, having opposing tube segments 1110, 1110 that rotate to engage the bone when gripper 108' is deployed. Device 103 also has a tripod gripper 108" at its proximal end, having three pairs of scissor arms 1112, 1112, 1112 for engaging the bone when actuated. Further details of grippers 108' and 108" are provided in copending application Ser. No. 11/944,366 referenced above.

FIG. 12 shows an alternative shape conforming device 105. As shown, device 105 forms an S-shape when flexible-to-rigid body portions 114" are in a rigid state. The distal end of device 105 may be secured to the bone by gripper 108, and the proximal end may be secured with bone screws through the device, as shown in FIGS. 1 and 2.

In alternative embodiments (one of which will be described below), grippers 108 and screw 110 attachment provisions may be omitted from one or both ends of the device. In these embodiments, the curved nature of body portion(s) 114' is enough to secure the device end(s) within the bone and hold the fracture(s) in place. In embodiments with and without grippers 108 and screws 110, the anatomy-conforming curve may serve to grip the bone and approximate the fracture(s). In many embodiments, the action of the closing of the slots (such as 116) during axial compression also serves to grip the bone and/or approximate the fracture(s). In other embodiments, wire or other fastening elements may be used to secure the device in place.

Figure 13:
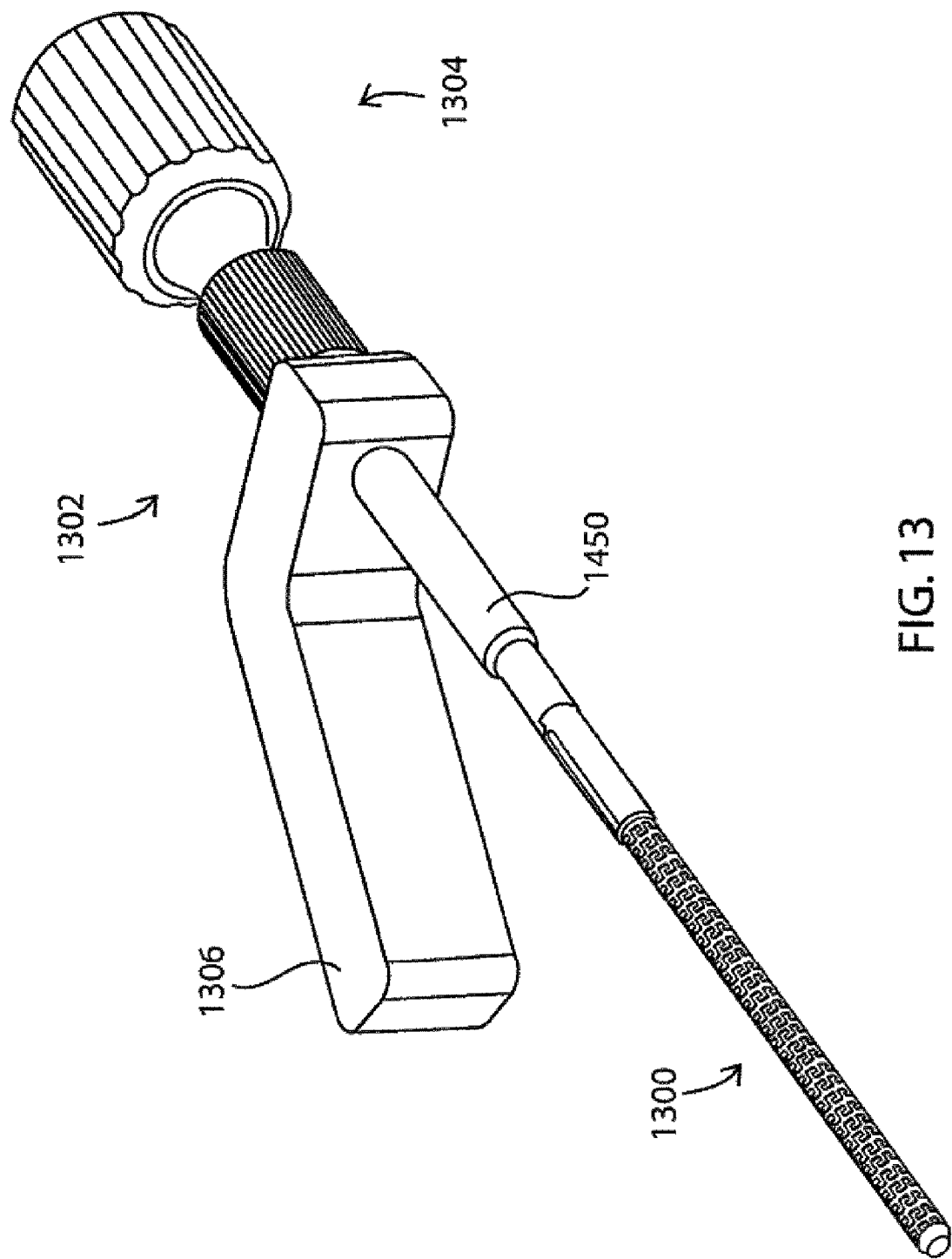
FIG. 13 is a perspective view showing another exemplary embodiment of a bone fixation device attached to tools that may be used for its insertion, deployment, and removal.

Referring now to FIGS. 13-21, another exemplary embodiment of a bone fixation device constructed according to aspects of the present invention will be described. FIG. 13 shows bone fixation device 1300 attached to an insertion and removal tool 1302 and actuation tool 1304. Insertion and removal tool 1302 in turn is mounted in a fixture arm 1306.

Figure 14:
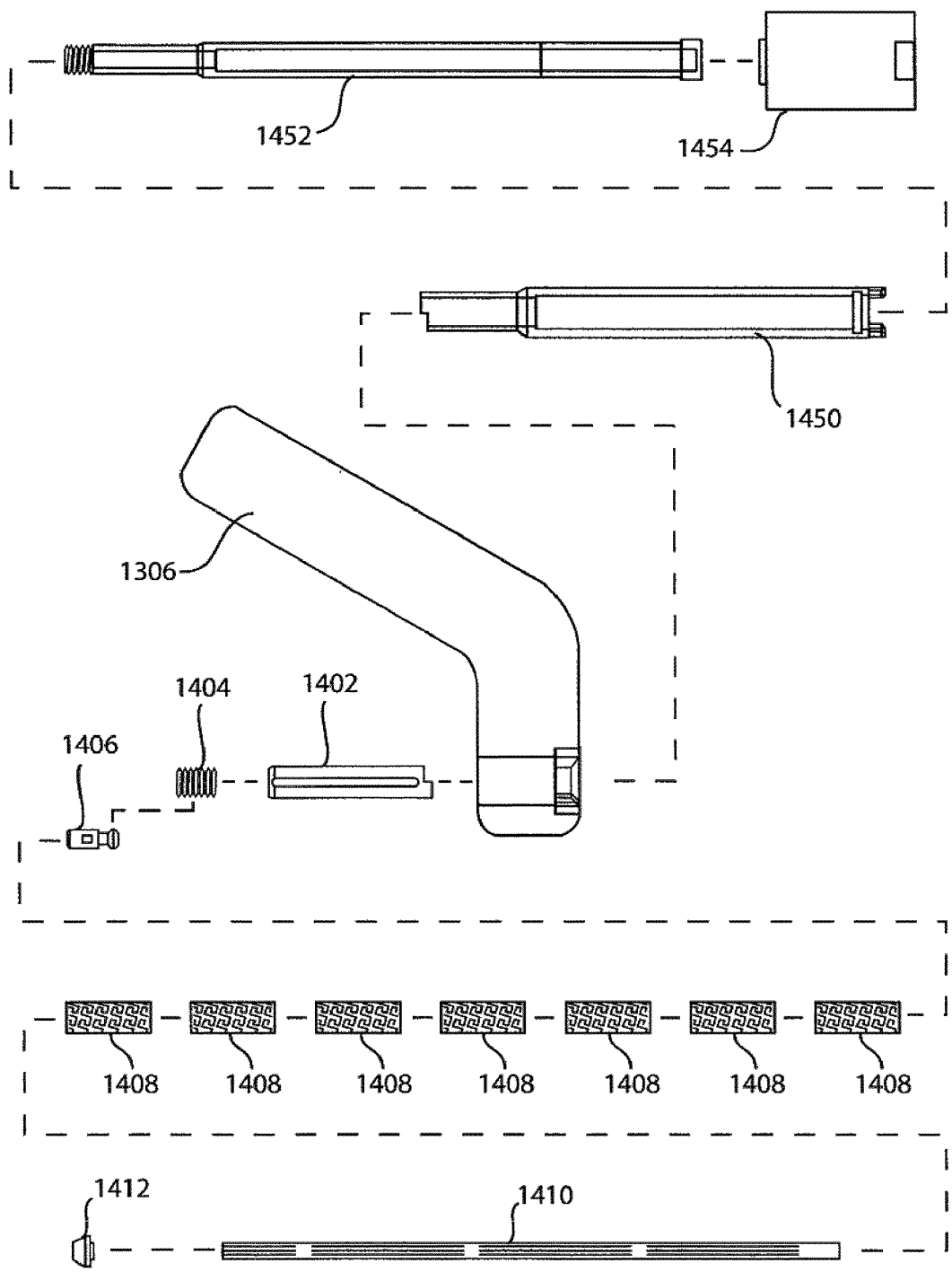
FIG. 14 is an exploded view showing the components of the bone fixation device and insertion/removal tool of FIG. 13.

Referring to FIG. 14, components of bone fixation device 1300 and insertion and removal tool 1302 are shown. In this exemplary embodiment, device 1300 comprises a hub 1402, actuation screw 1404, actuation shuttle 1406, flexible-to-rigid body member(s) 1408, tension member 1410, and end cap 1412. In alternative embodiments, additional, fewer, or a single flexible-to-rigid body member may be used. Insertion and removal tool 1302 comprises sleeve 1450, tube 1452, knob 1454, and may be mounted though fixture arm 1306.

Figure 15:
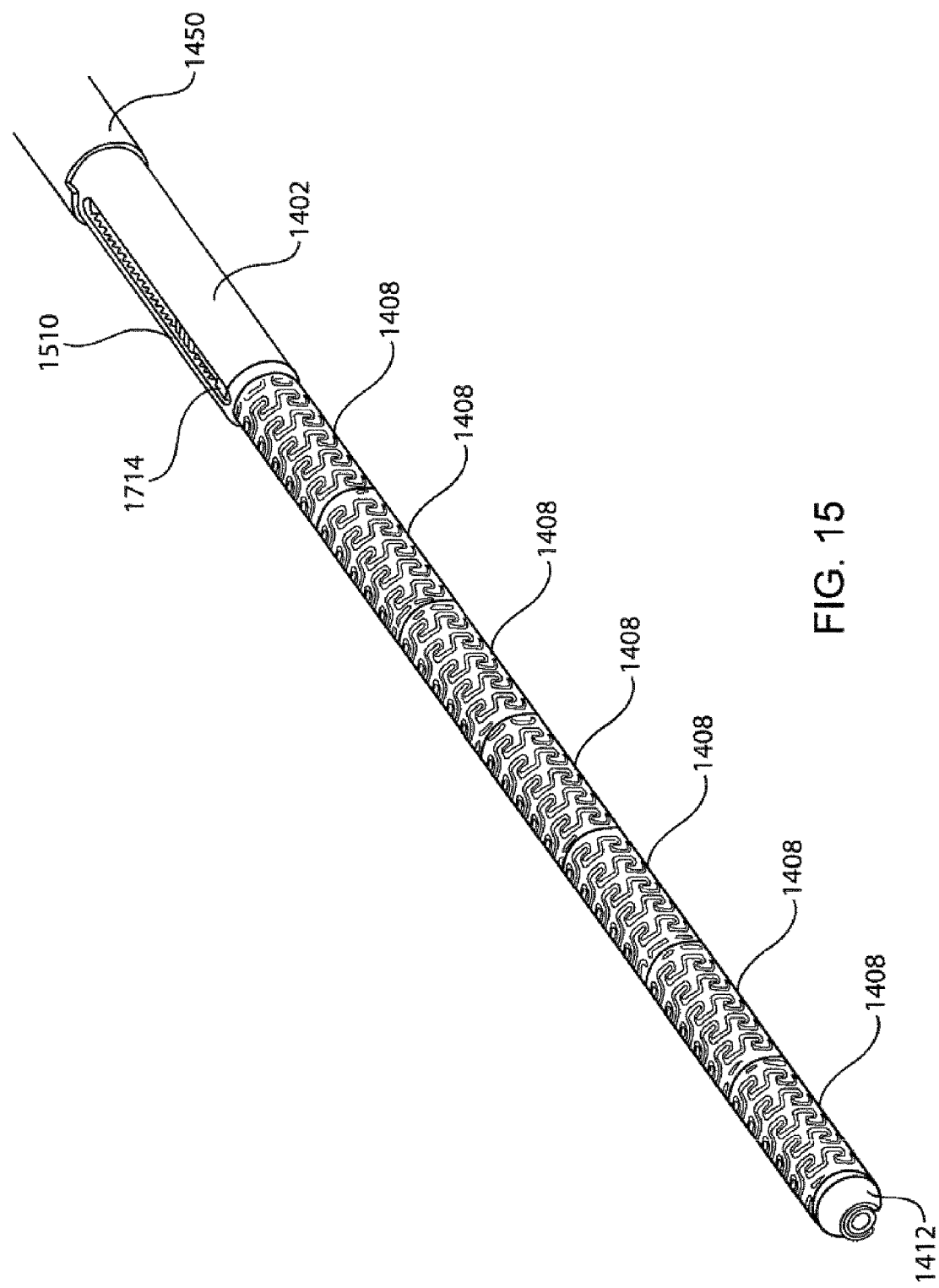
FIG. 15 is an enlarged perspective view showing the bone fixation device of FIG. 13.

Referring to FIG. 15, an enlarged perspective view of the assembled device 1300 is shown.

Figure 16:
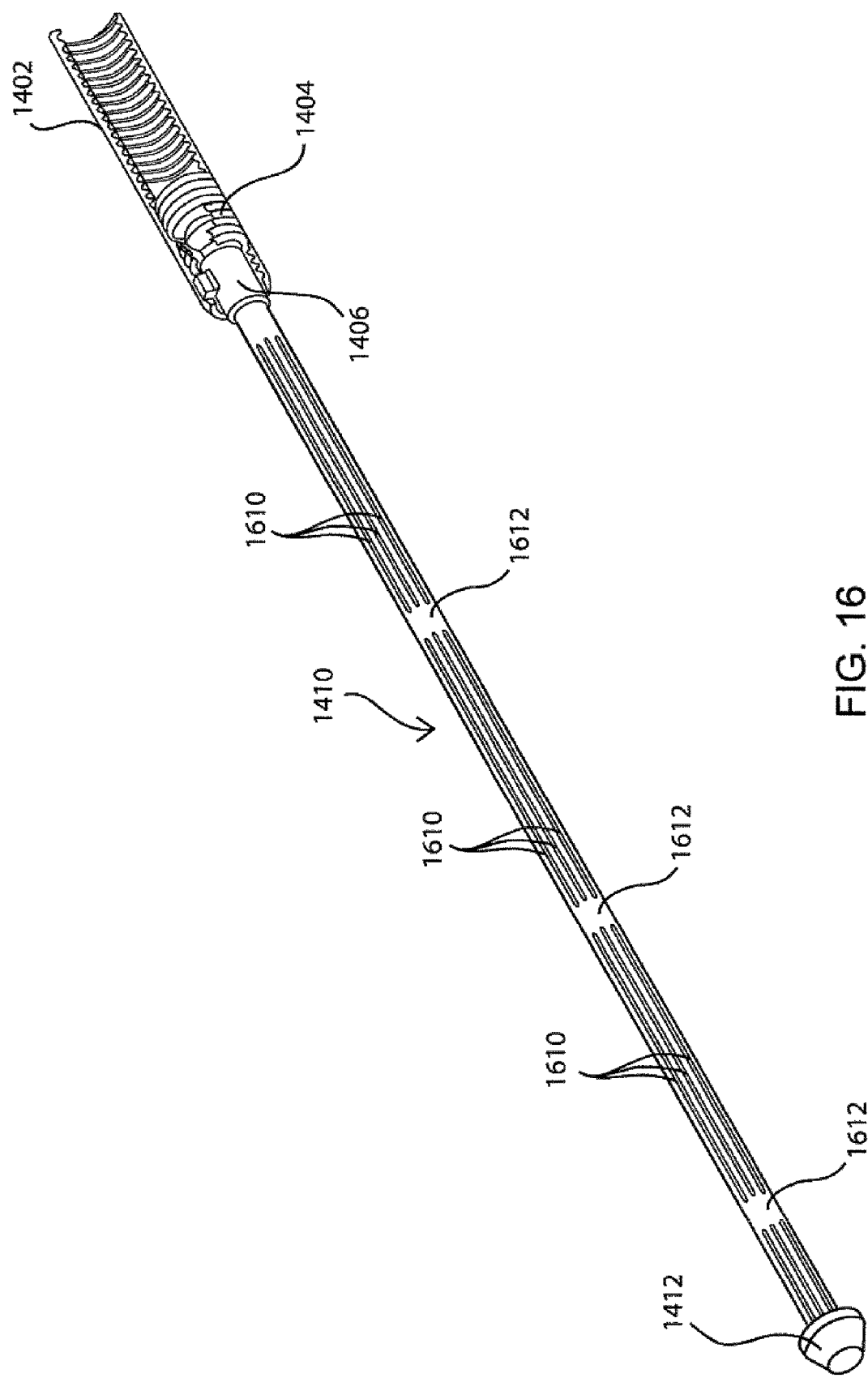
FIG. 16 is an enlarged, cut-away perspective view showing internal components of the device of FIG. 13.

Referring to FIG. 16, an enlarged, cut-away perspective view shows internal components of device 1300. End cap 1412, having the same nominal outer diameter as flexible-to-rigid body member(s) 1408 (shown in FIG. 15), is rigidly connected, such as by welding, to the distal end of tension member 1410. Tension member 1410 is sized to fit within flexible-to-rigid body member(s) 1408. Tension member 1410 may include a central longitudinal lumen, the purpose of which is later described. Tension member 1410 may also be provided with a series of longitudinal slots 1610 through its wall thickness to allow it to be very flexible. Solid ring portions 1612 may be interspersed between the series of slots 1610 to retain the tubular shape and torsional rigidity of tension member 1410. In other embodiments (not shown), the tension member is formed from one or more wires or cables, which may be bundled together, to be strong in tension while being flexible in bending.

Figure 17C:
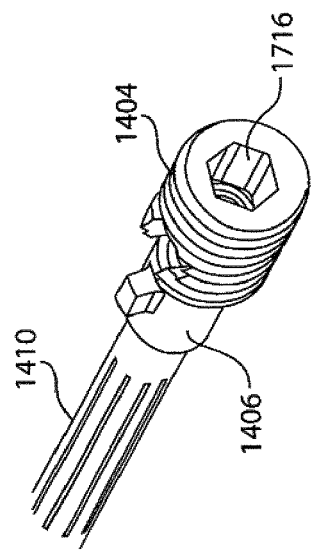
FIGS. 17A-17D are enlarged perspective views showing details of various components of the device of FIG. 13.
Figure 17D:
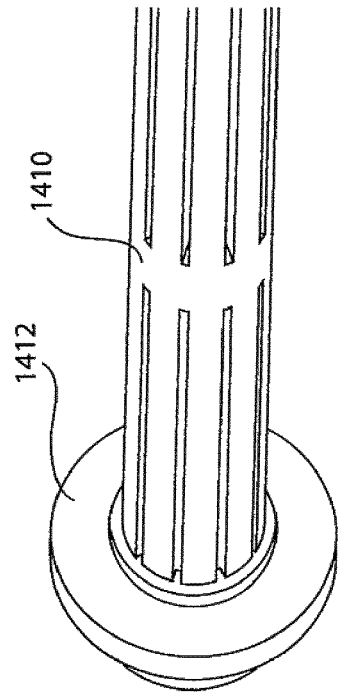
Figure 17B:
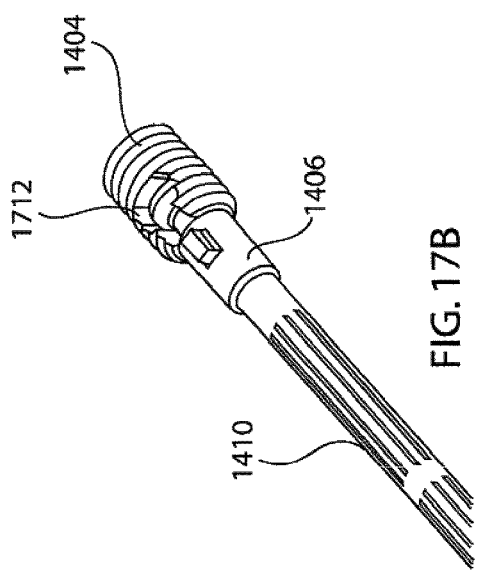
Figure 17A:
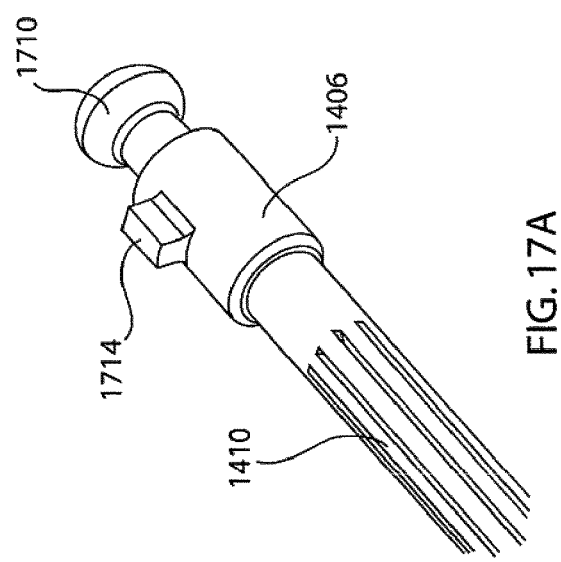
Figure 18:
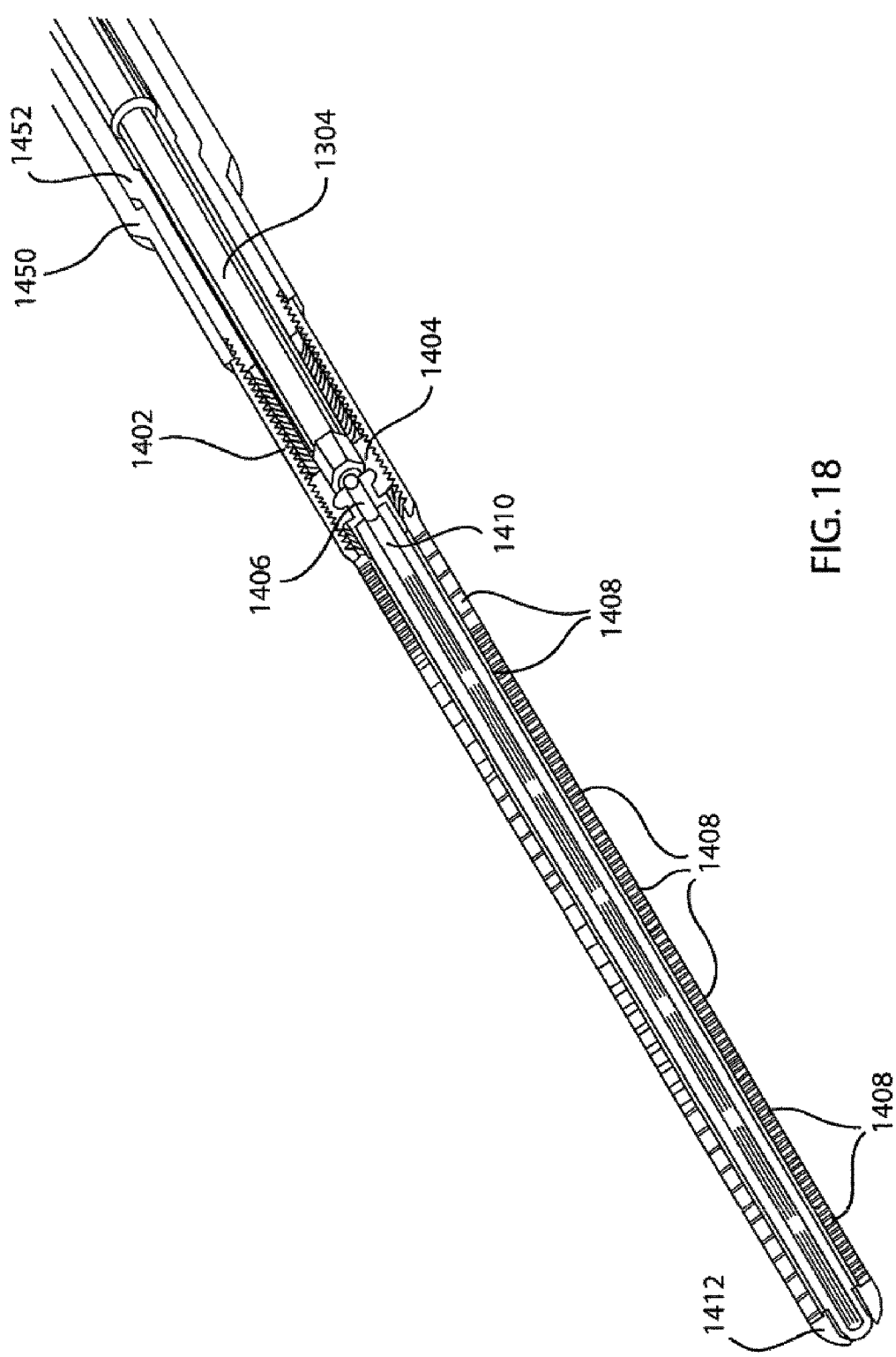
FIG. 18 is a longitudinal cross-section view showing the device and a portion of the tools of FIG. 13.

Actuation shuttle 1406 is attached to the proximal end of tension member 1410, such as by welding. Actuation shuttle 1406 includes a knobbed end 1710, as best seen in FIG. 17A. Knobbed end 1710 is configured to be received within mating keyhole 1712 in one side of actuation screw 1404, as best seen in FIGS. 17B and 17C. Actuation shuttle 1406 may also include a radially-protruding tab 1714, as best seen in FIG. 17A. Tab 1714 is sized to slide in a longitudinal slot 1510 in device hub 1402, as best seen in FIG. 15, to allow actuation shuttle 1406 to move axially without rotation. With actuation shuttle 1406 rotatably received in actuation screw 1404, which in turn is threadably engaged with hub 1402, the distal end of actuation tool 1304 may be received (as best seen in FIG. 18) in a keyed recess 1716 (best seen in FIG. 17C) of actuation screw 1404. Turning actuation screw 1404 with actuation driver 1304 causes actuation screw 1404, and with it actuation shuttle 1406, to move axially with respect to hub 1402. As actuation shuttle 1406 moves in a proximal direction (away from distal end cap 1412), a tensile force is imparted to tension member 1410, causing flexible-to-rigid body member(s) 1408 to be axially compressed between end cap 1412 and hub 1402 (see FIGS. 15 and 16). As previously described, this compression causes body member(s) 1408 to become substantially rigid, and to take on a predetermined shape, as will be more fully described below.

Figure 17E:
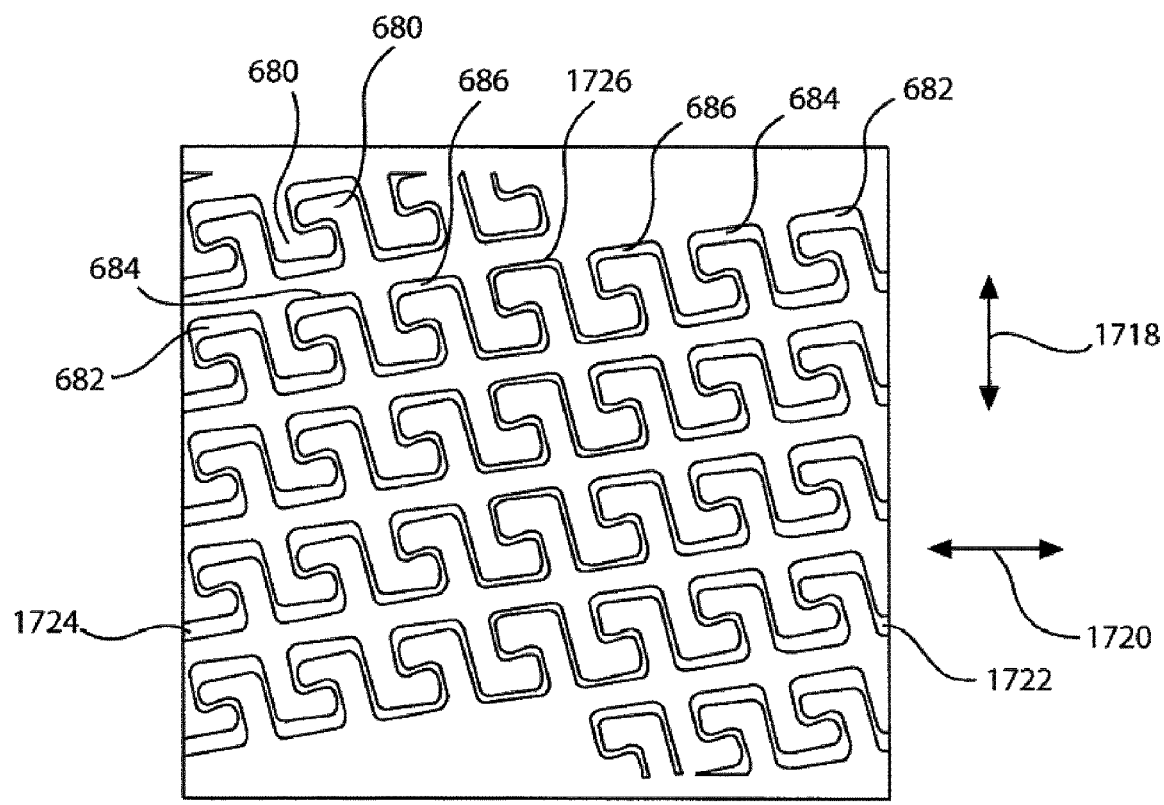
FIG. 17E is a plan view showing an exemplary interlocking pattern that may be used in the device of FIG. 13.

Referring to FIG. 17E, a plan view of an interlocking pattern is shown. The pattern has the same interlocking L-shaped features 680 as the flexible-to-rigid body member 1408 shown in FIGS. 6G and 6H described briefly above. In other words, FIG. 17E represents the pattern that would result if the body member 1408 were slit along one side in a longitudinal direction, unrolled and laid flat. Arrows 1710 in FIG. 17E indicate the longitudinal or axial direction of the pattern, while arrows 1712 represent the tangential direction. As can be seen, the pattern is formed by a continuous helical cut, such that gap 1722 on one side of the pattern connects with gap 1724 on the other side of the pattern when the pattern is formed on a tubular structure. While a single helical cut is shown, other embodiments may employ two or more helical cuts running in parallel around the tube. Pattern gaps may be formed by laser cutting, punching, milling, etching, sawing, electro-discharge machining, or other material removal or material addition processes. Patterns may be formed on a tubular structure, or on a generally flat substrate which is then configured into a tubular structure.

As briefly mentioned above in conjunction with FIG. 6G, the interlocking pattern may utilize gaps that narrow along one side of the tube (shown in the center of FIG. 17E) and widen along the other side of the tube (shown at the sides of FIG. 17E). In this exemplary pattern, gaps 682 are wider than gaps 684, which in turn are wider than gaps 686, which in turn are wider than gap 1726. As the pattern is compressed in an axial direction when formed on a tubular structure, the features adjacent the wider gaps (e.g. 682) will move farther than the features adjacent the narrower gaps (e.g. 1726) as the gaps are closed. Since one side of the tube is compressing more than the opposite side, the tube forms a curve that is concave on the side having the widest gaps.

Figure 19:
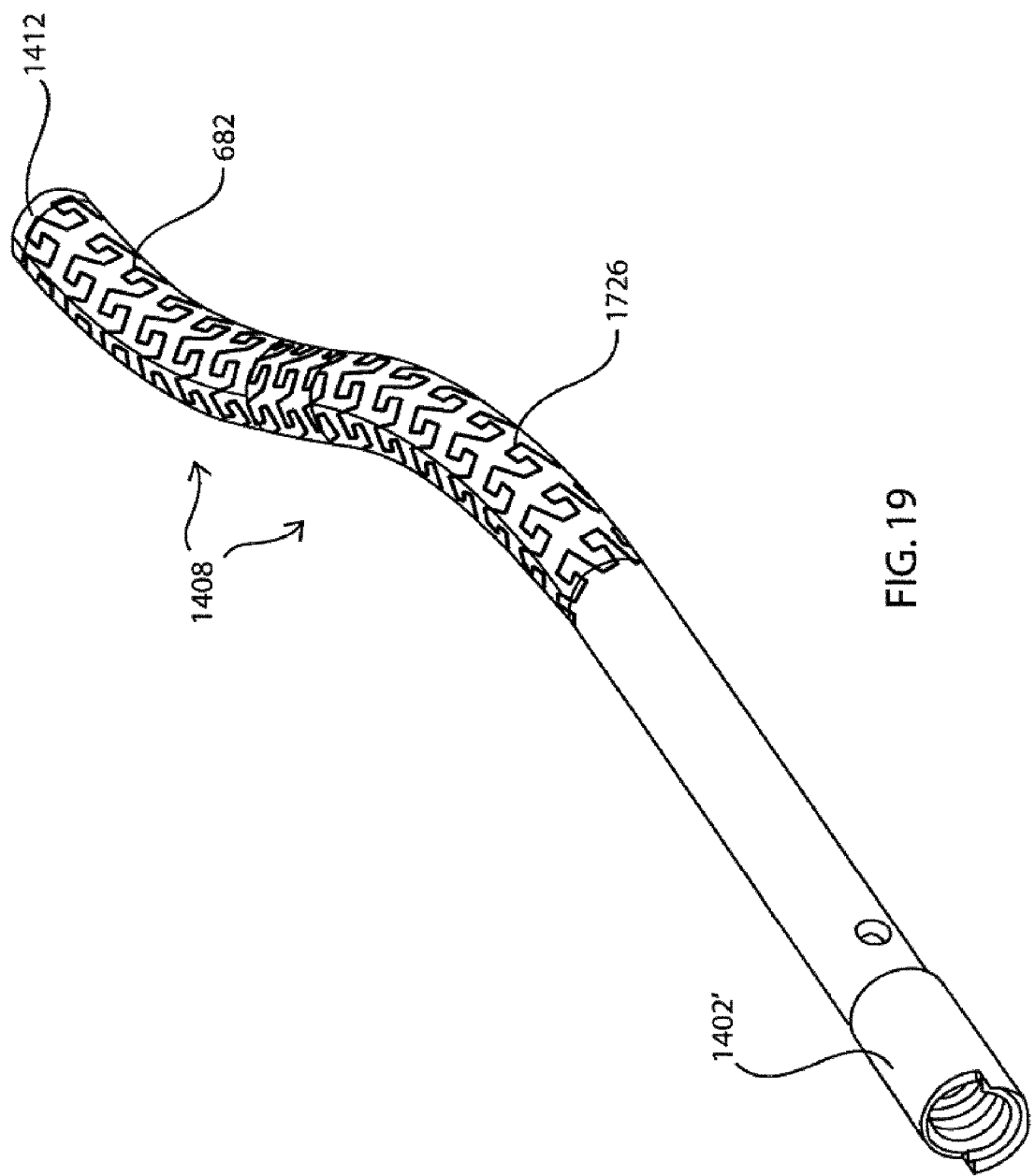
FIG. 19 is a perspective view showing the device of FIG. 13 in a deployed state.

Referring again to FIGS. 14 and 15, and also to FIG. 18, if all of the flexible-to-rigid body members 1408 are oriented with their widest pattern gaps on one side of the device 1300, the flexible-to-rigid portion will take on a single curved shape. If the body members 1408 toward the distal end are all oriented with their widest pattern gaps on one side, and the body members 1408 toward the proximal end are all oriented with their widest gaps on the opposite side, a compound or S-shaped curve will result, as shown in FIG. 19. If the orientation of each successive body member is alternated from one side to the other and back again, a rapidly undulating curve will result. If the orientation of each successive body member is changed in phase, for example by 90 degrees, from the orientation of the previous body member, a helical arrangement of the overall flexible-to-rigid body portion may be achieved. It can be appreciated that by changing the orientation of the gap thicknesses, essentially any desired three-dimensional curve may be obtained to suit the particular purpose. For example, the rapidly undulating curve described above may be more useful in some circumstances for allowing a bone fixation device to gain purchase within a relatively straight intramedullary canal. A body member having a compound curve can be useful in a bone fixation device that is designed to be inserted in a radius or an ulna, as these bones curve in more than one plane simultaneously. A bone fixation device having an S-shaped curve is useful in bones that have S-shaped portions, such as the clavicle.

It should be noted that in addition to varying the gap orientation, the relative change in gap width may be varied to produce curves of different radii. For example, one portion of a flexible-to-rigid body may have the same gap width around its circumference to produce a straight section, another portion may have a relatively small change in gap width to produce a large radius of curvature, while yet another portion may have a larger change in gap width around its circumference to produce a small radius of curvature. In some embodiments, such as shown in the accompanying figures, the device may employ a series of individual body members 1408 that together form an overall flexible-to-rigid body portion. Alternatively, it should be noted again that a continuous complex pattern similar to that formed by the multiple body sections described above may be formed on a single tubular structure. Additionally, interlocking or non-interlocking features other than the L-shaped features 680 may be used in addition to or instead of features 680.

Figure 20:
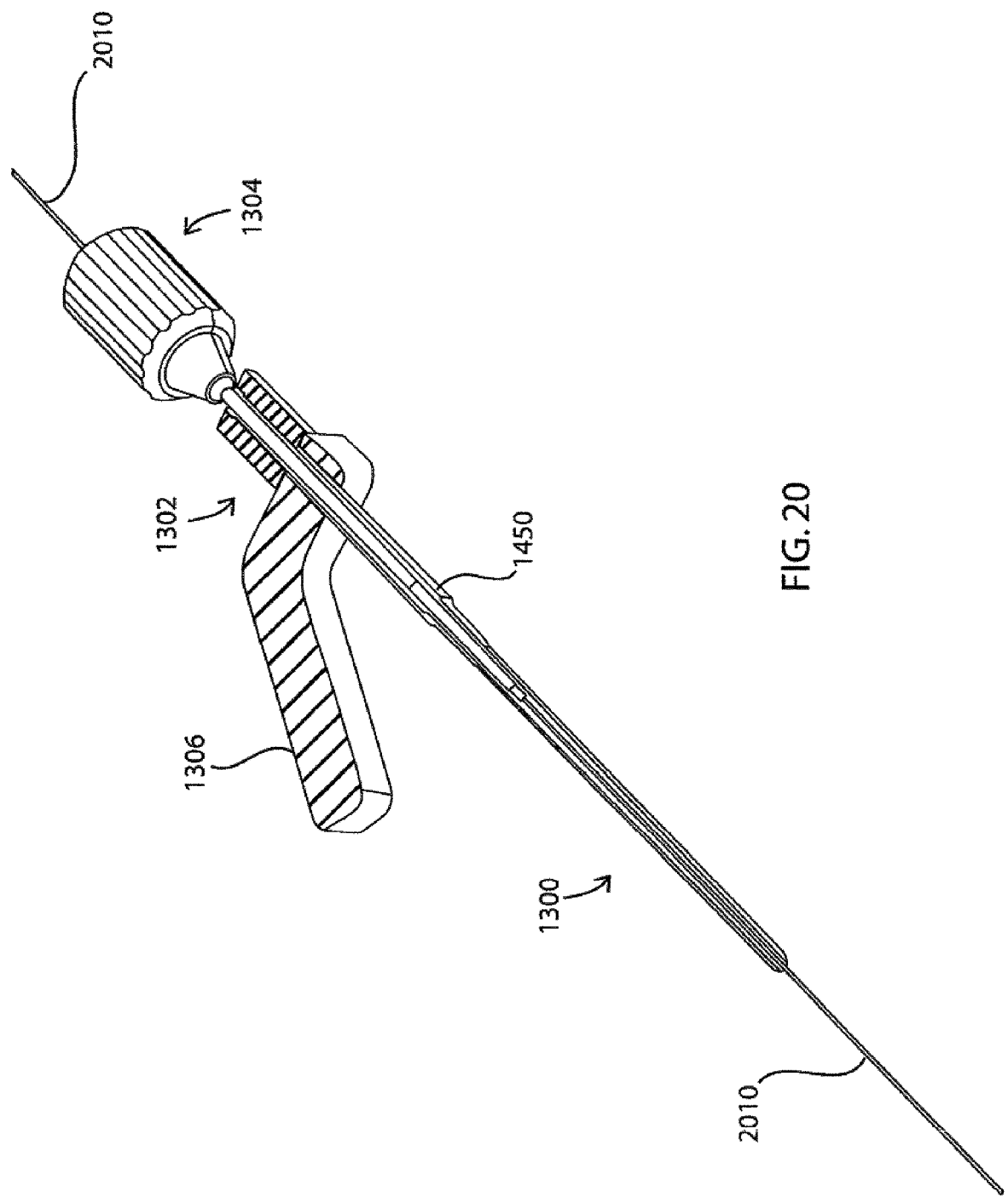
FIG. 20 is a cut-away perspective view showing the device and tools of FIG. 13 with a guide wire inserted therethrough.
Figure 21:
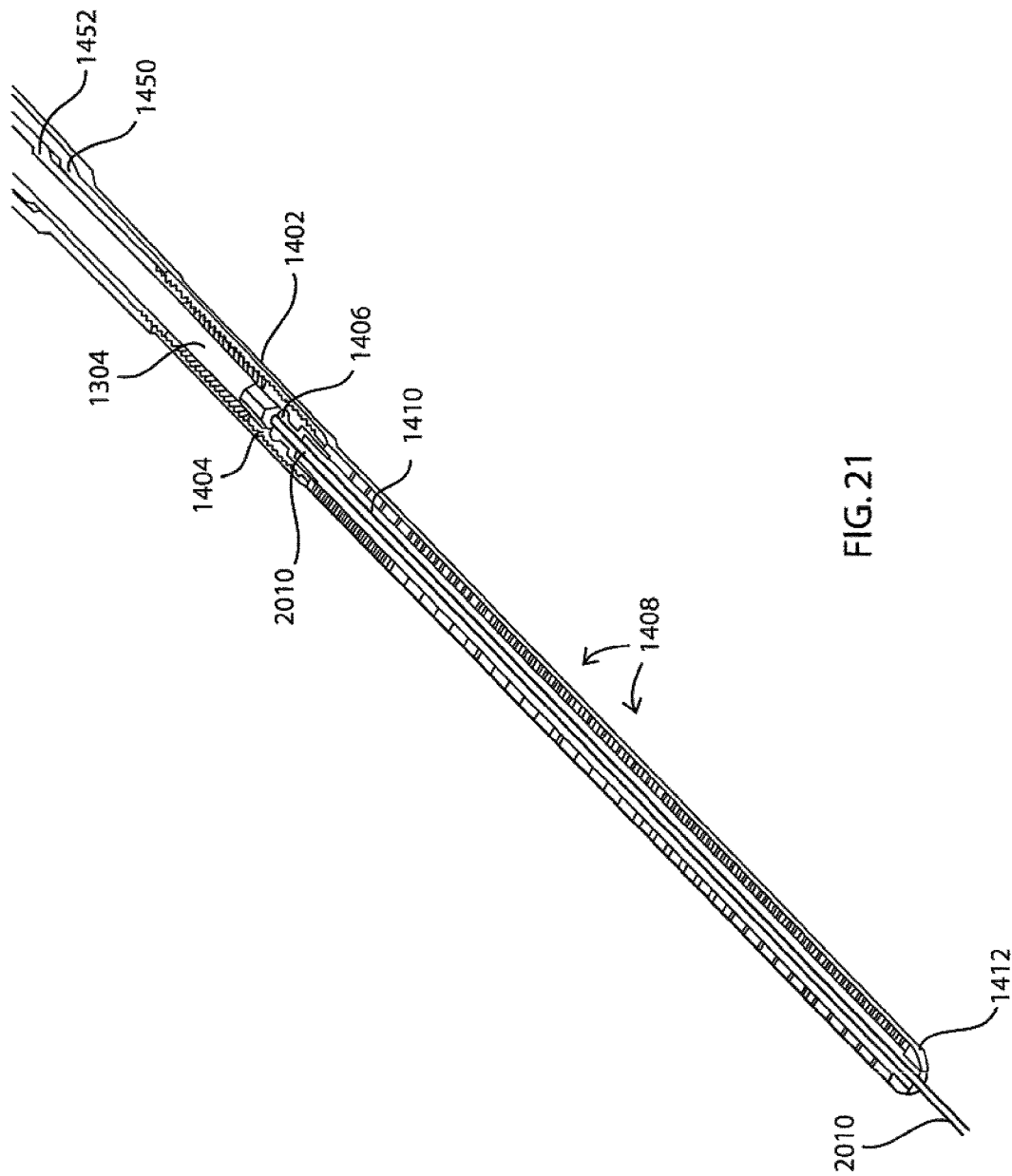
FIG. 21 is an enlarged cross-section view showing the device, tools and guide wire of FIG. 20.

Referring to FIGS. 20 and 21, use of the bone fixation device 1300 and associated tools with a guide wire 2010 is described. As described above and shown in the accompanying figures, each of the central components of device 1300 has an axial lumen extending therethrough. Similarly, the central components of actuation tool 1304 have an axial lumen extending therethrough. This arrangement permits device 1300, insertion/removal tool 1302, and/or actuation tool 1304 to be slid, either individually or together, over guide wire 2010.

In some bone fixation operations, it is advantageous to first introduce a guide wire into the intramedullary space of a bone before inserting a bone fixation device 1300, and in some cases before preparing the intramedullary canal for receiving device 1300. According to aspects of the invention, in some methods an access incision or puncture is made in the tissue surrounding a bone. A pilot hole may then be drilled in the bone to gain access to the intramedullary canal. Guide wire 2010 may then be introduced through the pilot hole (or in some cases without a pilot hole) into the intramedullary space. Guide wire 2010 may be further advanced through the canal and across a fracture site or sites, lining up bone fragments along the way. Introduction of guide wire 2010 may take place with the aid of fluoroscopy or other imaging technique.

After guide wire 2010 is inserted into a target bone, various burs, cutters, reamers, trocars, and/or other bone forming or aligning tools may be alternately advanced over guide wire 2010. One an interior bone space has been prepared (if desired) to receive bone fixation device 1300, device 1300 along with insertion/removal tool 1302 and actuation tool 1304 may be advanced over guide wire 1210. Insertion/removal tool 1302 may first be inserted in fixture arm 1306, which in turn may be fastened to external fixtures or used as a handle to assist in steadying and aligning device 1300 during insertion and actuation. Device 1300 may then be advanced along guide wire 2010 and into position within the bone. The guide wire may occupy a central lumen of the device along its longitudinal axis. The guide wire may slide along openings in the outer diameter surface of the device in an analogous fashion to the eyelets of a fishing rod. These lumen may be intra-operatively or post-operatively available for the delivery of other devices, therapies to the bone, or tools.

Deployment of device 1300 may be accomplished by rotating actuation tool 1304. As previously described, such rotation moves actuation screw 1404 in a proximal direction and ultimately causes a compressive load to be placed on flexible-to-rigid body portion(s) 1408. This in turn causes flexible-to-rigid body portion(s) 1408 to take on a desired shape and become generally rigid to secure device 1300 against the interior surfaces of the bone. Actuation tool 1304 may include a torque measuring or limiting mechanism to help ensure that a predetermined or desired amount of force is being applied from deployed device 1300 against the bone. Device 1300 may be secured with additional methods, such as with bone screw(s), K-wire(s) and the like.

Actuation tool 1304 and insertion/removal tool 1302 may be removed together or individually. Actuation tool 1304 is removed be pulling in a proximal direction to disengage its distal tip from recess 1716 within actuation screw 1404. Insertion/removal tool 1302 is disengaged from device 1300 by turning the knob at the proximal end of tool 1302. This unscrews the externally threaded distal tip of tube 1452 of tool 1302 from the internally threaded bore of hub 1402, as best seen in FIG. 21. The guide wire 1210 may then be removed (or at an earlier time if desired), and the access wound(s) closed. It will be appreciated that these same tools and the reverse of these methods may be used to remove device 1300, if desired, during the initial procedure or at a later time.

Figure 22:
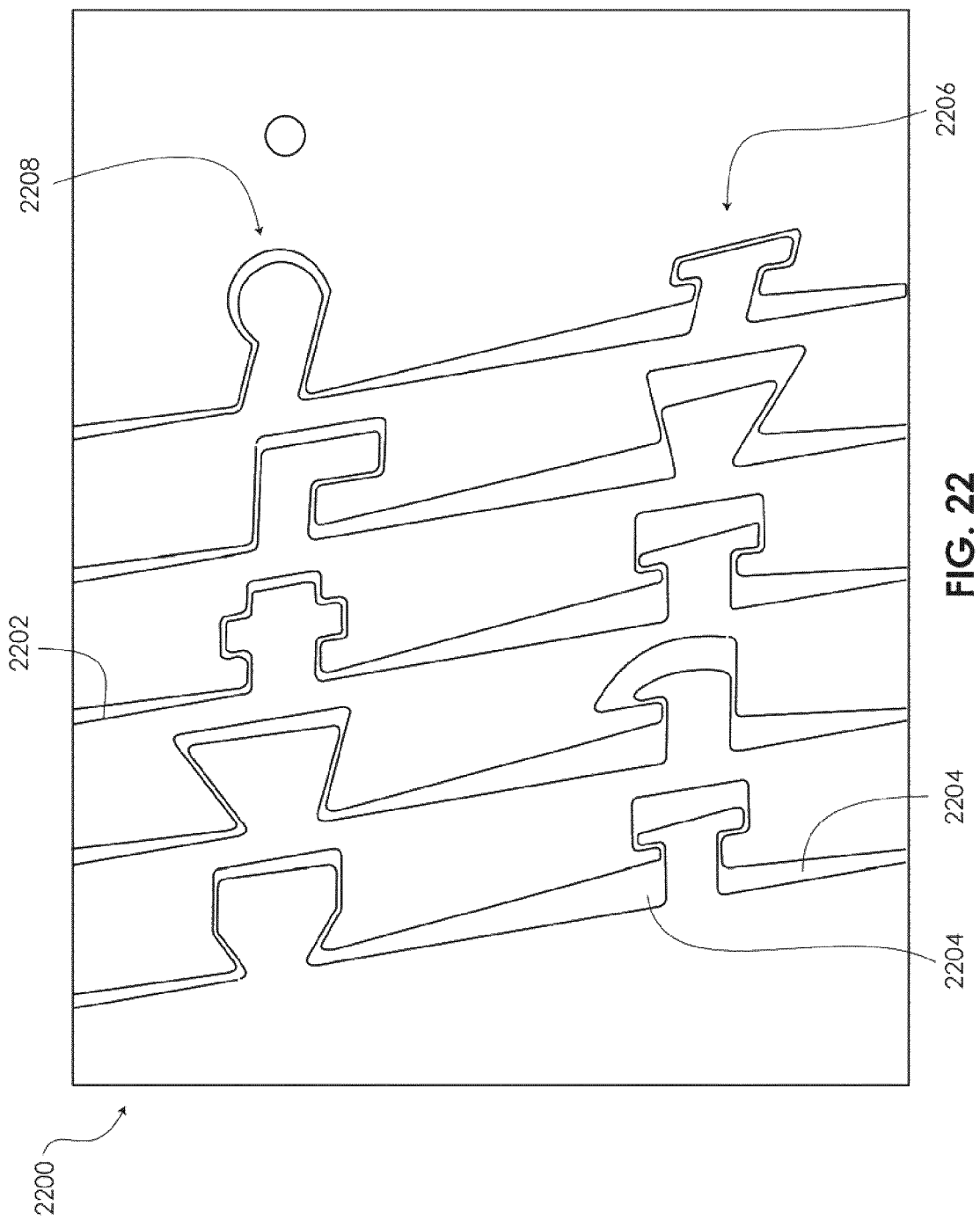
FIGS. 22 and 23 are plan views showing exemplary patterns that may be used in the flexible-to-rigid body portions of bone fixation devices.
Figure 23:
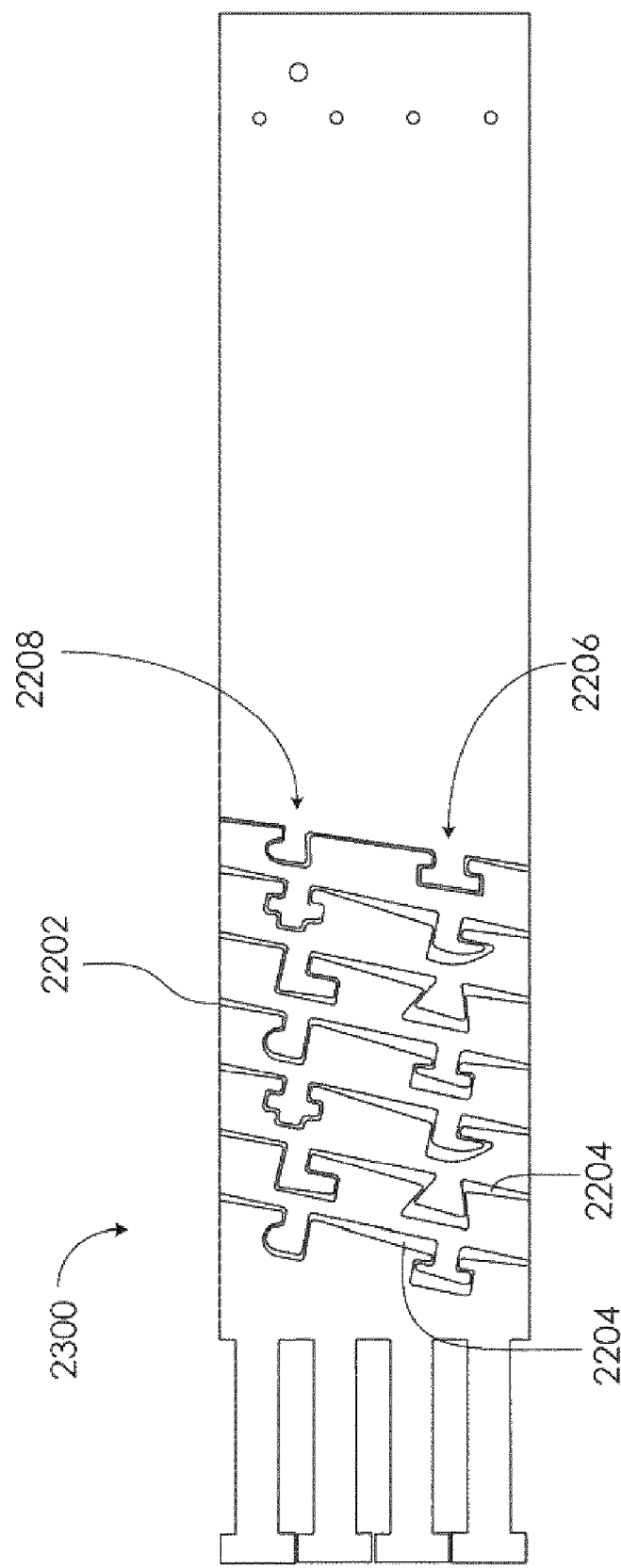

Referring to FIGS. 22 and 23, additional exemplary patterns are shown that may be used in the flexible-to-rigid body portions of bone fixation devices. Non-repeating pattern 2200 includes ten different interlocking shape pairs along a helical slit 2202, none of which are the same. In this example pattern 2200, there are two interlocking shape pairs located along each revolution of helical slit 2202, such that when the pattern is formed on a tube, the two pairs are on opposite sides of the tube. Alternatively, a pattern of interlocking shapes may repeat every revolution of the helical slit 2202, every partial revolution, or over the course of more than one revolution. For example, a series of six different interlocking shape pairs may repeat every three revolutions of helical slit 2202, as shown in the exemplary pattern 2300 of FIG. 23.

It can be seen in FIGS. 22 and 23 that patterns 2200 and 2300 include ramped portions 2204 along each revolution of helical slit 2202 where the slit gets progressively wider. Additionally, helical slit 2202 forms a wider gap adjacent to the lower set of interlocking shape pairs 2206 than it does adjacent to the upper set of shape pairs 2208. These ramped portions 2204 and wider gaps allow patterns 2200 and 2300 to axially compress to a greater extent in one area (the lower part of FIGS. 22 and 23) than in another area (the upper part of FIGS. 22 and 23). Accordingly, when patterns 2200 and 2300 are applied to a tubular member, the member will form a curve when axially compressed, as previously described.

Figure 24A:
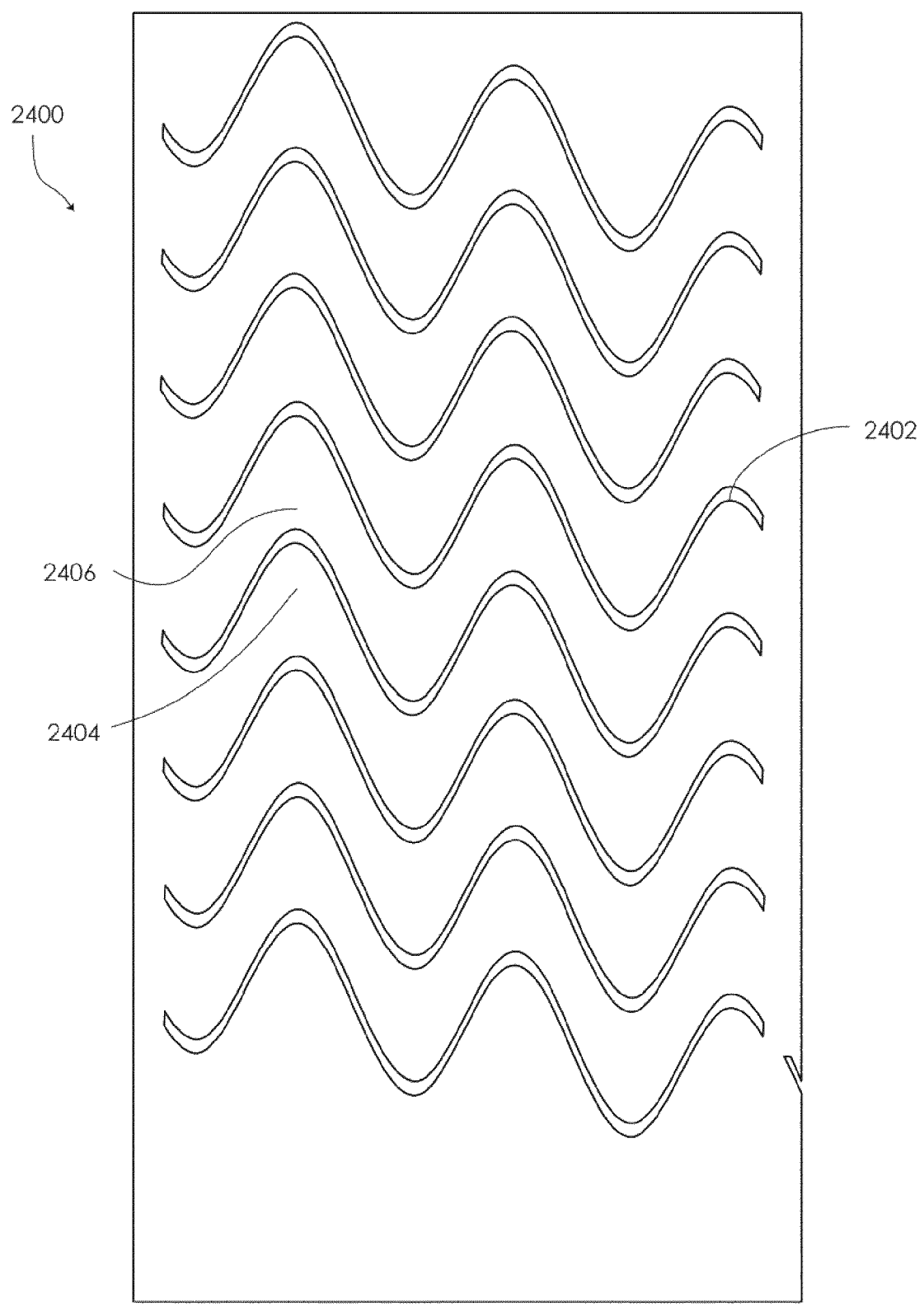
Figure 28A:
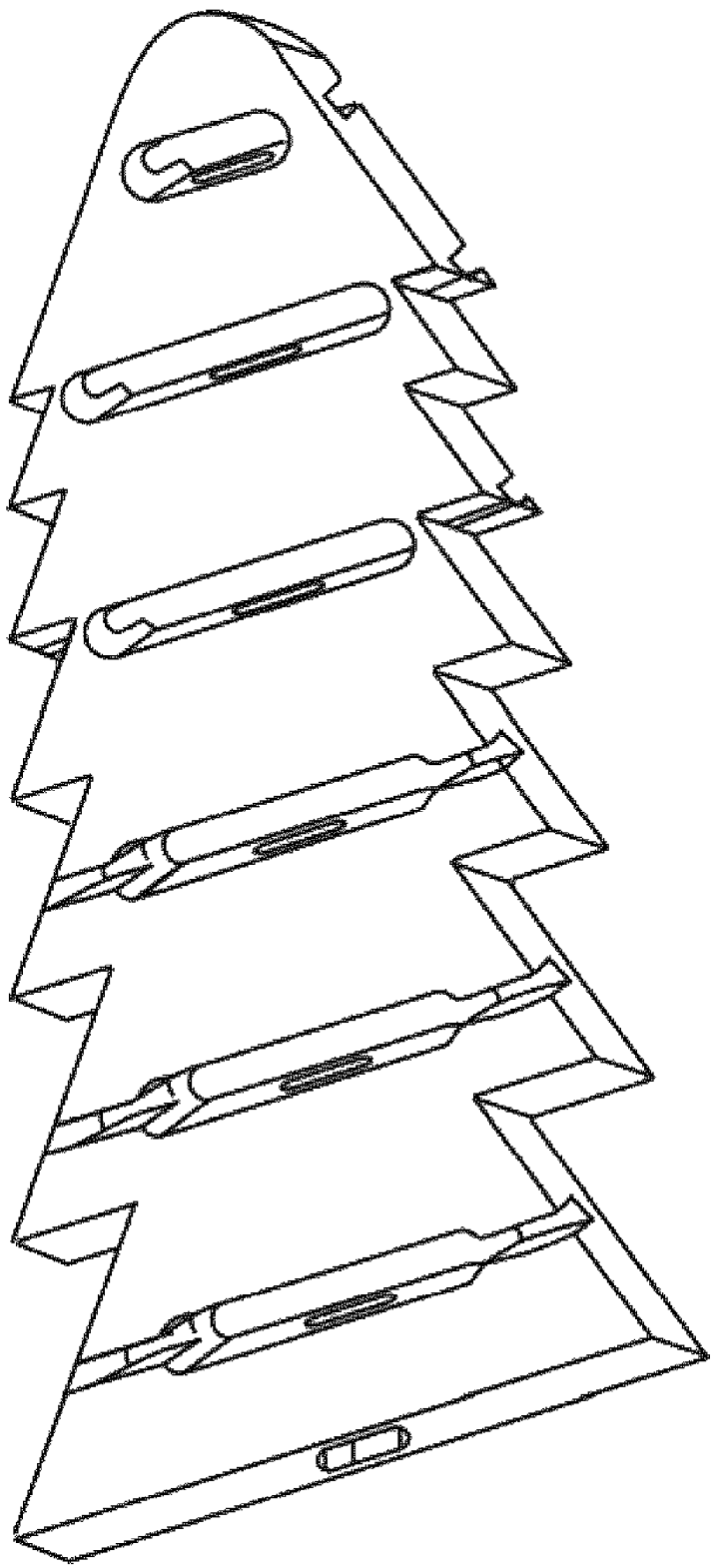
Figure 29A:
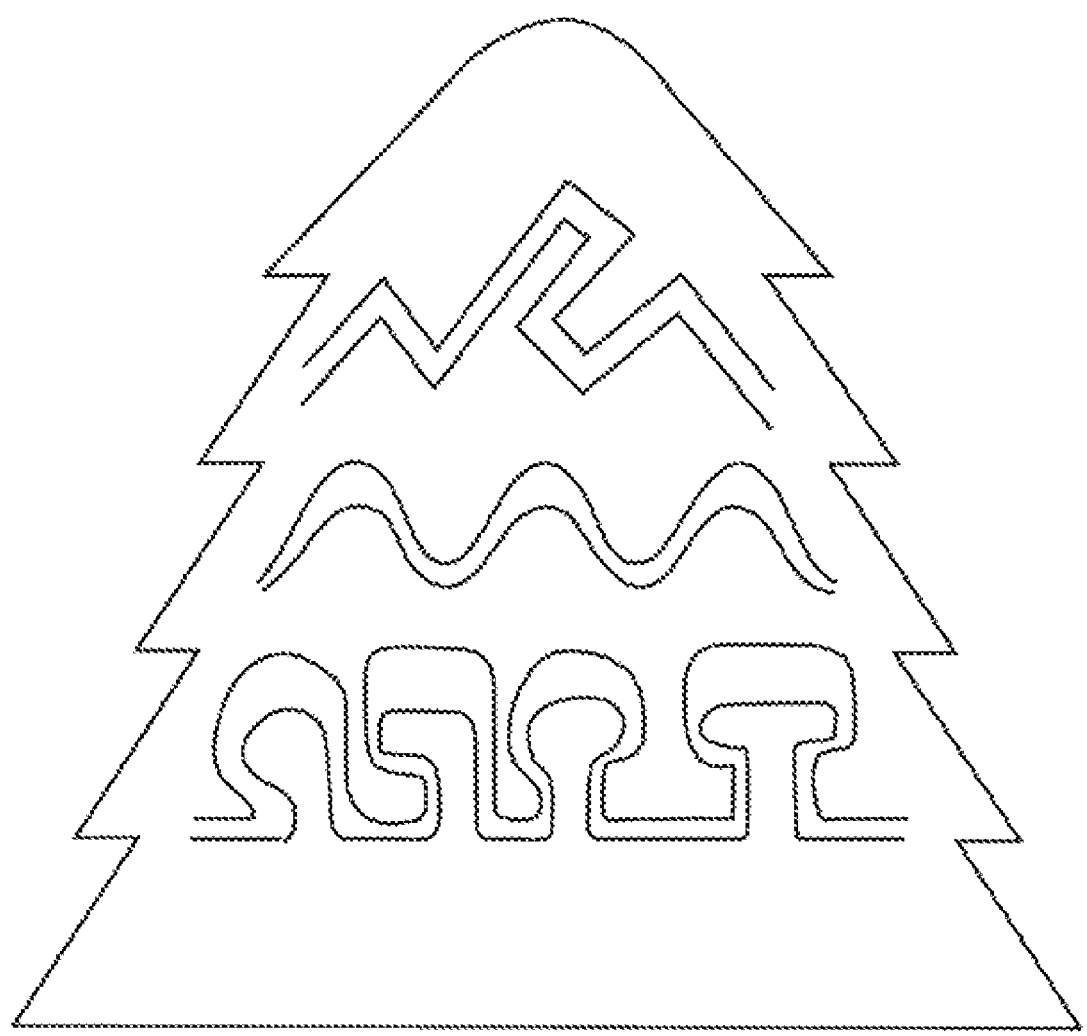
FIGS. 29A-29B show an alternative embodiment of a bone fixation device.
Figure 29B:

Referring to FIGS. 24A-24H, an alternative flexible-to-rigid body portion pattern 2400 will now be described. Pattern 2400 is formed by superimposing a sinusoidal pattern on helical slit 2402. Helical slit 2402 may be continuous, or it may be formed in individual segments with solid sections in between, as shown in FIG. 24A. In can be seen in FIG. 24A that the peak 2404 on one side of slit 2402 nests within trough 2406 on the opposite side of slit 2402.

Referring to FIG. 24B, it can be seen that slit 2402 may be formed at an angle relative to tube wall 2408 rather than being perpendicular to tube wall 2408 and the longitudinal axis of the device. In this manner, a ramp is formed on the peak side 2404 of slit 2402 and another ramp is formed on the trough side 2406. In other embodiments, a ramp may be formed only on the peak side 2404 or only on the trough side 2406. In some embodiments, only a portion of one or both sides is ramped or rounded. When the flexible-to-rigid body portion is axially compressed, the ramps cause at least a tip portion 2410 of peak 2404 to ride up on trough 2406 and extend radially outward, as shown in FIG. 24C. This tip portion may be configured to bite into the surrounding bone. Even if each extending tip 2410 only provides a small amount of gripping force, with a large number of tips 2410 engaging the bone a large amount of gripping power can be generated to hold the device within the bone. In the embodiment shown in FIG. 24C, only a portion of the tube wall 2408 on one side of slit 2402 rides above the tube wall 2408 on the opposite side of slit 2402. In other embodiments, one side of tube wall 2408 may ride up and completely onto the opposite side.

Referring to FIGS. 24D-24G, tip 2410 need not take the shape of a sinusoidal wave. The tip may be V-shaped (FIG. 24D), semicircular (FIG. 24E), chisel-shaped (FIG. 24F), square (FIG. 24G), notched (FIG. 24H), or have another shape in order to effectively grip the surrounding bone. Tips of a particular device may have the same shape on every tip, or multiple tip shapes may be used on one device.

While bone fixation devices having circular cross-sections have been shown and described, other cross-section shapes according to aspects of the invention may be useful in some circumstances. In some embodiments, a triangular cross-section may be used, as its sharp edges can aid in gripping the surrounding bone. Non-circular cross sections may be used in applications where a particular combination of area moments of inertia is desired. Particular non-circular cross sections may be chosen for their optimization in certain anatomies, or for aiding in manufacturability of a bone fixation device. In some embodiments, the cross section of the bone fixation device is circular, oval, elliptical, triangular, square, rectangular, hexagonal, octagonal, semi-circular, crescent-shaped, star-shaped, I-shaped, T-shaped, L-shaped, V-shaped, or a combination thereof. In some embodiments, the cross section forms a polygon having any number of sides from 1 to infinity. In some embodiments, the cross-sections are tubular and in others they are solid. In some embodiments, the cross-section of the device can vary in size along it length, such as tapering from the proximal end to the distal end. FIGS. 25A-25D provide an example of an oval cross section, and FIGS. 26A-26D provide an example of a square cross-section.

In other embodiments, a solid rectangular geometry with an externally communicating stiffening member can be constructed. FIGS. 27A-27E, FIGS. 28A-28E and FIGS. 29A-29B describe three exemplary geometries. The external stiffener geometry of the device shown in FIGS. 27A-27E, and its resultant shape upon activation to its rigid state, are designed to allow insertion, match the anatomical configuration of the bone, and provide remediation of the malady of the bone, such as proximation and fixation of the fracture. The external stiffener geometry of the device allows removal upon deactivation. The devices shown in FIGS. 27 through 29 may be used for treatment of flat bones, such as those of the face, skull, scapula, and lateral clavicle.

In accordance with the various embodiments of the present invention, the device may be made from a variety of materials such as metal, composite, plastic or amorphous materials, which include, but are not limited to, steel, stainless steel, cobalt chromium plated steel, titanium, nickel titanium alloy (nitinol), superelastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In a further embodiment, there is provided a low weight to volume device deployed in conjunction with other suitable materials to form a composite structure in-situ. Examples of such suitable materials may include, but are not limited to, bone cement, high density polyethylene, Kapton®, polyetheretherketone (PEEK™), and other engineering polymers.

Once deployed, the device may be electrically, thermally, or mechanically passive or active at the deployed site within the body. Thus, for example, where the device includes nitinol, the shape of the device may be dynamically modified using thermal, electrical or mechanical manipulation. For example, the nitinol device may be expanded or contracted once deployed, to move the bone or other region of the musculo-skeletal system or area of the anatomy by using one or more of thermal, electrical or mechanical approaches.

It is contemplated that the inventive implantable device, tools and methods may be used in many locations within the body. Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle (proximal) or the medial malleolus (distal); for the fibula, at the neck of the fibula (proximal) or the lateral malleoulus (distal); the ribs; the clavicle; the phalanges; the bones of the metacarpus; the bones of the carpus; the bones of themetatarsus; the bones of the tarsus; the sternum and other bones, the device may be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention claimed is:

1. A bone fixation device comprising:
   a generally tubular body having a circumferential surface, an inner lumen, and a wall extending therebetween, the body being sized to fit within an intramedullary space within a bone, the body having a longitudinal axis;
   at least one radially expandable gripper disposed within the body for engaging a surface of the intramedullary space;
   an actuator comprising a distal actuator head, the distal actuator head comprising a ramped surface slideably disposed on an interior of the at least one radially expandable gripper, the actuator configured to outwardly actuate the at least one radially expandable gripper away from the longitudinal axis and away from the body;
   a slit through the body wall extending through at least one complete revolution around the circumferential surface and axially along at least a portion of the body; and
   a compression mechanism configured to apply an axial compression to the body to move the slit towards a closed position, thereby transforming the body from a generally flexible state to a generally rigid state.

2. The bone fixation device of claim 1 further comprising at least one pair of mating features formed by the slit, wherein one of the mating features is located on one side of the slit and the other mating feature is located on the opposite side of the slit.

3. The bone fixation device of claim 2 further comprising at least two pairs of mating features located within one revolution of the slit.

4. The bone fixation device of claim 2 further comprising at least five pairs of mating features located within one revolution of the slit.

5. The bone fixation device of claim 2 wherein the slit comprises a sinusoidal pattern that forms the pairs of mating features.

6. The bone fixation device of claim 2 wherein the mating features of at least one of the pairs interlock to limit axial expansion and contraction of the body, and to limit axial rotation in both directions of one part of the body relative to another.

7. The bone fixation device of claim 6 wherein the mating features comprise L-shaped protuberances extending from each side of the slit into mating L-shaped cavities in the opposite side of the slit.

8. The bone fixation device of claim 7 wherein the L-shaped protuberances on opposite sides of the slit directly interlock with each other.

9. The bone fixation device of claim 6 wherein the mating features comprise T-shaped protuberances extending from each side of the slit into mating T-shaped cavities in the opposite side of the slit.

10. The bone fixation device of claim 9 wherein the T-shaped protuberances on opposite sides of the slit directly interlock with each other.

11. The bone fixation device of claim 6 further comprising at least three pairs of interlocking features located within one revolution of the slit.

12. The bone fixation device of claim 6 further comprising at least seven pairs of interlocking features located within one revolution of the slit.

13. The bone fixation device of claim 1 wherein the slit comprises at least three revolutions.

14. The bone fixation device of claim 1 wherein the slit has a width that varies as it extends around the circumferential surface such that one portion of the body may axially compress more than another portion when the slit moves toward the closed position.

15. The bone fixation device of claim 1 further comprising at least two interdigitated slits extending along at least a portion of the body.

16. The bone fixation device of claim 1 wherein the compression mechanism is reversible, such that the axial compression can be removed thereby transforming the body from a generally rigid state to a generally flexible state.

17. The bone fixation device of claim 1 comprising at least four radially expandable grippers coupled to the body for engaging a surface of the intramedullary space.

18. The bone fixation device of claim 1 further comprising at least one screw hole extending radially at least partially through the body for receiving a bone screw to assist in securing the body within the intramedullary space.

19. A bone fixation device comprising:
   a generally tubular body having a circumferential surface, an inner lumen, and a wall extending therebetween, the body being sized to fit within an intramedullary space within a bone, the body having a longitudinal axis;
   at least one radially expandable gripper disposed within the body for engaging a surface of the intramedullary space;
   an actuator comprising a distal actuator head, the distal actuator head comprising a ramped surface slideably disposed on an interior of the at least one radially expandable gripper, the actuator configured to outwardly actuate the at least one radially expandable gripper away from the longitudinal axis and away from the body;
   a slit through the body wall extending around the circumferential surface and axially along at least a portion of the body, wherein the slit comprises at least one revolution;
   at least one pair of mating features formed by the slit and located within one revolution of the slit, wherein the mating features of each of the at least three one pair interlock to limit axial expansion and contraction of the body, and to limit axial rotation in both directions of one part of the body relative to another; and
   a compression mechanism configured to apply an axial compression to the body to move the slit towards a closed position, thereby transforming the body from a generally flexible state to a generally rigid state, the compression mechanism being reversible such that the axial compression can be removed, thereby transforming the body from a generally rigid state to a generally flexible state, and wherein the slit has a width that varies as it extends around the circumferential surface such that one portion of the body may axially compress more than another portion when the slit moves toward the closed position, thereby forming a curve in at least a portion of the body.

20. The bone fixation device of claim 19 further comprising at least one radially expandable gripper coupled to the body for engaging a surface of the intramedullary space.

21. A method of repairing a bone fracture comprising:
   providing an elongate fixation device having a longitudinal axis and at least a portion transformable between a generally flexible state and a generally rigid state, the transformable portion having a slit extending around at least one complete revolution around its circumference;

inserting the device in the generally flexible state into an intramedullary canal of the bone across the fracture;

actuating a compression mechanism on the device to move the slit towards a closed position, thereby transforming the device portion from the generally flexible state to the generally rigid state;

extending a radially expandable gripper disposed within the elongated fixation device away from the longitudinal axis by moving an actuator along the longitudinal axis, the actuator comprising a distal actuator head with a ramped surface slideably disposed on an interior of the radially expandable gripper; and engaging the radially expandable gripper to a surface of the intramedullary canal.

22. The method of claim 21 wherein the actuating step causes the portion transformable between the generally flexible state and the generally rigid state to change from a first shape to a second shape, the second shape enabling the device to grip at least one bone surface within the intramedullary space.

23. The method of claim 22 wherein the second shape is similar but not identical to a shape of the intramedullary space.

24. The method of claim 22 wherein the first shape is generally straight and the second shape is curved.

25. The method of claim 21 further comprising actuating a radially expanding gripper after the inserting step.

26. The method of claim 25 wherein the actuation of the compression mechanism and the actuation of the gripper are accomplished in a single step.

27. The method of claim 21 further comprising reversing the compression mechanism to transform the device portion from the generally rigid state to the generally flexible state, and removing the device from the bone.

28. The method of claim 21 wherein the transformable portion of the device comprises a plurality of pairs of mating features formed by the slit.

29. The method of claim 28 wherein the mating features of at least one of the pairs interlock to limit axial expansion and contraction of the transformable portion, and to limit axial rotation in both directions of one part of the transformable portion relative to another.

* * * * *

UNITED STATES PATENT AND TRADEMARK OFFICE
CERTIFICATE OF CORRECTION

PATENT NO. : 8,287,541 B2  
APPLICATION NO. : 12/482406  
DATED : October 16, 2012  
INVENTOR(S) : Nelson et al.

Page 1 of 1

It is certified that error appears in the above-identified patent and that said Letters Patent is hereby corrected as shown below:

In column 2 (page 5 item 56) at line 29-31, Under Other Publications, delete "Nelson et al.; U.S. Appl. No. 12/482,395......filed Jun. 10, 2009." and insert the same on Page 5, Col. 2, Line 30, below "filed Jun. 10, 2009." as a new Entry.

In column 1 at line 59, After "reference" insert --.--.

In column 2 at line 61, Change "and or" to --and/or--.

In column 3 at line 26, Change "Raftopolous" to --Raftopoulos--.

In column 7 at line 25, Change "visa" to --vice--.

In column 7 at line 49, Change "visa" to --vice--.

In column 10 at line 55-56, Change "supracondular, or condular" to --supracondylar, or condylar--.

In column 11 at line 27, After "proximal end" change "and or" to --and/or--.

In column 11 at line 27, After "distal end" change "and or" to --and/or--.

In column 14 at line 15, Change "114'," to --114",--.

In column 16 at line 41, Change "100'''similar" to --100''' similar--.

In column 21 at line 44, Change "it" to --its--.

In column 22 at line 50, Change "malleoulus" to --malleolus--.

In column 22 at line 52, Change "themetatarsus;" to --the metatarsus;--.

Signed and Sealed this  
Twenty-sixth Day of March, 2013

Teresa Stanek Rea  
*Acting Director of the United States Patent and Trademark Office*